US011008624B2

(12) United States Patent
Luo et al.

(10) Patent No.: US 11,008,624 B2
(45) Date of Patent: May 18, 2021

(54) METHODS FOR PREDICTING PROSTATE CANCER RELAPSE

(71) Applicant: UNIVERSITY OF PITTSBURGH—OF THE COMMONWEALTH SYSTEM OF HIGHER EDUCATION, Pittsburgh, PA (US)

(72) Inventors: Jianhua Luo, Wexford, PA (US); Yanping Yu, Wexford, PA (US); Chien-Cheng Tseng, Pittsburgh, PA (US); Shuchang Liu, Pittsburgh, PA (US); George Michalopoulos, Pittsburgh, PA (US); Joel Nelson, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 94 days.

(21) Appl. No.: 15/890,789

(22) Filed: Feb. 7, 2018

(65) Prior Publication Data
US 2018/0230547 A1 Aug. 16, 2018

Related U.S. Application Data

(63) Continuation of application No. PCT/US2016/046051, filed on Aug. 8, 2016.

(60) Provisional application No. 62/202,532, filed on Aug. 7, 2015.

(51) Int. Cl.
C12Q 1/6886 (2018.01)
C12Q 1/6837 (2018.01)

(52) U.S. Cl.
CPC ......... *C12Q 1/6886* (2013.01); *C12Q 1/6837* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 2008/0274909 | A1 | 11/2008 | Brothman |
| 2009/0029362 | A1 | 1/2009 | Timms et al. |
| 2010/0261617 | A1 | 10/2010 | Poustka et al. |
| 2011/0287034 | A1 | 11/2011 | Frank et al. |
| 2012/0220672 | A1 | 8/2012 | Pestano et al. |
| 2013/0079241 | A1 | 3/2013 | Luo et al. |
| 2013/0225420 | A1 | 8/2013 | Albertson et al. |

FOREIGN PATENT DOCUMENTS

| WO | WO 03/101530 A2 | 12/2003 |
| WO | WO 2006/012646 A2 | 2/2006 |
| WO | WO 2008/016374 A2 | 2/2008 |
| WO | WO 2008/023087 A2 | 2/2008 |
| WO | WO 2010/056337 A2 | 5/2010 |
| WO | WO 2010/138460 A1 | 12/2010 |
| WO | WO 2012/139134 A2 | 10/2012 |
| WO | WO 2013/037118 A1 | 3/2013 |
| WO | WO 2013/106737 A1 | 7/2013 |
| WO | WO 2014/018673 A2 | 1/2014 |
| WO | WO 2014/039556 A1 | 3/2014 |
| WO | WO 2015/103057 A1 | 7/2015 |
| WO | WO 2015/106341 A1 | 7/2015 |

OTHER PUBLICATIONS

U.S. Appl. No. 13/619,556, (US 2013/0079241), filed Sep. 14, 2012 (Mar. 28, 2013) (Abandoned).
U.S. Appl. No. 14/336,965 (US 2015/0050647), filed Jul. 21, 2014 (Feb. 19, 2015).
U.S. Appl. No. 14/336,965, Mar. 15, 2019 Final Office Action.
U.S. Appl. No. 14/336,965, Dec. 19, 2018 Response to Restriction Requirement.
U.S. Appl. No. 14/336,965, Oct. 19, 2018 Restriction Requirement.
U.S. Appl. No. 14/336,965, Jul. 20, 2018 Response to Non-Final Office Action.
U.S. Appl. No. 14/336,965, Mar. 20, 2018 Non-Final Office Action.
U.S. Appl. No. 14/336,965, Jun. 7, 2017 Amendment and Request for Continued Examination (RCE).
U.S. Appl. No. 14/336,965, Feb. 7, 2017 Final Office Action.
U.S. Appl. No. 14/336,965, Nov. 2, 2016 Response to Non-Final Office Action.
U.S. Appl. No. 14/336,965, May 2, 2016 Non-Final Office Action.
U.S. Appl. No. 14/336,965, Feb. 3, 2016 Response to Restriction Requirement.
U.S. Appl. No. 14/336,965, Aug. 3, 2015 Restriction Requirement.
U.S. Appl. No. 13/619,556, Sep. 30, 2014 Notice of Abandonment.
U.S. Appl. No. 13/619,556, Jul. 3, 2014 Advisory Action.
U.S. Appl. No. 13/619,556, Jun. 19, 2014 Response to Final Office Action.
U.S. Appl. No. 13/619,556, Feb. 21, 2014 Final Office Action.

(Continued)

*Primary Examiner* — Carla J Myers
(74) *Attorney, Agent, or Firm* — Baker Botts L.L.P.

(57) ABSTRACT

The present invention relates to methods for determining whether a subject having prostate cancer is at an increased risk for relapse or rapid relapse. It is based, at least in part, on the results of a comprehensive genome analysis of 273 prostate cancer samples, which indicate that the percentage of large size CNVs predicts prostate cancer relapse. In certain embodiments, a method for determining whether a prostate cancer patient has an increased risk of suffering a relapse or a rapid relapse comprises determining the number and size of CNVs in a sample and determining a large size ratio, where if the large size ratio exceeds a particular threshold, the patient is deemed to be at an increased risk for relapse or rapid relapse.

8 Claims, 15 Drawing Sheets

(56) References Cited

OTHER PUBLICATIONS

Figure 1A:
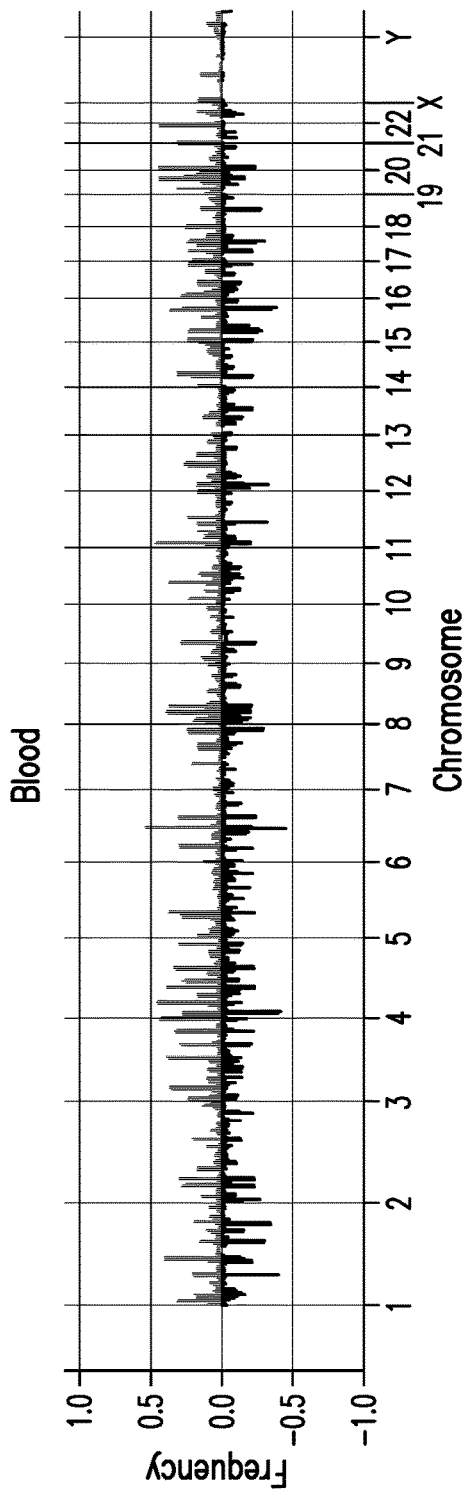

U.S. Appl. No. 13/619,556, Nov. 14, 2013 Response to Non-Final Office Action.
U.S. Appl. No. 13/619,556, Jul. 16, 2013 Non-Final Office Action.
U.S. Appl. No. 13/619,556, May 13, 2013 Response to Restriction Requirement.
U.S. Appl. No. 13/619,556, Mar. 12, 2013 Restriction Requirement.
Agarwal et al., "Zinc metalloproteinase, ZMPSTE24, is mutated in mandibuloacral dysplasia," Human Molecular Genetics 12(16):1995-2001 (2003).
Ahn et al., "Fer Protein-Tyrosine Kinase Promotes Lung Adenocarcinoma Cell Invasion and Tumor Metastasis," Mol. Cancer Res 11(8):952-963 (2013).
Anderson et al., "A simple method for the rapid generation of recombinant adenovirus vectors," Gene Therapy 7:1034-1038 (2000).
Antonarakis et al., "Changes in PSA Kinetics Predict Metastasis-Free Survival in Men with PSA-Recurrent Prostate Cancer Treated with Nonhormonal Agents. Combined Analysis of 4 Phase II Trials," Cancer 118:1533-1542 (2012).
Baca et al., "Punctuated Evolution of Prostate Cancer Genomes," Cell 153:666-677 (2013).
Bae et al., "Low Frequency Mutation of the Ephrin Receptor A3 Gene in Hepatocellular Carcinoma," Neoplasma, 56(4):331-334 (2009).
Bar-Peled et al., "A Tumor Suppressor Complex with GAP Activity for the Rag GTPases That Signal Amino Acid Sufficiency to mTORC1," Science 340:1100-1106 (2013).
Berger et al., "The genomic complexity of primary human prostate cancer," Nature 470:214-220 (2011).
Bettendorf et al., "Cytogenetic Changes and Loss of Heterozygosity in Atypical Adenomatous Hyperplasia, in Carcinoma of the Prostate and in Non-Neoplastic Prostate Tissue Using Comparative Genomic Hybridization and Multiplex-PCR," International Journal of Oncology, 26(1):267-274 (2005).
Blackford et al., "Genetic Mutations Associated with Cigarette Smoking in Pancreatic Cancer," Cancer Research, 69(8):3681-3688 (2009).
Budd et al., "Circulating Tumor Cells Versus Imaging-Predicting overall survival in Metastatic Breast Cancer," Clinical Cancer Research, 12(21):6403-6409 (2006).
Carver et al., "ETS rearrangements and prostate cancer initiation," Nature 457:El; discussion E2-3 (2009).
Chi et al., "ETV1 is a lineage survival factor that cooperates with KIT in gastrointestinal stromal tumours," Nature 467:849-853 (2010).
Clark et al., "ETS gene fusions in prostate cancer," Nat Rev Urol. 6:429-439 (2009).
Clifford et al., "The EphA3 Receptor is Expressed in a Subset of Rhabdomyosarcoma Cell Lines and Suppresses Cell Adhesion and Migration," Journal of Cellular Biochemistry, 105:1250-1259 (2008).
Corban-Wilhelm et al., "Cytosine deaminase versus thymidine kinase: a comparison of the antitumor activity," Clinical and Experimental Medicine, 3(3):150-156 (2003).
Demichelis et al., "TMPRSS2:ERG gene fusion associated with lethal prostate cancer in a watchful waiting cohort," Oncogene, 26:4596-4599 (2007).
Derwent Abstract Accession No. 2013-E07845 (accessed on Sep. 21, 2016).
Edgren et al., "Identification of fusion genes in breast cancer by paired-end Rna-sequencing," Genome Biol. 12:R6 (2011).
El Gammal et al., "Chromosome 8p Deletions and 8q Gains are Associated with Tumor Progression and Poor Prognosis in Prostate Cancer," Clin Cancer Research 16(1):56-64 (2010).
Enard et al., "Intra- and Interspecific Variation in Primate Gene," Science 296:340 (2002).
Enninga et al., "Sec13 Shuttles between the Nucleus and the Cytoplasm and Stably Interacts with Nup96 at the Nuclear Pore Complex," Molecular and Cellular Biology 23(20):7271-7284 (2003).
Esvelt et al., "Concerning RNA-guided gene drives for the alteration of wild populations," eLife 3:e03401 (2014).

Extended European Search Report dated Feb. 12, 2019 in EP Application No. 16835759.8.
Fisher et al., "A Novel Cyclin Associates with M015/CDK7 to Form the CDK-Activating Kinase," Cell 78:713-724 (1994).
Fitzgerald et al., "Association of TMPRSS2-ERG gene fusion with clinical characteristics and outcomes: results from a population-based study of prostate cancer," BMC Cancer 8:230 (2008).
Freedland et al., "Death in Patients with Recurrent Prostate Cancer after Radical Prostatectomy: Prostate-Specific Antigen Doubling Time Subgroups and Their Associated Contributions to All-Cause Mortality," J Clin Oncol 25(13):1765-1771 (2007).
Gittes, "Carcinoma of the Prostate," the New England Journal of Medicine 324(4):236-245 (1991).
Golub et al., "Molecular Classification of Cancer: Class Discovery and Class Prediction by Gene Expression Monitoring," Science, 286:531-537 (1999).
Green et al., "Integrative analysis Reveals Selective 9p24.1 Amplification, Increased PD1 Ligand Expression, and Further Induction via JAK2 in Nodular Sclerosing Hodgkin Lymphoma and Primary Mediastinal Large B-Cell Lymphoma," Blood, 116(17):3268-3277 (2010).
Guo et al., "FER tyrosine kinase (FER) overexpression mediates resistance to quinacrine through EGF-dependent activation of NF-KB," PNAS USA 108(19):7968-7973 (2011).
Hakkarainen et al., "A conditionally replicative adenovirus that codes for a TKGFP fusion protein (Ad5Delta24TK-GFP) for evaluation of the potency of oncolytic virotherapy combined with molecular chemotherapy," International Journal of Molecular Medicine, 18(4):751-759 (2006).
Han et al., "Interaction of integrin-linked kinase (ILK) and MCM7 mediating integrin a7 induced cell growth suppression," Cancer Research 70(11):4375-4384 (2010).
Han et al., "Metallothionein 1 h tumour suppressor activity in prostate cancer is mediated by euchromatin methyltransferase 1," the Journal of Pathology 230(2):184-193 (2013).
Hanczar et al., "Small-Sample Precision of ROC-Related Estimates," Bioinformatics, 26(6):822-830 (2010).
Hanks et al., "Pretreatment Prostate-Specific Antigen Doubling times: Clinical Utility of this Predictor of Prostate Cancer Behavior," Int. J. Radiation Oncology Biol. Phys., 34(3):549-553 (1996).
Hao et al., "Isolation and Sequence Analysis of a Novel Human Tyrosine Kinase Gene," Mol. Cell Biol 9(4):1587-1593 (1989).
Heitzer et al., "Tumor-associated copy number changes in the circulation of patients with prostate cancer identified through whole-genome sequencing," Genome Medicine, 5(30):1-16 (2013).
Hieronymus et al., "Copy number alteration burden predicts prostate cancer relapse," PNAS, 111(30):11139-11144 (2014).
International Search Report and Written Opinion dated Apr. 1, 2015 in International Application No. PCT/US2014/072268.
International Search Report dated Oct. 17, 2016 in International Application No. PCT/US2016/046051.
International Search Report dated Oct. 7, 2015 in International Application No. PCT/US2015/041029.
Isaacs, "Molecular Markers for Prostate Cancer Metastasis," American Journal of Pathology, 150(5):1511-1521 (1997).
Ivanova et al., "FER kinase promotes breast cancer metastasis by regulating α6- and β1-integrin-dependent cell adhesion and anoikis resistance," Oncogene 32:5582-5592 (2013).
Jane-Valbuena et al., "An Oncogenic Role for ETV1 in Melanoma," Cancer Research 70(5):2075-2084 (2010).
Jemal et al., "Global Cancer Statistic," CA Cancer J. Clin., 59:225-249 (2009).
Jemal et al., "Global Cancer Statistic," CA Cancer J. Clin., 60:277-300 (2010).
Jemal et al., "Global Cancer Statistic," CA Cancer J. Clin., 61:69-90 (2011).
Jeon et al., "A variant Ewing's sarcoma translocation (7;22) fuses the EWS gene to the ETS gene ETV1," Oncogene 10:1229-1234 (1995).
Jinek et al., "A Programmable Dual-RNA-Guided DNA Endonuclease in Adaptive Bacterial Immunity," Science 337:816-821 (2012).

(56) References Cited

OTHER PUBLICATIONS

Jing et al., "Expression of Myopodin Induces Suppression of Tumor Growth and Metastasis," the American Journal of Pathology 164(5):1799-1806 (2004).
Kawakami et al., "FER overexpression is associated with poor postoperative prognosis and cancer-cell survival in non-small cell lung cancer," Int J Clin Exp Pathol 6(4):598-612 (2013).
Kim et al., "Integrative analysis of Genomic Aberrations Associated with Prostate Cancer Progression," Cancer Research, 67(17):8229-8239 (2007).
Koutras et al., "The Upgrade Role of HER3 and HER4 Receptors in Breast cancer," Critical Reviews in Oncology/Hematology, 74:73-78 (2010).
Krastev et al., "A systematic RNAi synthetic interaction screen reveals a link between p53 and snoRNP assembly," Nature Cell Biology 13(7):809-818 (2011).
Kraus et al., "High-Resolution Genomic Profiling of Occult Micrometastatic Tumor Cells," Genes, Chromosomes & Cancer 36:159-166 (2003).
Krolewski et al., "Identification and chromosomal mapping of new human tyrosine kinase genes," Oncogene 5:277-282 (1990).
Kwok et al., "FES Kinase Promotes Mast Cell Recruitment to Mammary Tumors via the Stem Cell Factor/KIT Receptor Signaling Axis," Mol. Cancer Res 10(7):881-891 (2012).
Lee et al., "Somatic Mutation in Epidermal Growth Factor Receptor Signaling Pathway Genes in Non-Small Cell Lung Cancers," Journal of Thoracic Oncology, 5(11):1734-1740 (2010).
Li et al., "Fast and accurate long-read alignment with Burrows-Wheeler transform," Bioinformatics 26(5):589-595 (2010).
Li et al., Identification of tyrosine-phosphorylated proteins associated with metastasis and functional analysis of FER in human hepatocellular carcinoma cells, BMC Cancer 9:366 (2009).
Lin et al., "Myopodin, a Synaptopodin Homologue, is Frequently Deleted in Invasive Prostate Cancers," Am J of Pathol 159:1603-1612 (2001).
Liu et al., "Comprehensive Assessment of DNA Copy Number Alterations in Human Prostate Cancers Using Affymetrix 100K SNP Mapping Array," Genes, Chromosomes & Cancer, 45:1018-1032 (2006).
Liu et al., "Copy number analysis indicates monoclonal origin of lethal metastatic prostate cancer," Nature Medicine 15(5):559-565 (2009).
Loimas et al., "Human prostate carcinoma cells as targets for herpes simplex virus thymidine kinase-mediated suicide gene therapy," Cancer Gene Therapy, 8(2):137-144 (2001).
Luo et al., "(−)-Epigallocatechin-3-gallate induces Du 145 prostate cancer cell death via downregulation of inhibitor of DNA binding 2, a dominant negative helix-loop-helix protein," Cancer Science 101(3):707-712 (2010).
Luo et al., "Discovery and Classification of Fusion Transcripts in Prostate Cancer and Normal Prostate Tissue," Am J Pathol 185:1834-1845 (2015).
Luo et al., "Gene Expression Analysis of Prostate Cancers," Molecular Carcinogenesis 33:25-35 (2002).
Luo et al., "Genetic factors underlying prostate cancer," Expert Reviews in Molecular Medicine 5:1-26 (2003).
Luo et al., "Genome-Wide Methylation Analysis of Prostate Tissues Reveals Global Methylation Patterns of Prostate Cancer," the American Journal of Pathology 182(6):2028-2036 (2013).
Macoska et al., "Evolution of 8p loss in transformed human prostate epithelial cells," Cancer Genetics and Cytogenetics 154:36-43 (2004).
Matsui et al., "Molecular characterization of a consistent 4.5-megabase deletion at 4q28 in prostate cancer cells," Cancer Genetics and Cytogenetics 159:18-26 (2005).
Misago et al., "Molecular cloning and expression of cDNAs encoding human α-mannosidase II and a previously unrecognized a-mannosidase IIx isozyme," Proc Natl Acad Sci USA 92:11766-11770 (1995).
Miyata et al., "Feline sarcoma-related protein expression correlates with malignant aggressiveness and poor prognosis in renal cell carcinoma," Cancer Sci 104(6):681-686 (2013).
Mojica et al., "Intervening Sequences of Regularly Spaced Prokaryotic Repeats Derive from Foreign Genetic Elements," J Mol. Evol 60:174-182 (2005).
Monaco, "Fatty Acid Metabolism in Breast Cancer Subtypes," Oncotarget 8(17):29487-29500 (2017).
Moremen et al., "Isolation, Characterization, and Expression of cDNAs Encoding Murine α-Mannosidase II, a Golgi Enzyme That Controls Conversion of High Mannose to Complex N-Glycans," J Cell Biol. 115(6):1521-1534 (1991).
Moreno et al., "Detection of Hematogenous Micrometastasis in Patients with Prostate Cancer," Cancer Research, 52:6110-6112 (1992).
Nam et al., "Expression of TMPRSS2 ERG Gene Fusion in Prostate Cancer Cells is an Important Prognostic Factor for Cancer Progression," Cancer Biology & Therapy 6(1):40-45 (2007).
Nellist et al., "Phosphorylation and binding partner analysis of the TSC1-TSC2 complex," Biochemical and Biophysical Research Communications 333:818-826 (2005).
Nunez et al., "WWOX Protein Expression Varies Among Ovarian Carcinoma Histotypes and Correlates with Less Favorable Outcome," BMC Cancer, 5:64 (2005).
Pang et al., "Cytogenetic and Expression Profiles Associated with Transformation to Androgen-Resistant Prostate Cancer," the Prostate 66:157-172 (2006).
Parkin et al., "Acquired Genomic Copy Number Aberrations and Survival in Adult Acute Myelogenous Leukemia," Blood, 116(23):4958-4967 (2010).
Parr-Sturgess et al., "Copper Modulates Zinc Metalloproteinase-Dependent Ectodomain Shedding of Key Signaling and Adhesion Proteins and Promotes the Invasion of Prostate Cancer Epithelial Cells," Mol. Cancer Res 10(10):1282-1293 (2012).
Partial Supplemental European Search Report dated Jul. 12, 2017 in EP Application No. 14875963.2.
Partin et al., "The Use of Prostate Specific Antigen, Clinical Stage and Gleason Score to Predict Pathological Stage in Men with Localized Prostate Cancer," the Journal of Urology 150: 110-114 (1993).
Perner et al., "784-TMPRSS2-ERG Gene Fusion Defines a Metastatic Phenotype of Prostate Cancer," Eur Urol Suppl 8(4):316 (2009).
Potosky et al., "The Role of Increasing Detection in the Rising Incidence of Prostate Cancer," JAMA 273(7):548-552 (1995).
Prakash et al., "Expression of Conjoined Genes: Another Mechanism for Gene Regulation in Eukaryotes," PLoS One 5(10):e13284 (2010).
Ran et al., "Double Nicking by RNA-Guided CRISPR Cas9 for Enhanced Genome Editing Specificity," Cell, 154:1380-1389 (2013).
Ren et al., "Analysis of Integrin α7 Mutations in Prostate Cancer, Liver Cancer, Glioblastoma Multiforme, and Leiomyosarcoma," J Natl Cancer Inst 99:868-880 (2007).
Ren et al., "MCM7 amplification and overexpression are associated with prostate cancer progression," Oncogene 25:1090-1098 (2006).
Rickman et al., "SLC45A3-ELK4 is a novel and frequent erythroblast transformation-specific fusion transcript in prostate cancer," Cancer Research, 69(7):2734-2738 (2009).
Robin et al., "pROC: an open-source package for R and S+ to analyze and compare ROC curves," BMC Bioinformatics 12:77 (2011).
Rocha et al., "The Fer tyrosine kinase acts as a downstream interleukin-6 effector of androgen receptor activation in prostate cancer," Mol. Cell Endocrinol 381:140-149 (2013).
Sander et al., "CRIRISPR-Cas systems for editing, regulating and targeting genomes," Nature Biotechnology, 32(4):347-355 (2014).
Savolainen et al., "A mouse model for a-methylacyl-CoA racemase deficiency: adjustment of bile acid synthesis and intolerance to dietary methyl-branched lipids," Hum Mol Genet 13(9):955-965 (2004).
Sebat et al., "Large-Scale Copy Number Polymorphism in the Human Genome," Science 305:525-528 (2004).

(56) References Cited

OTHER PUBLICATIONS

Shchors et al., "Cell Death Inhibiting RNA (CDIR) Derived from a 3'-Untranslated Region Binds AUF1 and Heat Shock Protein 27*," the Journal of Biological Chemistry 277(49):47061-47072 (2002).
Sheu et al., "Chromosome 3p12.3-p14.2 and 3q26.2-q26.32 are Genomic Markers for Prognosis of Advanced Nasopharyngeal Carcinoma," Cancer Epidemiol Biomarkers Prev 18(10):2709-2716 (2009).
Shi et al., "Inhibition of prostate cancer growth and metastasis using small interference RNA specific for minichromosome complex maintenance component 7," Cancer Gene Therapy 17(10):694-699 (2010).
Siegel et al., "Cancer Statistics for Hispanics/Latinos, 2012," CA Cancer J Clin 62:283-298 (2012).
Siegel et al., "Cancer Statistics, 2012," CA Cancer J Clin. 62:10-29 (2012).
Siegel et al., "Cancer Statistics, 2015," CA Cancer J Clin 65:5-29 (2015).
Sinclair et al., "A Fluorescence in situ Hybridization Map of 6q Deletions in Acute Lymphocytic Leukemia: Identification and Analysis of a Candidate Tumor Suppressor Gene," Cancer Res. 64:4089-4098 (2004).
Smith et al., "A New Nucleoside Analog, 9-[[2-Hydroxy-1-(Hydroxymethyl)Ethoxy]Methyl] Guanine, Highly Active in Vitro Against Herpes Simplex Virus Types 1 and 2," Antimicrobial Agents and Chemotherapy 22:55-61 (1982).
Stephenson et al., "Salvage Radiotherapy for Recurrent Prostate Cancer After Radical Prostatectomy," JAMA, 291(11):1325-1332 (2004).
Strassburger et al., "Compatible Simultaneous Lower Confidence Bounds for the Holm Procedure and other Bonferroni-Based Closed Tests," Statistics in Medicine, 27:4914-4927 (2008).
Strausberg et al., "Generation and Initial Analysis of More Than 15,000 Full-Length Human and Mouse cDNA Sequences," PNAS, 99(26):16899-16903 (2002).
Swanson et al., "TMPRSS2/ERG Fusion Gene Expression Alters Chemo- and Radio-Responsiveness in Cell Culture Models of Androgen Independent Prostate Cancer," the Prostate 71:1548-1558 (2011).
Taylor et al., "Integrative Genomic Profiling of Human Prostate Cancer," Cancer Cell 18:11-22 (2010).
Teixeira et al., "Genomic Analysis of Prostate Carcinoma Specimens Obtained via Ultrasound-Guided Needle Biopsy May be of Use in Preoperative Decision-Making," Cancer 101:1786-1793 (2004).
Tomlins et al., "Recurrent Fusion of TMPRSS2 and ETS Transcription Factor Genes in Prostate Cancer," Science 310:644-648 (2005).
Towns et al., "Transfer RNA Methytransferases and their Corresponding Modifications in Budding Yeast and Humans: Activities, Predications, and Potential Roles in Human Health," Dna and Cell Biology 31(4):434-454 (2012).
Trapnell et al., "Differential gene and transcript expression analysis of RNA-seq experiments with TopHat and Cufflinks," Nat Protoc. 7(3):562-578 (2012).
Trapnell et al., "TopHat: discovering splice junctions with RNA-Seq.," Bioinformatics 25(9):1105-1111 (2009).
Trapnell et al., "Transcript assembly and quantification by RNA-Seq reveals unannotated transcripts and isoform switching during cell differentiation," Nat. Biotechnol. 28(5):511-515 (2010).
Tsang et al., "Scaper, a Novel Cyclin A-Interacting Protein that Regulates Cell Cycle Progression," Journal of Cell Biology, 178(4):621-633 (2007).
Vitari et al., "COP1 is a tumour suppressor that causes degradation of ETS transcription factors," Nature 474:402-408 (2011).
Voisset et al., "The tyrosine kinase FES is an essential effector of KITD816V proliferation signal," Blood 110(7):2593-2599 (2007).
Wang et al., "Expression of variant TMPRSS2/ERG fusion messenger RNAs is associated with aggressive prostate cancer," Cancer Research, 66(17):8347-8351 (2006).
Wang et al., "p53-induced Gene 3 Mediates Cell Death Induced by Glutathione Peroxidase 3," J Biol Chem 287(20):16890-16902 (2012).
Watabe-Uchida et al., "The Rac Activator DOCK7 Regulates Neuronal Polarity through Local Phosphorylation of Stathmin/Op18," Neuron 51:727-739 (2006).
Wei et al., "High expression of FER tyrosine kinase predicts poor prognosis in clear cell renal cell carcinoma," Oncol Lett 5:473-478 (2013).
Willardsen et al., "The ETS transcription factor Etv 1 mediates FGF signaling to initiate proneural gene expression during Xenopus laevis retinal development," Mechanisms of Development 131:57-67 (2014).
Xia et al., "Plasma genetic and genomic abnormalities predict treatment response and clinical outcome in advanced prostate cancer," Oncotarget 6(18):16411-16421 (2015).
Yakicier et al., "Identification of Homozygous Deletions at Chromosome 16q23 in Aflatoxin B1 Exposed Hepatocellular Carcinoma," Oncogene, 20:5232-5238 (2001).
Yang et al., "Deletion of the WWOX gene and Frequent Loss of its Protein Expression in Human Osteosarcoma," Cancer Letter, 291:31-38 (2010).
Yang et al., "Genome-wide Copy-Number-Variation Study Identified a Susceptibility Gene, UGT2B17, for Osteoporosis," the American Journal of Human Genetics 83:663-674 (2008).
Yang et al., "mTOR kinase structure, mechanism and regulation," Nature 497:217-223 (2013).
Yang et al., "The Histone Demethylase JMJD2B is Regulated by Estrogen Receptor a and Hypoxia, and is a Key Mediator of Estrogen Induced Growth," Cancer Res 70(16):6456-6466 (2010).
Youden, "Index for Rating Diagnostic Tests," Cancer 3:32-35 (1950).
Yu et al., "CSR1 Suppresses Tumor Growth and Metastasis of Prostate Cancer," American Journal of Pathology 168(2):597-607 (2006).
Yu et al., "Gene Expression Alterations in Prostate Cancer Predicting Tumor Aggression and Preceding Development of Malignancy," Journal of Clinical Oncology, 22(14):2790-2799 (2004).
Yu et al., "Genome Abnormalities Precede Prostate Cancer and Predict Clinical Relapse," the American Journal of Pathology, 180(6):2240-2248 (2012).
Yu et al., "Genomic Copy Number Variations in the Genomes of Leukocytes Predict Prostate Cancer Clinical Outcomes," PLOS One, 10(8):e0135982, pp. 1-17 (2015).
Yu et al., "Glutathione Peroxidase 3, Deleted or Methylated in Prostate Cancer, Suppresses Prostate Cancer Growth and Metastasis," Cancer Research 67(17):8043-8050 (2007).
Yu et al., "High throughput screening of methylation status of genes in prostate cancer using an oligonucleotide methylation array," Carcinogenesis 26(2):471-479 (2005).
Yu et al., "Inactivation of Myopodin Expression Associated with Prostate Cancer Relapse," Urology 68:578-582 (2006).
Yu et al., "Novel Fusion Transcripts Associate with Progressive Prostate Cancer," the American Journal of Pathology, 184(10):2840-2849 (2014).
Yu et al., "Pathological factors evaluating prostate cancer," Histol Histopathol 22:1291-1300 (2007).
Zarrei et al., "A copy number variation map of the human genome," Nat Rev Genet 16:172-183 (2015).
Zeng et al., "Visualizing Interchange Patterns in Massive Movement Data," Computer Graphics Forum 32(3):271-280 (2013).
Zha et al., "a-Methylacyl-CoA Racemase as an Androgen-Independent Growth Modifier in Prostate Cancer," Cancer research 63:7365-7376 (2003).
Zhao et al., "Genome-Wide Characterization of Gene Expression Variations and DNA Copy Number Changes on Prostate Cancer Cell Lines," the Prostate, 63:187-197 (2005).
Zhen et al., "Nuclear Import of Exogenous FGF1 Requires the ER-Protein LRRC59 and the Importins Kpnal and Kpnf31," Traffic 13:650-664 (2012).
Zhou et al., "Peripheral Blood Mitochondrial DNA Copy Number is Associated with Prostate Cancer Risk and Tumor Burden," PLoS One 9(10):e109470 (2014).

(56) References Cited

OTHER PUBLICATIONS

Zhu et al., "CSR1 induces cell death through inactivation of CPSF3," Oncogene 28:41-51 (2009).
Zhu et al., "Integrin Alpha 7 Interacts with High Temperature Requirement A2 (HtrA2) to Induce Prostate Cancer Cell Death," the American Journal of Pathology 177(3):1176-1186 (2010).

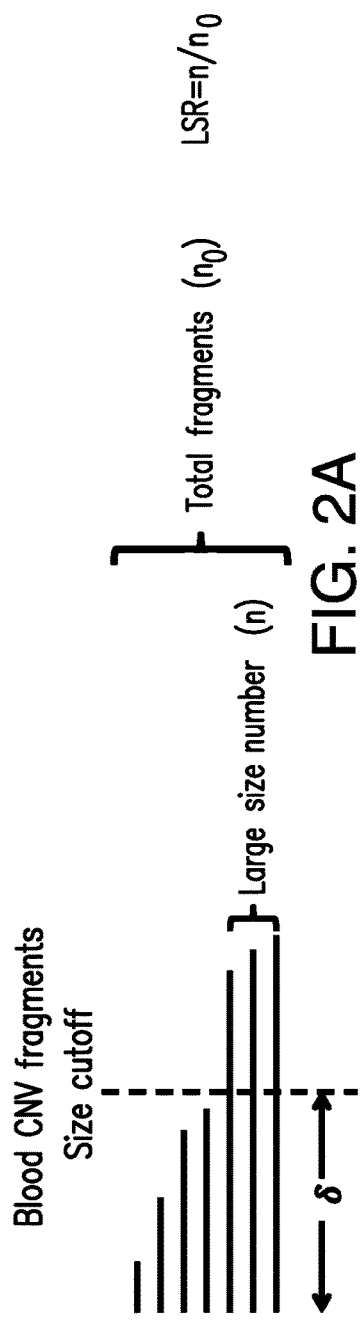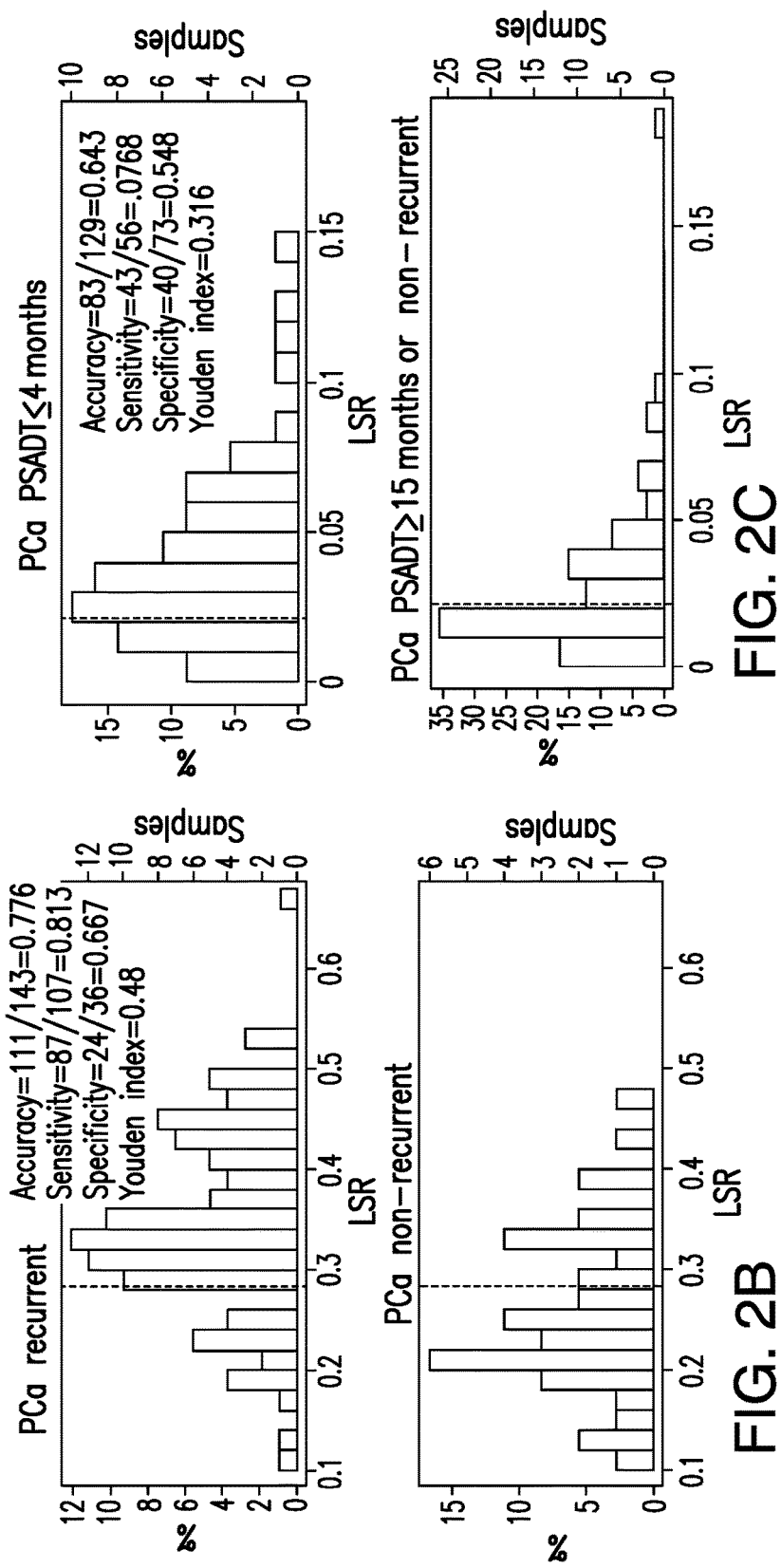

METHODS FOR PREDICTING PROSTATE CANCER RELAPSE

CROSS-REFERENCE TO RELATED APPLICATIONS

This application is a continuation of International Patent Application No. PCT/US2016/046051, filed Aug. 8, 2016, which claims priority to U.S. Provisional Patent Application Ser. No. 62/202,532, filed Aug. 7, 2015, to which priority is claimed and the contents of which are incorporated herein in its entirety.

GRANT INFORMATION

This invention was made with government support under Grant No. CA098249 awarded by the National Cancer Institute. The government has certain rights in the invention.

1. INTRODUCTION

The present invention relates to methods for determining whether a subject having prostate cancer is at increased risk for relapse or rapid relapse.

2. BACKGROUND OF THE INVENTION

Prostate cancer is one of the leading causes of death for men in the United States, and about 30,000 patients die of prostate cancer annually (4). Since the implementation of serum prostate specific antigen (PSA) screening, the clinical detection rate of prostate cancer has increased substantially due primarily to the identification of small, low grade cancers that would likely not progress (1). Several treatment options are available for prostate cancer patients including watchful waiting, radiation, hormonal/chemo-therapy and radical prostatectomy. Gleason grading, alone or in combination with other clinical indicators such as serum PSA levels, and pathological or clinical staging, has been the guiding tool in selecting these treatment options. However, prostate cancer has considerable heterogeneity in biological aggressiveness and clinical prognosis (1-3) and accurate prediction of the aggressive behavior of prostate cancer remains difficult. In addition, a significant number of prostate cancer patients experience recurrence after surgical resection of the prostate gland. Therefore, there is a need in the art for methods for more accurately determining the prognosis of prostate cancer.

3. SUMMARY OF THE INVENTION

The present invention relates to methods for determining whether a prostate cancer patient is at increased risk of suffering a relapse or a rapid relapse of his cancer and further relates to kits for performing such methods. It is based, at least in part, on the results of a comprehensive genome analysis performed on 273 prostate cancer samples, which indicate that the percentage of large size CNVs predicts prostate cancer relapse.

The present invention provides methods for determining whether a prostate cancer patient is at an increased risk of suffering a relapse or a rapid relapse. In certain embodiments, the method comprises determining the number and size of CNVs in a sample and determining the large size ratio, where if the large size ratio (LSR) exceeds a particular threshold, the patient is deemed to be at an increased risk for relapse or rapid relapse (relative to subjects having a LSR below that threshold). In certain embodiments, the sample can be a blood sample or a tumor sample. In certain embodiments, the large size ratio is calculated by dividing the number of CNVs that are larger in size than a cut-off value by the total number of CNVs. In certain embodiments, the cut-off value is about 25 kb or about 30 kb, and a large size ratio equal to or greater than about 0.28 is indicative that the patient is at an increased risk for relapse. In certain embodiments, the cut-off value is about 400 or about 500 kb, and a large size ratio equal to or greater than about 0.02 is indicative that the patient is at an increased risk for rapid relapse.

The present invention further provides methods for determining whether a prostate cancer patient is at a decreased risk of suffering a relapse or a rapid relapse. In certain embodiments, the method comprises determining the number and size of CNVs in a sample and determining the large size ratio, where if the large size ratio is less than a particular threshold, the patient is deemed to be at a decreased risk for relapse or rapid relapse. In certain embodiments, the sample can be a blood sample or a tumor sample. In certain embodiments, the large size ratio is calculated by dividing the number of CNVs that are larger in size than a cut-off value by the total number of CNVs. In certain embodiments, the cut-off value is about 25 kb or about 30 kb, and a large size ratio less than about 0.28 is indicative that the patient is at a decreased risk for relapse. In certain embodiments, the cut-off value is about 400 or about 500 kb, and a large size ratio less than about 0.02 is indicative that the patient is at a decreased risk for rapid relapse.

The present invention further provides a method for treating a prostate cancer patient that includes determining whether the prostate cancer patient is at increased risk for relapse or rapid relapse, where if the prostate cancer patient is deemed to be at an increased risk for relapse or rapid relapse, then performing a prophylactic and/or treatment regimen. In certain embodiments, determining whether the prostate cancer patient is at an increased risk for relapse or rapid relapse comprises determining the number and size of copy number variations (CNVs) in a sample from the patient and determining a large size ratio, where if the large size ratio exceeds a particular threshold, the patient is deemed to be at an increased risk for relapse or rapid relapse. In certain embodiments, the large size ratio is calculated by dividing the number of CNVs that are larger in size than a cut-off value by the total number of CNVs. In certain embodiments, the cut-off value is about 25 kb or about 30 kb. Alternatively, the cut-off value is about 400 or about 500 kb. In certain embodiments, a large size ratio equal to or greater than about 0.28 is indicative that the patient is at an increased risk for relapse. In certain embodiments, a large size ratio equal to or greater than about 0.02 is indicative that the patient is at an increased risk for rapid relapse. In certain embodiments, the prophylactic and/or treatment regimen is selected from the group consisting of cryotherapy, radiation therapy, chemotherapy, hormone therapy, biologic therapy, bisphosphonate therapy, high-intensity focused ultrasound, frequent monitoring, frequent prostate-specific antigen (PSA) checks, radical prostatectomy and combinations thereof.

The present invention further provides a method for treating a prostate cancer patient comprising determining whether the prostate cancer patient is at a decreased risk for relapse or rapid relapse, where if the prostate cancer patient is deemed to be at a decreased risk for relapse or rapid relapse, then performing one or more of the following: high-intensity focused ultrasound, watchful waiting, frequent monitoring, frequent PSA checks and/or a biopsy. In certain embodiments, determining whether the prostate cancer patient is at a decreased risk for relapse or rapid relapse can include determining the number and size of copy number variations (CNVs) in a sample from the patient and determining a large size ratio, where if the large size ratio is less than a particular threshold, the patient is deemed to be at a decreased risk for relapse or rapid relapse. In certain embodiments, the large size ratio is calculated by dividing the number of CNVs that are larger in size than a cut-off value by the total number of CNVs. In certain embodiments, the cut-off value is about 25 kb or about 30 kb. Alternatively, the cut-off value is about 400 or about 500 kb. In certain embodiments, a large size ratio less than about 0.28 is indicative that the patient is at a decreased risk for relapse. In certain embodiments, a large size ratio less than about 0.02 is indicative that the patient is at a decreased risk for rapid relapse.

In certain embodiments, a method of determining that a prostate cancer patient is at an increased risk for relapse comprises determining the number and size of copy number variations (CNVs) in a sample from the patient and determining a large size ratio, where if the large size ratio is greater than or equal to about 0.28, the patient is deemed to be at an increased risk for relapse. In certain embodiments, the large size ratio is calculated by dividing the number of CNVs that are larger in size than a cut-off value of about 25 kb or about 30 kb by the total number of CNVs.

In certain embodiments, a method of determining that a prostate cancer patient is at an increased risk for rapid relapse comprises determining the number and size of copy number variations (CNVs) in a sample from the patient and determining a large size ratio, where if the large size ratio is greater than or equal to about 0.02, the patient is deemed to be at an increased risk for rapid relapse. In certain embodiments, the large size ratio is calculated by dividing the number of CNVs that are larger in size than a cut-off value of about 400 or about 500 kb by the total number of CNVs.

In certain embodiments, a method of determining that a prostate cancer patient is at a decreased risk for relapse comprises determining the number and size of copy number variations (CNVs) in a sample from the patient and determining a large size ratio, where if the large size ratio is less than about 0.28, the patient is deemed to be at a decreased risk for relapse. In certain embodiments, the large size ratio is calculated by dividing the number of CNVs that are larger in size than a cut-off value of about 25 kb or about 30 kb by the total number of CNVs.

In certain embodiments, a method of determining that a prostate cancer patient is at a decreased risk for rapid relapse comprises determining the number and size of copy number variations (CNVs) in a sample from the patient and determining a large size ratio, where if the large size ratio is less than about 0.02, the patient is deemed to be at a decreased risk for rapid relapse. In certain embodiments, the large size ratio is calculated by dividing the number of CNVs that are larger in size than a cut-off value of about 400 or about 500 kb by the total number of CNVs.

In certain embodiments, methods of the present invention can further include determining the Gleason grade of the cancer, generating a nomogram and/or determining fusion gene status of the cancer. In certain embodiments, the fusion gene is selected from the group consisting of TRMT11-GRIK2, SLC45A2-AMACR, MTOR-TP53BP1, LRRC59-FLJ60017, TMEM135-CCDC67, KDM4B-AC011523.2, CCNH-C5orf30, MAN2A1-FER and combinations thereof.

The present invention further provides kits for determining whether a prostate cancer patient is at an increased risk for relapse and/or rapid relapse. In certain embodiments, the kit can include a means for analyzing the number and size of copy number variations (CNVs) in one or more genes. In certain embodiments, the means for analyzing the number and size of CNVs can comprise an array and/or microarray suitable for detecting the CNVs. In certain embodiments, the method can further include a software or internet access to software, in electronically readable form, that determines the number and size of CNVs in the one or more genes represented in the array and/or microarray. For example, and not by way of limitation, the software can (a) determine whether the CNVs exceed or fall below a size cut-off value and (b) determine the large size ratio. In certain embodiments, the large size ratio is calculated by dividing the number of CNVs that are larger in size than the cut-off value by the total number of CNVs. In certain embodiments, the kit can further comprise a means for detecting one or more fusion genes within a sample of the prostate cancer patient. In certain embodiments, the means for detecting the one or more fusion genes can include one or more fusion gene-specific probe and/or primer sets, arrays/microarrays or antibodies for detecting the one or more fusion genes. In certain embodiments, the one or more fusion genes are selected from the group consisting of TRMT11-GRIK2, SLC45A2-AMACR, MTOR-TP53BP1, LRRC59-FLJ60017, TMEM135-CCDC67, KDM4B-AC011523.2, CCNH-C5orf30, MAN2A1-FER and combinations thereof.

4. BRIEF DESCRIPTION OF THE FIGURES

Figure 1B:
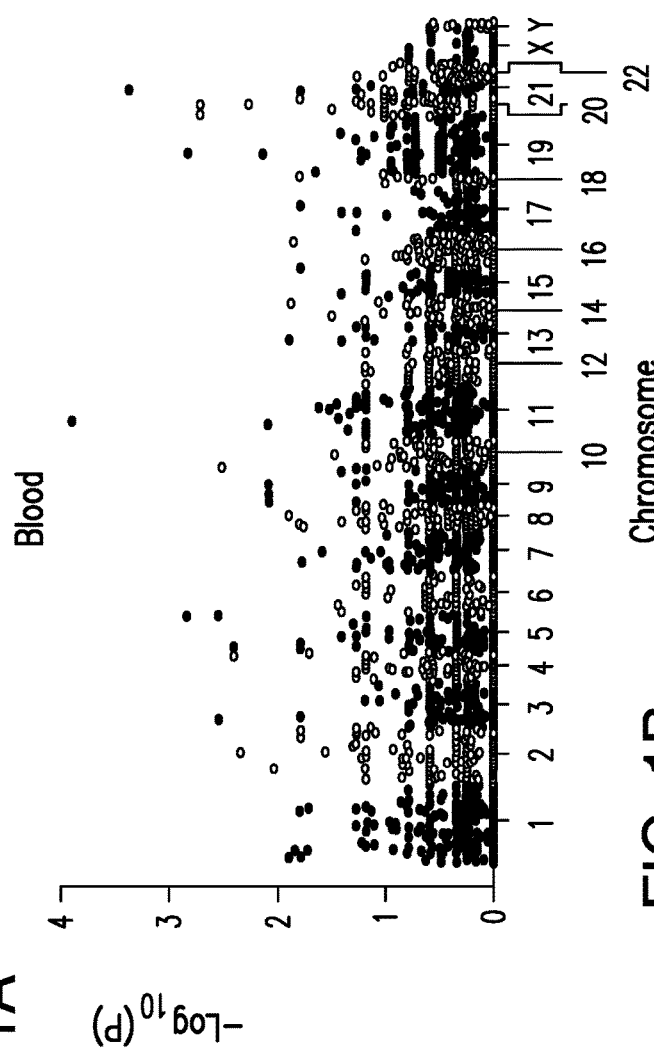

FIG. 1A-B. Copy number variations (CNV) in blood and prostate cancer from prostate cancer patients. FIG. 1A. Histogram of frequency of amplification (light gray) or deletion (dark gray) of genome sequences of leukocytes (upper panel, n=273) from prostate cancer patients. FIG. 1B. Manhattan plots of p-values in association with prostate cancer recurrence of each gene CNV from leukocytes.

FIG. 2A-C. Large size ratio (LSR) of CNVs from leukocytes from prostate cancer patients are correlated with aggressive behavior of prostate cancer. FIG. 2A. Schematic diagram of LSR model of leukocyte CNV. FIG. 2B. LSRs from leukocytes are associated with aggressive prostate cancer recurrence behavior. Upper panel: Correlation of LSRs from leukocyte genomes with prostate cancers that were recurrent; Lower panel: Correlation of LSRs from leukocyte genomes with prostate cancers that were non-recurrent 90 months after radical prostatectomy. FIG. 2C. LSRs from leukocytes are associated with short prostate specific antigen doubling time (PSADT). Upper panel: Correlation of LSRs from leukocyte genomes with prostate cancers that had recurrent serum PSADT of 4 months or less; Lower panel: Correlation of LSRs from leukocyte genomes with prostate cancers that were not recurrent or recurrent but having PSADT of 15 months or more.

Figure 3A:
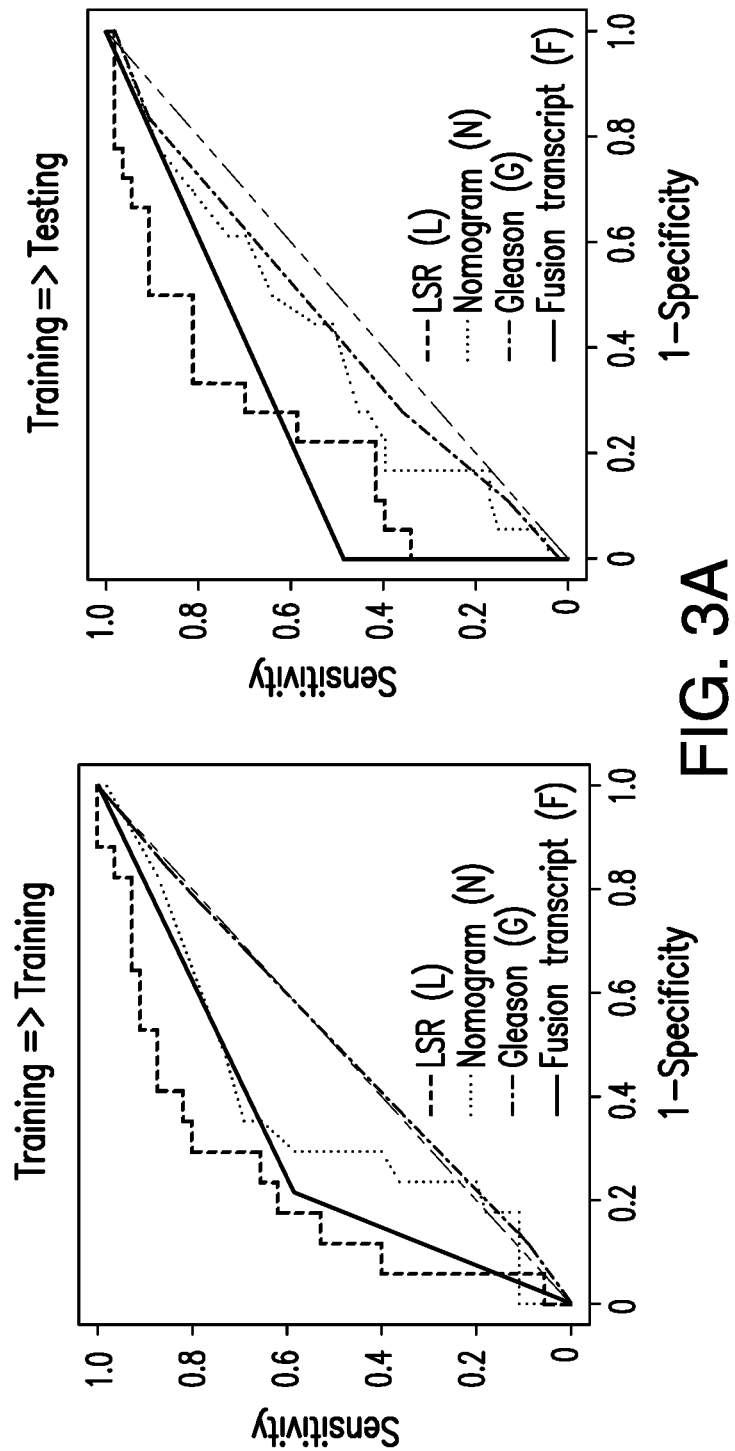
Figure 3B:
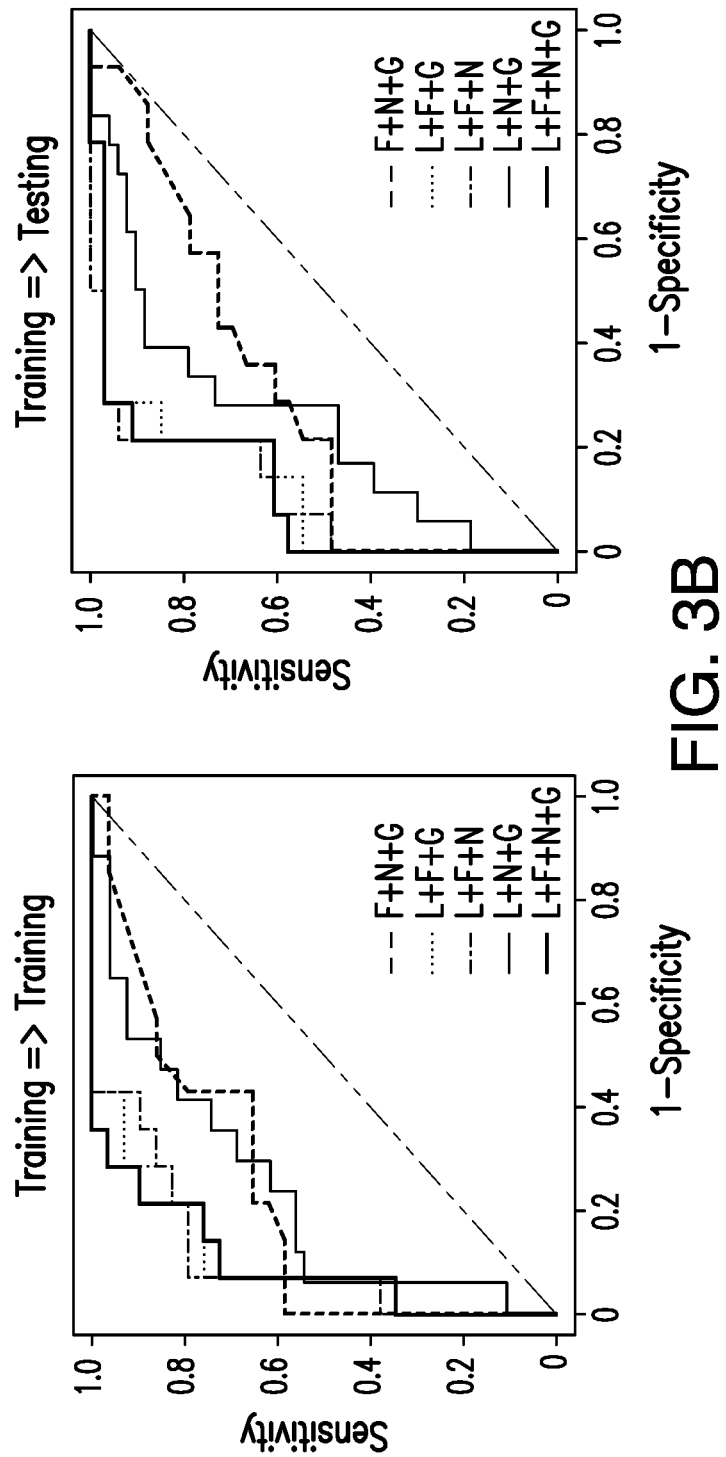

FIG. 3A-B. LSR of genome CNV from leukocytes to predict prostate cancer recurrence. FIG. 3A. LSR derived from leukocyte genome CNV predicts prostate cancer recurrence. Receiver operating curve (ROC) analyses using LSRs derived from leukocyte CNVs as prediction parameter (dark gray, dashed line) to predict prostate cancer recurrence, versus Nomogram (dotted line), Gleason's grade (dash-dotted line) and the status of 8 fusion transcripts (14) (light gray, dashed line). The samples were equally split randomly into training and testing sets 10 times. The ROC analysis represents the results from the most representative split. FIG. 3B. Combination of LSR (L), Gleason's grade (G), Nomogram (N) and the status of fusion transcripts (F) to predict prostate cancer recurrence. ROC analysis of a model combining LSR, fusion transcripts, Nomogram and Gleason's grade using linear discriminant analysis (LDA) is indicated by a black solid line. ROC analysis of a model combining fusion transcripts, Nomogram and Gleason's grade using LDA is indicated by a dark gray dashed line. ROC analysis of a model combining LSR, fusion transcripts and Gleason's grade using LDA is indicated by a dotted line. ROC analysis of a model combining LSR, fusion transcripts and Nomogram using LDA is indicated by a dash-dotted line. ROC analysis of a model combining LSR, Nomogram and Gleason's grade is indicated by a light gray dashed line. Similar random splits of training and testing data sets were performed as of (A).

Figure 4:
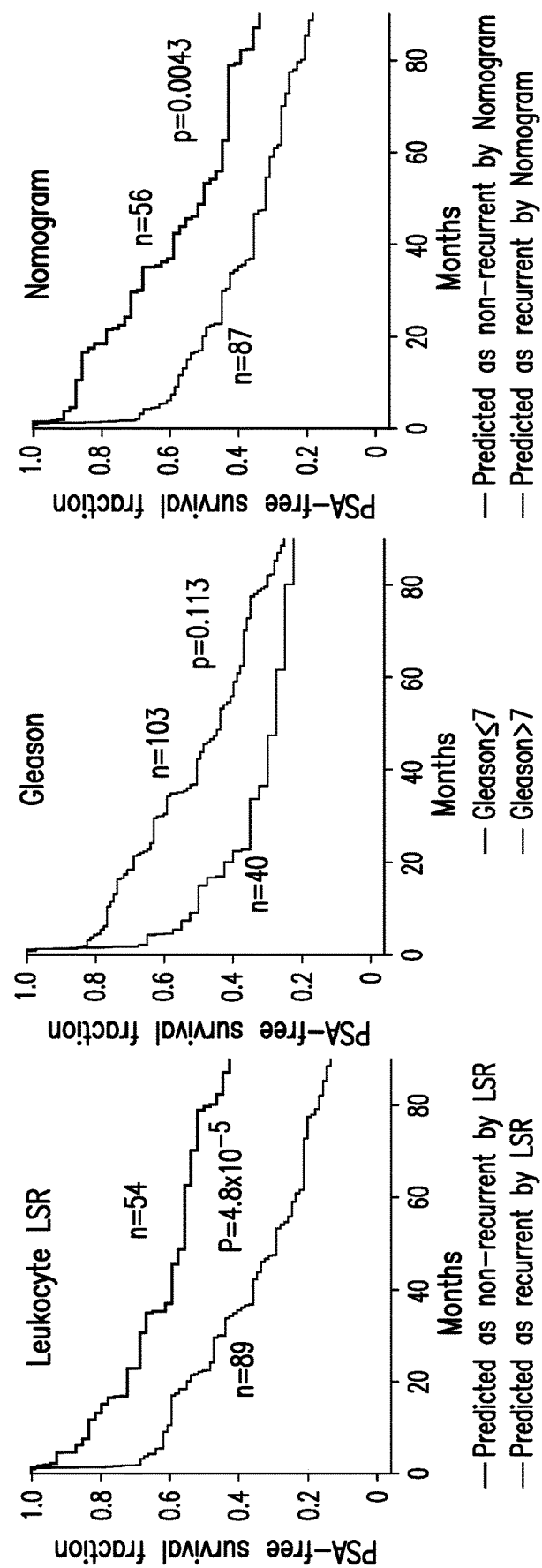
Figure 4:
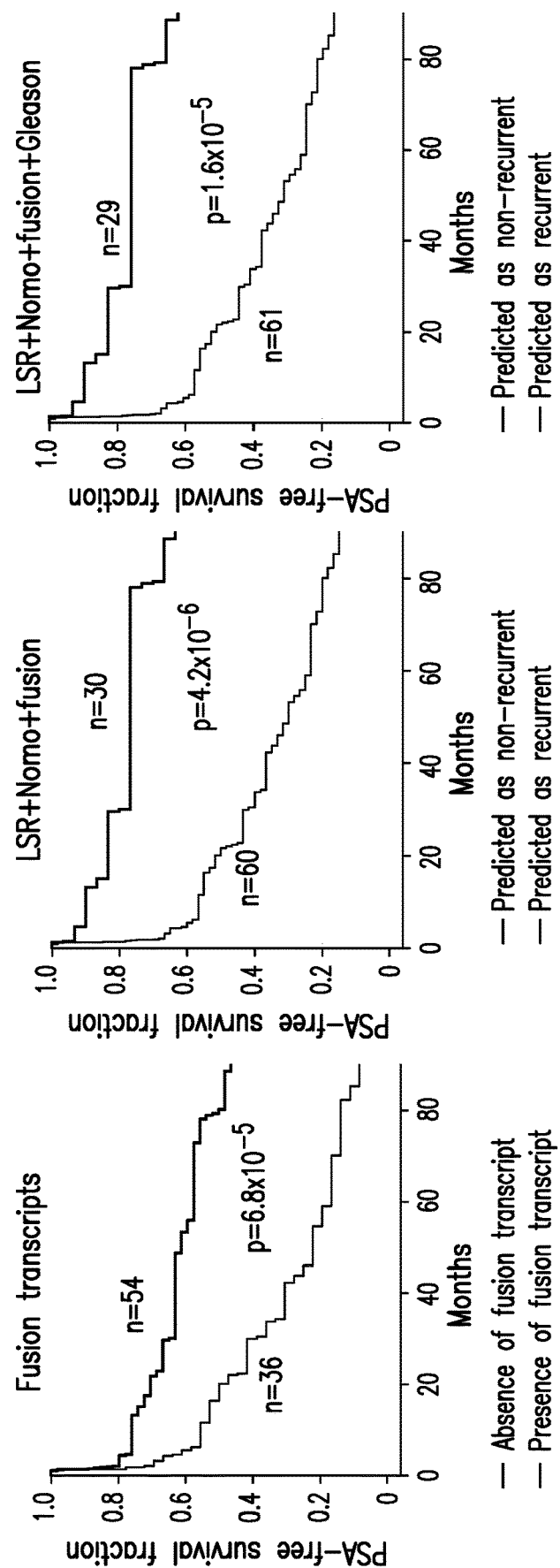

FIG. 4. Large LSRs of genome CNVs from leukocytes correlated with lower PSA-free survival. Kaplan-Meier analysis on patients predicted by LSR based on CNV of patients' leukocytes as likely recurrent versus likely non-recurrent (upper left). Similar survival analyses were also performed on case segregations based on Gleason's grades (upper middle), Nomogram probability (upper right), the status of 8 fusion transcripts (lower left), or a model by combining LSR, Nomogram and fusion transcript status using LDA (lower middle), or a model by combining LSR, Nomogram, Gleason grade and fusion transcript status using LDA (lower right). Number of samples analyzed and p values are indicated.

Figure 5A:
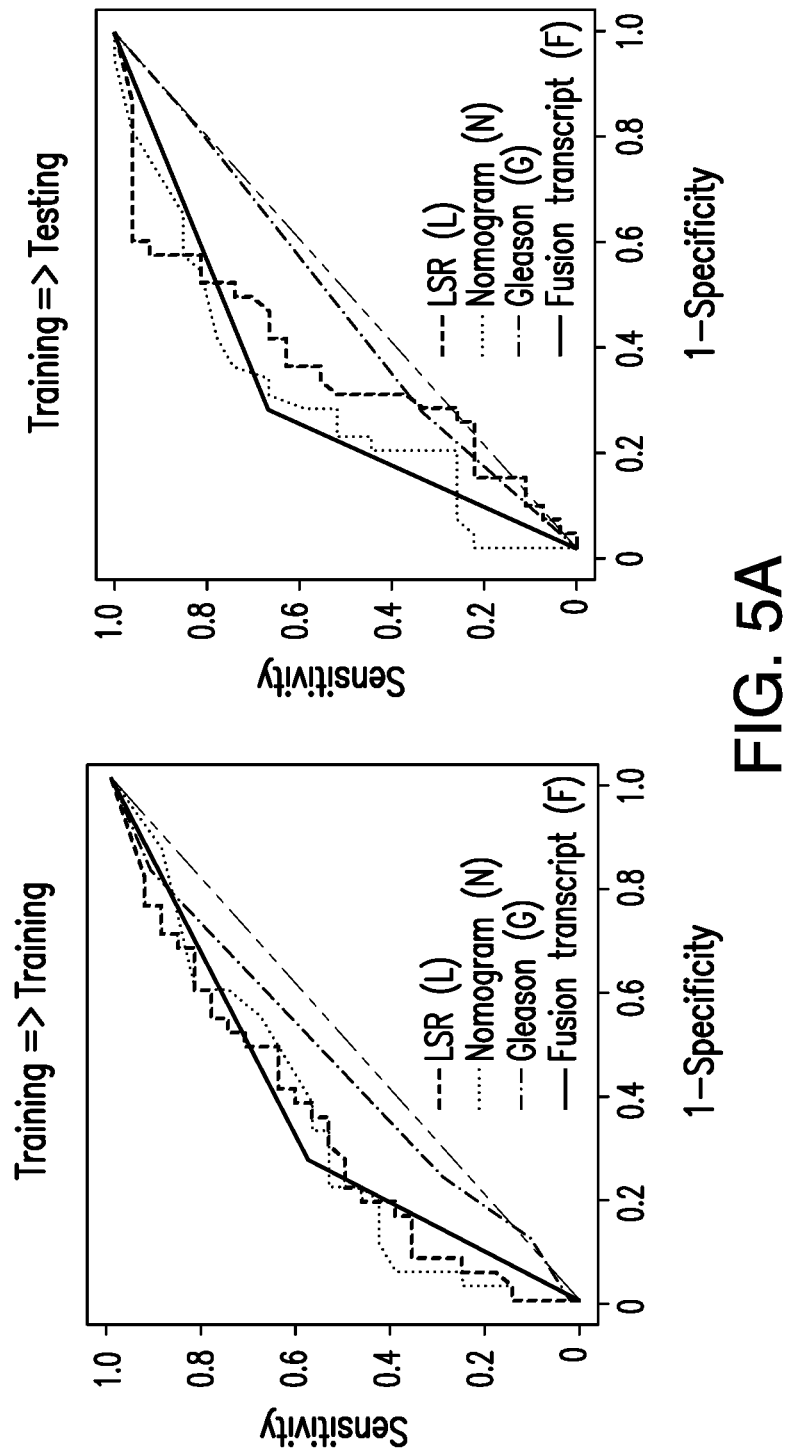
Figure 5B:
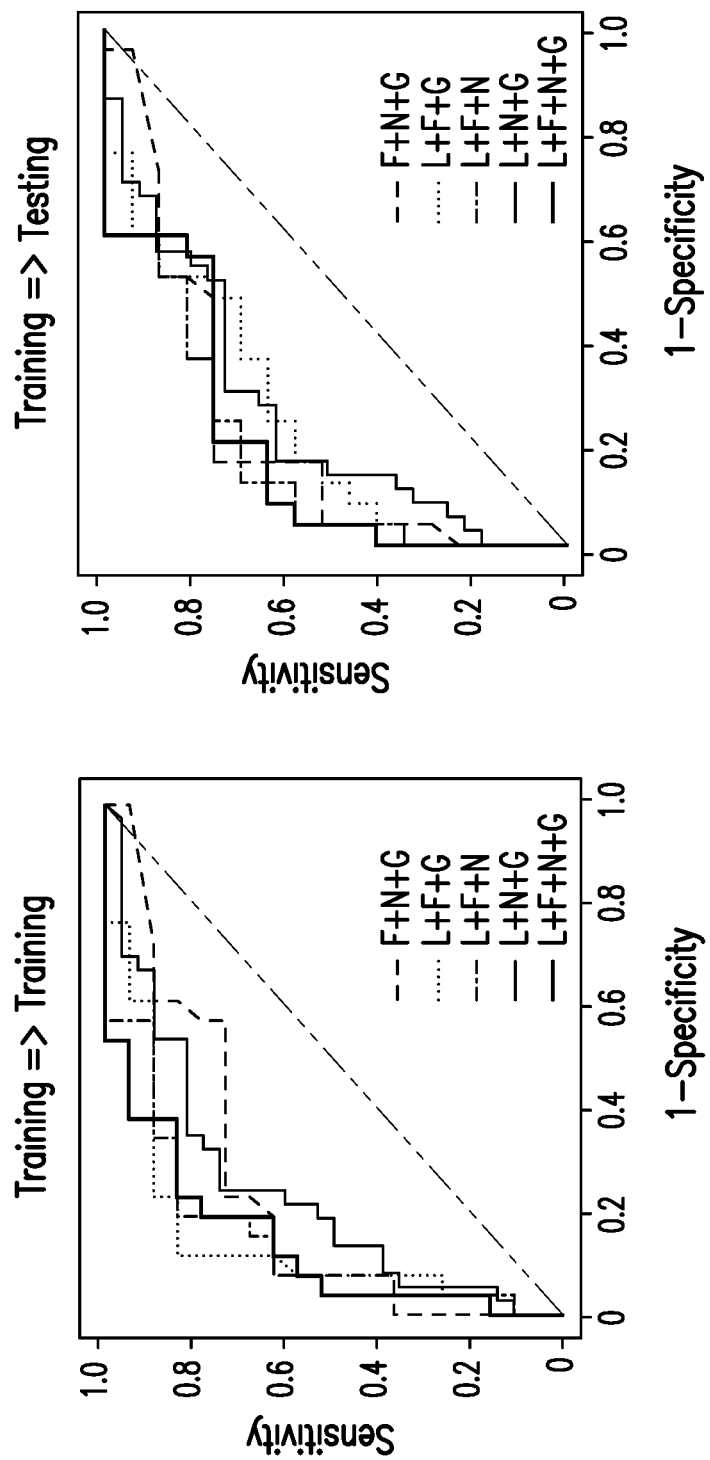

FIG. 5A-B. LSR of genome CNV from leukocytes to predict prostate cancer recurrence with short PSADT. LSR derived from leukocyte genome CNV predicts PSADT of 4 months or less. FIG. 5A. ROC analysis using LSRs derived from leukocyte CNVs as a prediction parameter (dark gray, dashed line) to predict PSADT 4 months or less, versus Nomogram (dotted line), Gleason's grade (dash-dotted line) and the status of 8 fusion transcripts (14) (light gray, dashed line). Samples were analyzed by the same procedure as FIG. 3. FIG. 5B. Combination of LSR (L), Gleason's grade (G), Nomogram (N) and the status of fusion transcripts (F) to predict prostate cancer recurrent PSADT 4 months or less. ROC analysis of a model combining LSR, fusion transcripts, Nomogram and Gleason's grade using LDA is indicated by a black solid line. ROC analysis of a model combining fusion transcripts, Nomogram and Gleason's grade using LDA is indicated by a dark gray dashed line. ROC analysis of a model combining LSR, fusion transcripts and Gleason's grade using LDA is indicated by a dotted line. ROC analysis of a model combining LSR, fusion transcripts and Nomogram using LDA is indicated by a dash-dotted line. ROC analysis of a model combining LSR, Nomogram and Gleason's grade is indicated by a light gray dashed line.

Figure 6:
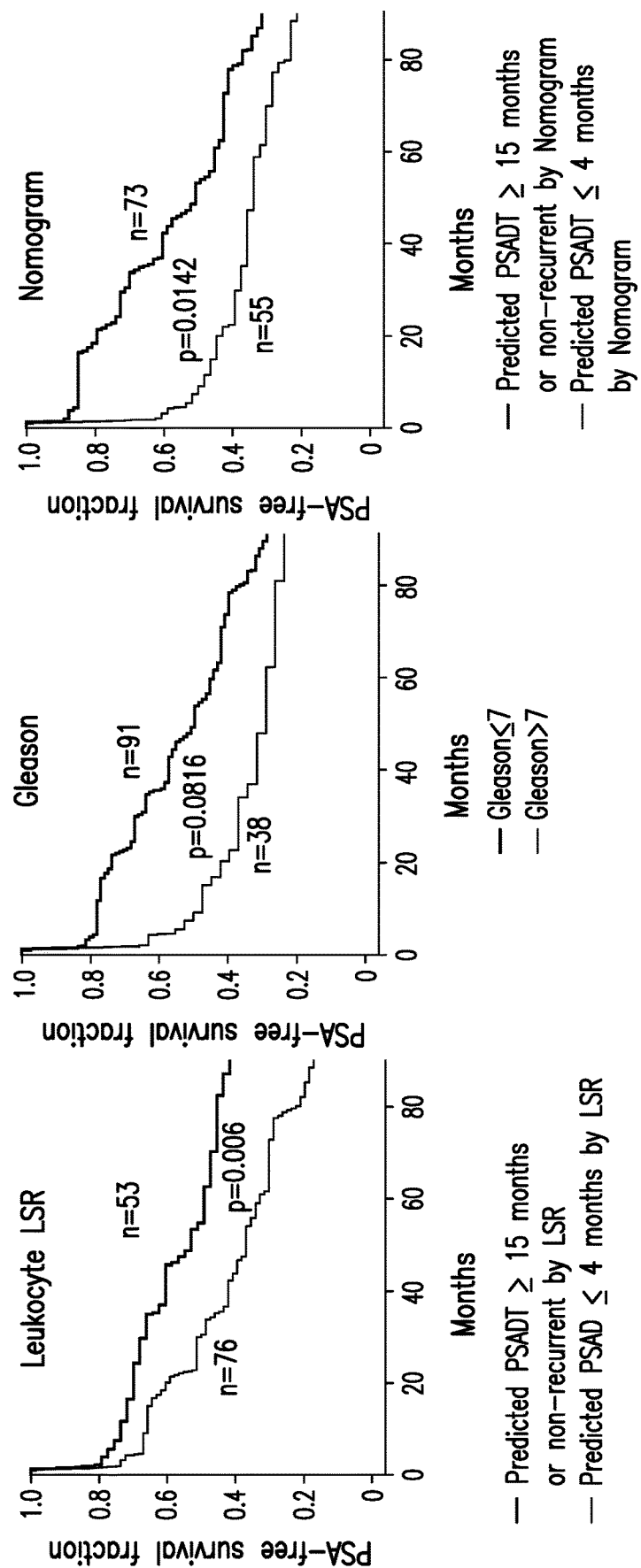
Figure 6:
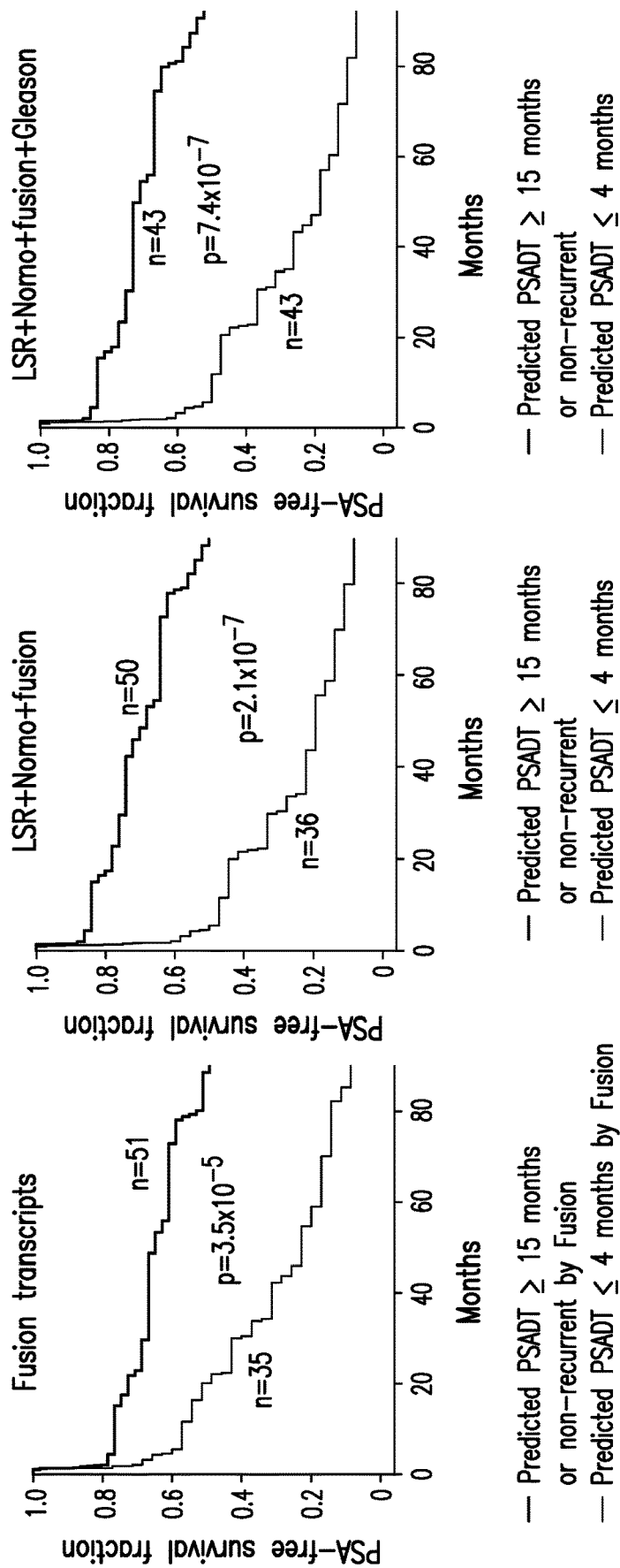

FIG. 6. Genome CNVs from leukocytes predicting short PSADT correlated with lower PSA-free survival. Kaplan-Meier analysis on patients predicted by LSR based on CNV of patients' leukocytes as likely recurrent and having PSADT 4 months or less versus likely non-recurrent or recurrent but having PSADT of 15 months or more (upper left). Similar survival analyses were also performed on case segregations based on Gleason's grades (upper middle), Nomogram probability (upper right), the status of 8 fusion transcripts (lower left), or a model by combining LSR, Nomogram and fusion transcript status using LDA (lower middle), or a model by combining LSR, Nomogram, Gleason grade and fusion transcript status using LDA (lower right). Number of samples analyzed and p values are indicated.

Figure 7:
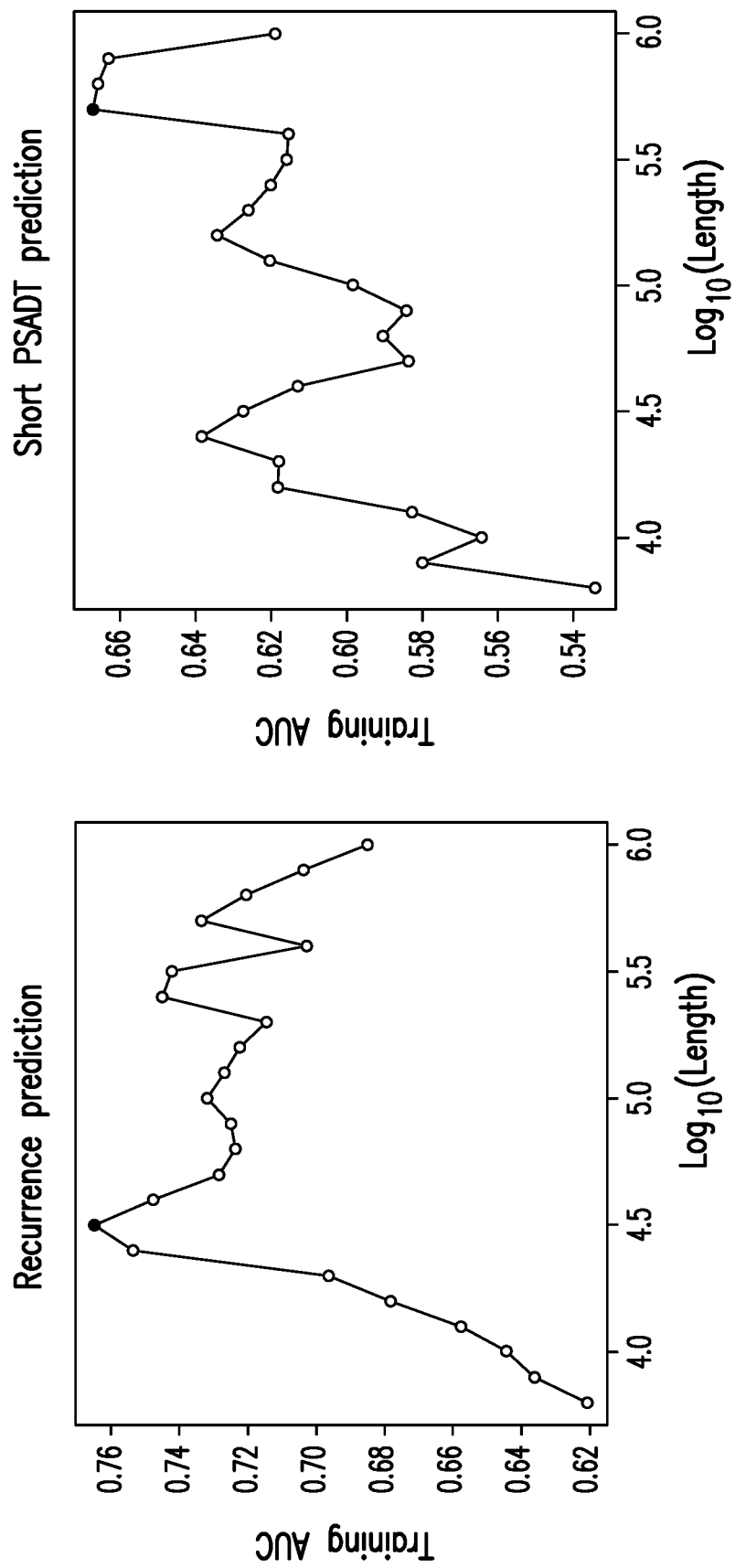

FIG. 7. Correlation of area under the curve (AUC) with LSR in predicting prostate cancer recurrence (left panel) or in predicting recurrent PSADT of ≤4 months (right panel).

Figure 8A:
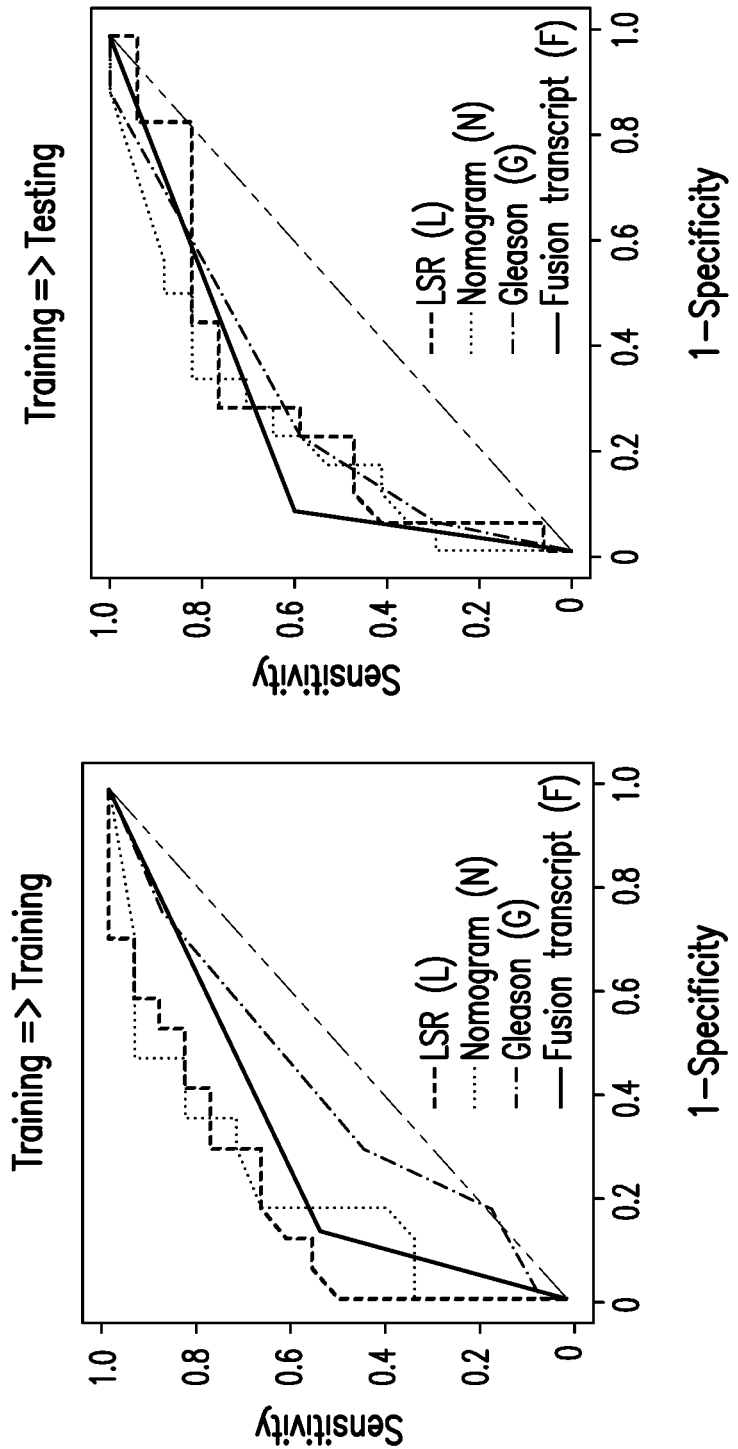
Figure 8B:
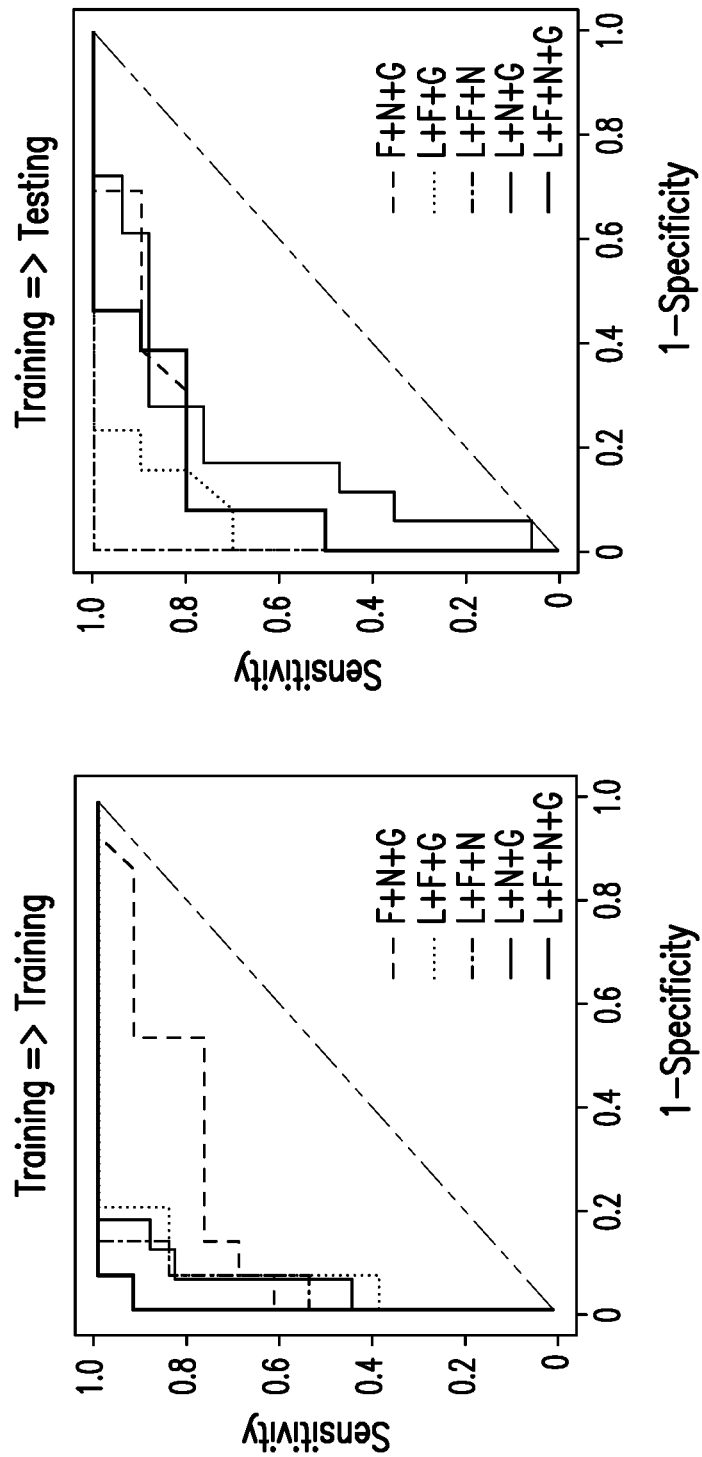

FIG. 8A-B. LSR of genome CNV from leukocytes to predict prostate cancer likely lethality. FIG. 8A. LSR derived from leukocyte genome CNV predicts prostate cancer likely lethality (recurrent within 12 months of radical prostatectomy and PSADT of ≤4 months). Receiver operating curve (ROC) analyses using LSRs derived from leukocyte CNVs as prediction parameter (dark gray, dashed line) to predict prostate cancer likely lethality, versus Nomogram (dotted line), Gleason's grade (dash-dotted line) and the status of 8 fusion transcripts (14) (light gray, dashed line). The samples were equally split randomly into training and testing sets 10 times. The ROC analysis represents the results from the most representative split. FIG. 8B. Combination of LSR (L), Gleason's grade (G), Nomogram (N) and the status of fusion transcripts (F) to predict prostate cancer likely lethality. ROC analysis of a model combining LSR, fusion transcripts, Nomogram and Gleason's grade using LDA is indicated by a black solid line. ROC analysis of a model combining fusion transcripts, Nomogram and Gleason's grade using LDA is indicated by a dark gray dashed line. ROC analysis of a model combining LSR, fusion transcripts and Gleason's grade using LDA is indicated by a dotted line. ROC analysis of a model combining LSR, fusion transcripts and Nomogram using LDA is indicated by a dash-dotted line. ROC analysis of a model combining LSR, Nomogram and Gleason's grade is indicated by a light gray dashed line. Similar random splits of training and testing data sets were performed as of (A).

Figure 9:
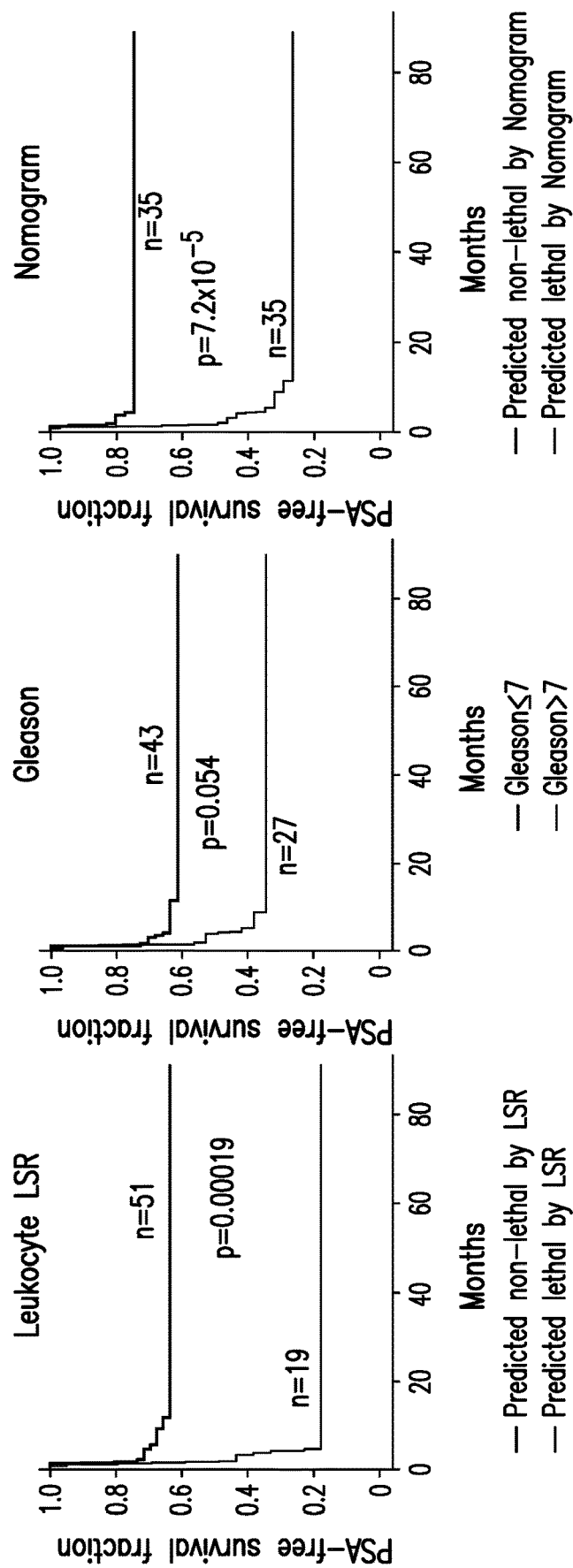
Figure 9:
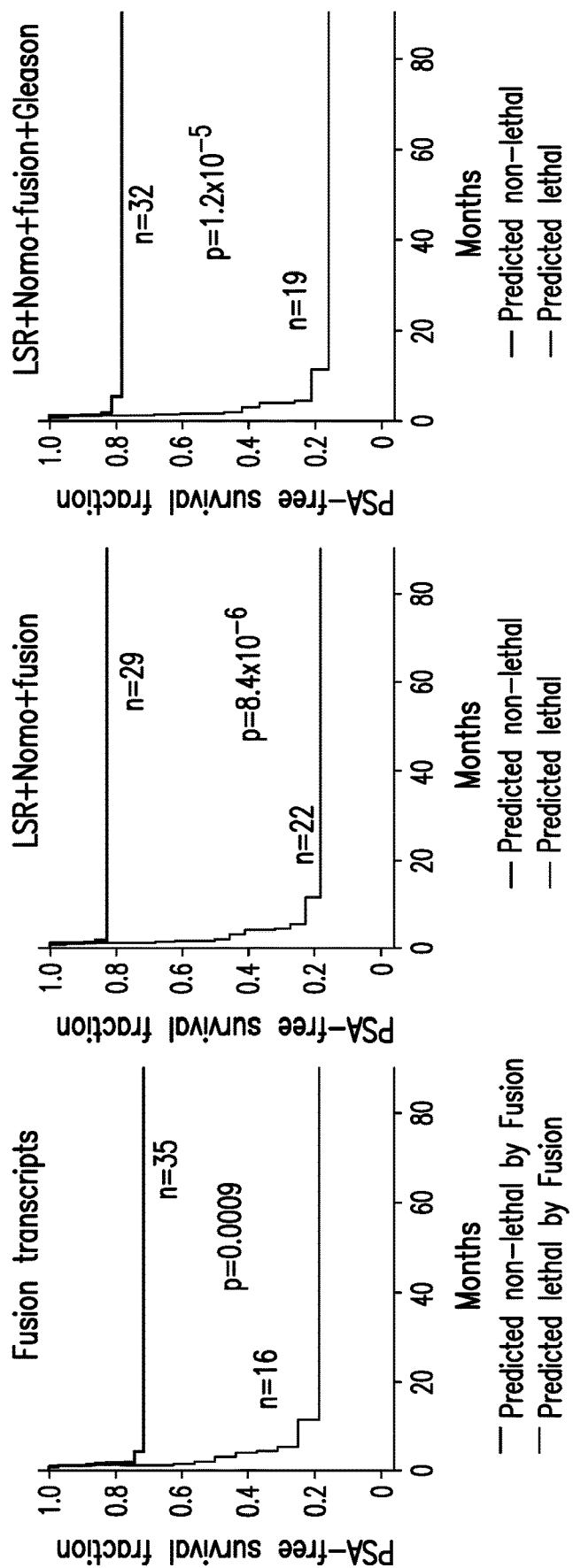

FIG. 9. Large LSRs of genome CNVs from leukocytes correlated with lower PSA-free survival. Kaplan-Meier analysis on patients predicted by LSR based on CNV of patients' leukocytes as likely lethal (recurrent within 12 months of radical prostatectomy and PSADT≤4 months) versus likely non-recurrent (upper left). Similar survival analyses were also performed on case segregations based on Gleason's grades (upper middle), Nomogram probability (upper right), the status of 8 fusion transcripts (lower left), or a model by combining LSR, Nomogram and fusion transcript status using LDA (lower middle), or a model by combining LSR, Nomogram, Gleason grade and fusion transcript status using LDA (lower right). Number of samples analyzed and p values are indicated.

5. DETAILED DESCRIPTION OF THE INVENTION

The present invention provides methods for assessing whether a subject having prostate cancer is at an increased risk of relapse and/or at an increased risk of rapid relapse. In certain embodiments, the present invention utilizes the size and number of the CNVs detected in a sample from the subject to assess the risk of relapse. The present invention further provides methods of treating subjects having an increased risk and/or decreased risk of relapse or rapid relapse.

For clarity of description, and not by way of limitation, the detailed description of the invention is divided into the following subsections:
  (i) definitions;
  (ii) methods of assessing risk of relapse or rapid relapse;
  (iii) methods of treatment;
  (iv) detection methods; and
  (v) kits.

5.1. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The terms "prostate cancer patient" or "subject having prostate cancer," as used interchangeably herein, refer to a subject having or who has had a carcinoma of the prostate. The use of the term "patient" does not suggest that the subject has received any treatment for the cancer, but rather that the subject has at some point come to the attention of the healthcare system. The patient/subject, prior to or contemporaneous with the practicing of the invention, may be untreated for prostate cancer, may have received treatment or are currently undergoing treatment, including but not limited to, surgical, chemotherapeutic, anti-androgen or radiologic treatment.

The term "sample," as used herein, includes, but is not limited to, cells in culture, cell supernatants, cell lysates, serum, blood plasma, biological fluid (e.g., blood, plasma, serum, stool, urine, lymphatic fluid, ascites, ductal lavage, saliva and cerebrospinal fluid) and tissue samples. The source of the sample may be solid tissue (e.g., from a fresh, frozen, and/or preserved organ, tissue sample, biopsy or aspirate), blood or any blood constituents, e.g., leukocytes, bodily fluids (such as, e.g., urine, lymph, cerebral spinal fluid, amniotic fluid, peritoneal fluid or interstitial fluid), or cells from the individual, including circulating cancer cells. In certain non-limiting embodiments, the sample is obtained from a prostate tumor. In certain embodiments, the sample may be a "biopsy sample" or "clinical sample," which are samples derived from a subject. In certain embodiments, the sample includes one or more prostate cancer cells from a subject. In certain embodiments, the sample is a blood sample, e.g., buffy coat sample, from a subject. In certain embodiments, the sample contains one or more leukocytes from a subject.

The term "relapse," as used herein, refers to a clinical course including one or more of the following: (i) where the cancer had been removed or put into remission, relapse refers to a recurrence of prostate cancer at the original site or occurrence at a new site, including metastatic spread; (ii) where the cancer had not been removed or put into remission, relapse refers to an extension of the cancer and/or metastatic spread; (iii) whether or not the cancer had been treated, relapse refers to an advancement in the clinical grade (for example, the Gleason grade), of the cancer; and/or a prostate specific antigen ("PSA") doubling time (PSADT) of 15 months.

The terms "rapid" or "relapse quickly," as used interchangeably herein, means that the relapse occurs within a period of 5 years. In certain embodiments, patients suffering a rapid relapse can also manifest a PSADT of 3 months or less or 4 months or less.

In certain non-limiting embodiments, "increased risk" means that a relapse or a rapid relapse occurs in more than about 50%, more than about 60%, more than about 70%, more than about 80% or more than 90% of individuals that have a large size ratio (LSR) greater than a particular threshold.

5.2 Methods of Assessing Risk of Relapse or Rapid Relapse

The present invention provides methods for determining whether a prostate cancer patient has an increased and/or decreased risk for relapse or rapid relapse.

In certain embodiments, the present invention utilizes the size and number of the CNVs to assess the likelihood that a prostate cancer will relapse or rapid relapse. For example, and not by way of limitation, the present invention can utilize the percentage of CNVs detected in a sample that are larger in size than a particular cut-off value to assess the likelihood that a prostate cancer will relapse or rapid relapse. In certain embodiments, the percentage of CNVs detected in a sample that are larger in size than a particular cut-off value can be represented by a large size ratio (see FIG. 2A). "Large size ratio," as used herein, refers to the ratio of CNVs that have a size larger than a cut-off value to the total number of CNVs detected in a sample of a subject. In certain embodiments, the large size ratio (LSR) can be represented by the following formula: LSR=large size number/total number of CNVs, where large size number is the number of CNVs that are larger in size than a cut-off value.

In certain embodiments, the cut-off value for determining the LSR for a subject can be about 20 kilobases (kb), about 25 kb, about 30 kb, about 31 kb, about 32 kb, about 33 kb, about 34 kb, about 35 kb, about 40 kb, about 45 kb, about 50 kb, about 55 kb, about 60 kb, about 65 kb, about 70 kb, about 75 kb, about 80 kb, about 85 kb, about 90 kb, about 95 kb, about 100 kb, about 150 kb, about 200 kb, about 250 kb, about 300 kb, about 350 kb, about 400 kb, about 450 kb, about 500 kb, about 501 kb or about 550 kb. In certain embodiments, the cut-off value can be about 31,622 base pairs (bp) or about 501,187 bp.

In certain embodiments, in methods for determining that a prostate cancer patient is at increased and/or decreased risk for relapse, the LSR can be calculated by dividing the number of CNVs that are larger than about 25 kb or about 30 kb in size by the total number of CNVs (e.g., LSR= (number of CNVs larger than about 25 kb or about 30 kb in size)/total number of CNVs).

In certain embodiments, in methods for determining that a prostate cancer patient is at an increased and/or decreased risk for rapid relapse, the LSR can be calculated by dividing the number of CNVs that are larger than about 400 kb or about 500 kb in size by the total number of CNVs (e.g., LSR=(number of CNVs larger than about 400 kb or about 500 kb in size)/total number of CNVs).

In certain embodiments, CNVs across the genome can be determined and used to determine the LSR. CNVs can be detected using methodology known in the art, including hybridization to gene arrays and the analysis of the results of such hybridization using software that determines copy number variation, as disclosed herein. In certain embodiments, CNV size can be determined using the same genotyping analysis techniques as described below and as are known in the art. In certain embodiments of the invention, using the Partek software described below, segments with changes in copy number can be obtained (including amplification and deletions), and those with the following criteria: p<0.001, length >2 kb and >10 markers can be selected. The length of the selected CNVs can also be determined.

The presently disclosed subject matter provides methods for determining whether a prostate cancer patient is at an increased risk for relapse or rapid relapse. In certain embodiments, the method comprises determining the number and size of CNVs in a sample and determining the large size ratio, where if the large size ratio exceeds a particular threshold, the patient is deemed to be at an increased risk for relapse or rapid relapse. In certain embodiments, the sample can be a blood sample from the patient, e.g., a buffy coat sample. In certain embodiments, the sample can comprise one or more leukocytes from the patient.

In certain embodiments, a large size ratio of about 0.28 or greater is consistent with a likelihood that the prostate cancer will relapse, e.g., when the cut-off value for calculating the large size ratio is about 25 kb or about 30 kb. Accordingly, the present invention provides for a method of determining that a prostate cancer patient is at an increased risk for relapse comprising determining the number and size of CNVs in a sample of the patient and determining the large size ratio, where if the large size ratio is about 0.28 or greater, the patient is deemed to be at an increased risk for relapse.

In certain embodiments, a large size ratio of about 0.02 or greater is consistent with a likelihood that the prostate cancer will rapidly relapse, e.g., when the cut-off value for calculating the large size ratio is about 500 kb. In certain embodiments, a large size ratio between about 0.02 and about 0.28 can indicate that the prostate cancer will rapidly relapse. Accordingly, the present invention provides for a method of determining that a prostate cancer patient is at an increased risk for relapse comprising determining the number and size of CNVs in a sample of the patient and determining the large size ratio, where if the large size ratio is about 0.02 or greater, the patient is deemed to be at an increased risk for rapid relapse.

The presently disclosed subject matter further provides methods for determining whether a prostate cancer patient is at a decreased risk for relapse or rapid relapse. In certain embodiments, the method comprises determining the number and size of CNVs in a sample and determining the large size ratio, where if the large size ratio is less than a particular threshold, the patient is deemed to be at a decreased risk for relapse or rapid relapse.

In certain embodiments, a large size ratio of less than about 0.28 is consistent with a likelihood that the prostate cancer will be at a decreased risk of relapse, e.g., when the cut-off value for calculating the large size ratio is about 25 kb or about 30 kb. In certain embodiments, a large size ratio between about 0.02 and about 0.28 can indicate that the prostate cancer will be at a decreased risk of relapse. Accordingly, the present invention provides for a method of determining that a prostate cancer patient is at a decreased risk for relapse comprising determining the number and size of CNVs in a sample of the patient and determining the large size ratio, where if the large size ratio is less than about 0.28, the patient is deemed to be at a decreased risk for relapse.

In certain embodiments, a large size ratio of less than about 0.02 is consistent with a likelihood that the prostate cancer will be at a decreased risk of rapid relapse, e.g., when the cut-off value for calculating the large size ratio is about 400 kb or about 500 kb. Accordingly, the present invention provides for a method of determining that a prostate cancer patient is at a decreased risk for relapse comprising determining the number and size of CNVs in a sample of the patient and determining the large size ratio, where if the large size ratio is less than about 0.02, the patient is deemed to be at a decreased risk for rapid relapse.

In certain embodiments, the method can further include determining one or more of the following: the Gleason grade of the prostate cancer, nomogram and fusion gene status. For example, and not by way of limitation, the method of determining whether a subject is at increased risk or decreased risk of relapse or rapid relapse of prostate cancer can further comprise determining the Gleason grade of a prostate cancer sample from a subject.

In certain embodiments, the method of determining whether a subject is at increased risk or decreased risk of relapse or rapid relapse of prostate cancer can further comprise generating a nomogram. In certain embodiments, the nomogram can be determined using the prediction tool available at www.mskcc.org/nomograms/prostate.

In certain embodiments, the method of determining whether a subject is at increased risk or decreased risk of relapse or rapid relapse of prostate cancer can further comprise determining whether a sample of the subject contains one or more fusion genes. The term "fusion gene," as used herein, refers to a nucleic acid or protein sequence, which combines elements of the recited genes or their RNA transcripts in a manner not found in the wild type/normal nucleic acid or protein sequences. For example, but not by way of limitation, in a fusion gene in the form of genomic DNA, the relative positions of portions of the genomic sequences of the recited genes is altered relative to the wild type/normal sequence (for example, as reflected in the NCBI chromosomal positions or sequences set forth herein). In a fusion gene in the form of mRNA, portions of RNA transcripts arising from both component genes are present (not necessarily in the same register as the wild-type transcript and possibly including portions normally not present in the normal mature transcript). In non-limiting embodiments, such a portion of genomic DNA or mRNA may comprise at least about 10 consecutive nucleotides, or at least about 20 consecutive nucleotides, or at least about 30 consecutive nucleotides, or at least 40 consecutive nucleotides. In a fusion gene in the form of a protein, portions of amino acid sequences arising from both component genes are present (not by way of limitation, at least about 5 consecutive amino acids or at least about 10 amino acids or at least about 20 amino acids or at least about 30 amino acids). In certain embodiments, portions arising from both genes, transcripts or proteins do not refer to sequences which may happen to be identical in the wild type forms of both genes (that is to say, the portions are "unshared"). As such, a fusion gene represents, generally speaking, the splicing together or fusion of genomic elements not normally joined together. Non-limiting examples of such fusion genes include TRMT11-GRIK2, SLC45A2-AMACR, MTOR-TP53BP1, LRRC59-FLJ60017, TMEM135-CCDC67, KDM4B-AC011523.2, CCNH-C5orf30 and MAN2A1-FER.

The fusion gene TRMT11-GRIK2 refers to a fusion between the tRNA methyltransferase 11 homolog ("TRMT11") and glutamate receptor, ionotropic, kainate 2 ("GRIK2") genes. The human TRMT11 gene is typically located on chromosome 6q11.1 and the human GRIK2 gene is typically located on chromosome 6q16.3. In certain embodiments, the TRMT11 gene is the human gene having NCBI Gene ID No: 60487, sequence chromosome 6; NC_000006.11 (126307576 . . . 126360422) and/or the GRIK2 gene is the human gene having NCBI Gene ID No:2898, sequence chromosome 6; NC_000006.11 (101841584 . . . 102517958).

The fusion gene SLC45A2-AMACR refers to a fusion between the solute carrier family 45, member 2 ("SLC45A2") and alpha-methylacyl-CoA racemase ("AMACR") genes. The human SLC45A2 gene is typically located on human chromosome 5p13.2 and the human AMACR gene is typically located on chromosome 5p13. In certain embodiments, the SLC45A2 gene is the human gene having NCBI Gene ID No: 51151, sequence chromosome 5; NC_000005.9 (33944721 . . . 33984780, complement) and/or the AMACR gene is the human gene having NCBI Gene ID No:23600, sequence chromosome 5; NC_000005.9 (33987091 . . . 34008220, complement).

The fusion gene MTOR-TP53BP1 refers to a fusion between the mechanistic target of rapamycin ("MTOR") and tumor protein p53 binding protein 1 ("TP53BP1") genes. The human MTOR gene is typically located on chromosome 1p36.2 and the human TP53BP1 gene is typically located on chromosome 15q15-q21. In certain embodiments, the MTOR gene is the human gene having NCBI Gene ID No:2475, sequence chromosome 1 NC_000001.10 (11166588 . . . 11322614, complement) and/or the TP53BP1 gene is the human gene having NCBI Gene ID No: 7158, sequence chromosome 15; NC_000015.9 (43695262 . . . 43802707, complement).

The fusion gene LRRC59-FLJ60017 refers to a fusion between the leucine rich repeat containing 59 ("LRRC59") gene and the "FLJ60017" nucleic acid. The human LRRC59 gene is typically located on chromosome 17q21.33 and nucleic acid encoding human FLJ60017 is typically located on chromosome 11q12.3. In certain embodiments, the LRRC59 gene is the human gene having NCBI Gene ID No:55379, sequence chromosome 17; NC_000017.10 (48458594 . . . 48474914, complement) and/or FLJ60017 has a nucleic acid sequence as set forth in GeneBank AK_296299.

The fusion gene TMEM135-CCDC67 refers to a fusion between the transmembrane protein 135 ("TMEM135") and coiled-coil domain containing 67 ("CCDC67") genes. The human TMEM135 gene is typically located on chromosome 11q14.2 and the human CCDC67 gene is typically located on chromosome 11q21. In certain embodiments, the TMEM135 gene is the human gene having NCBI Gene ID No: 65084, sequence chromosome 11; NC_000011.9 (86748886 . . . 87039876) and/or the CCDC67 gene is the human gene having NCBI Gene ID No: 159989, sequence chromosome 11; NC_000011.9 (93063156 . . . 93171636).

The fusion gene CCNH-C5orf30 refers to a fusion between the cyclin H ("CCNH") and chromosome 5 open reading frame 30 ("C5orf30") genes. The human CCNH gene is typically located on chromosome 5q13.3-q14 and the human C5orf30 gene is typically located on chromosome 5q21.1. In certain embodiments, the CCNH gene is the human gene having NCBI Gene ID No: 902, sequence chromosome 5; NC_000005.9 (86687310 . . . 86708850, complement) and/or the C5orf30 gene is the human gene having NCBI Gene ID No: 90355, sequence chromosome 5; NC_000005.9 (102594442 . . . 102614361).

The fusion gene KDM4B-AC011523.2 refers to a fusion between lysine (K)-specific demethylase 4B ("KDM4B") and chromosomal region "AC011523.2." The human KDM4B gene is typically located on chromosome 19p13.3 and the human AC011523.2 region is typically located on chromosome 19q13.4. In certain embodiments, the KDM4B gene is the human gene having NCBI Gene ID NO: 23030, sequence chromosome 19; NC_000019.9 (4969123 . . . 5153609).

The fusion gene MAN2A1-FER refers to a fusion between mannosidase, alpha, class 2A, member 1 ("MAN2A1") and (fps/fes related) tyrosine kinase ("FER"). The human MAN2A1 gene is typically located on chromosome 5q21.3 and the human FER gene is typically located on chromosome 5q21. In certain embodiments, the MAN2A1 gene is the human gene having NCBI Gene ID NO: 4124, sequence chromosome 5; NC_000005.9 (109025156 . . . 109203429) or NC_000005.9 (109034137 . . . 109035578); and/or the FER gene is the human gene having NCBI Gene ID NO: 2241, sequence chromosome 5: NC_000005.9 (108083523 . . . 108523373).

In certain embodiments, to predict prostate cancer relapse by the combination of the LSR, Nomogram, fusion gene status and Gleason grading, it is postulated that samples from relapse or non-relapse groups follow normal distribution with different means but same covariance matrix. For example, and not by limitation, based on training data, the mean value for relapse samples is mu_relapse=(0.462 0.8714 0.571 7.107) for (LSR, Nomogram, fusion, Gleason) and the mean for non-relapse samples is mu_non-relapse= (0.318 0.907 0.214 7.214). In certain embodiments, the pooled covariance matrix can be represented as follows:

|  | LSR | sigma = nomogram | fusion | gleason |
| --- | --- | --- | --- | --- |
| LSR | 8.491034e−03 | 8.507772e−05 | 0.004008907 | −0.012312703 |
| nomo | 8.507772e−05 | 1.307571e−02 | −0.002607143 | −0.063142857 |
| fusion | 4.008907e−03 | −2.607143e−03 | 0.230357143 | −0.008928571 |
| gleason | −1.231270e−02 | −6.314286e−02 | −0.008928571 | 0.525892857 |

In certain embodiments, for a testing sample x=[x1,x2, x3,x4]', its posterior probability can be estimated by the following:

$p(\text{relapse}|x)=p\_0(x)*p(\text{relapse})/(p\_0(x)*p(\text{relapse})+p\_1(x)*p(\text{non\_relapse}))$ $p(\text{non-relapse}|x)=p\_1(x)*p(\text{non\_relapse})/(p\_0(x)*p(\text{relapse})+p\_1(x)*p(\text{non\_relapse}))$ In certain embodiments, the cut-off value of the posterior probability can be set to be a suitable value to increase or maximize the Youden index, which can be, for example and without limitation and as embodied herein, about 0.544. In certain embodiments, a testing sample with a posterior probability that is greater than about 0.5, greater than about 0.54 or greater than about 0.544 can be predicted to be relapse, or otherwise the testing sample can be predicted to be non-relapse.

In certain embodiments, the techniques described above can be applied to classify fast relapse versus non-fast relapse. For example, and not by limitation, the mean values for the fast relapse group is mu_fast-relapse=(0.031 0.828 0.667 7.267) for (LSR, Nomogram, fusion, Gleason) and the mean for the non-fast relapse samples is mu_non-fast relapse=(0.023 0.905 0.269 7.192). In certain embodiments, the pooled covariance matrix can be represented as follows:

|  | LSR | sigma = nomogram | fusion | gleason |
|---|---|---|---|---|
| LSR | 0.0007088535 | 0.0001202635 | 0.0006518215 | 0.0003571929 |
| nomo | 0.0001202635 | 0.0125151282 | 0.0129487179 | −0.0740256410 |
| fusion | 0.0006518215 | 0.0129487179 | 0.2166337936 | −0.1028928337 |
| gleason | 0.0003571929 | −0.0740256410 | −0.1028928337 | 0.6915844839 |

In certain embodiments, the cut-off value of the posterior probability can be set to about 0.396. For example, and not by way of limitation, a testing sample with a posterior probability greater than about 0.35, greater than about 0.39 or greater than about 0.396 can be predicted to be fast relapse, or otherwise the testing sample can be predicted to be non-fast relapse.

5.3. Methods of Treatment

In certain embodiments, use of the present invention can inform a health care practitioner how to better advise a prostate cancer patient on whether or not to undergo more aggressive forms of therapy or whether watchful waiting would be an appropriate recommendation. Accordingly, the present invention provides methods for treating prostate cancer patients that are at an increased and/or decreased risk for relapse or rapid relapse.

In certain embodiments, if it is determined that the patient is at an increased risk for relapse or rapid relapse, as disclosed herein, a healthcare provider can take the further step of recommending and/or performing a prophylactic and/or treatment regimen. For example, and not by way of limitation, one or more of the following can be recommended and/or performed: cryotherapy, radiation therapy, chemotherapy, hormone therapy, biologic therapy, bisphosphonate therapy, high-intensity focused ultrasound, frequent monitoring, frequent prostate-specific antigen (PSA) checks and radical prostatectomy.

In certain embodiments, if it is determined that the patient is not at an increased risk and/or is at a decreased risk for relapse or rapid relapse, as disclosed herein, a healthcare provider can recommend and/or perform one or more of the following: high-intensity focused ultrasound, watchful waiting, frequent monitoring, frequent PSA checks and a biopsy.

In certain embodiments, one or more of the prophylactic and/or treatment regimens, disclosed herein, can be performed at about 1 month, about 2 months, about 3 months, about 4 months, about 5 months, about 6 months, about 7 months, about 8 months, about 9 months, about 10 months, about 11 months, about 12 months, about 18 months, about 2 years, about 3 years, about 4 years or about 5 years following the assessment of the risk of relapse or rapid relapse for the prostate cancer patient.

A non-limiting example of a biologic therapeutic is Sipuleucel-T. Bisphosphonate therapy includes, but is not limited to, clodronate or zoledronate. Hormone therapy can include one or more of orchiectomy and the administration of luteinizing hormone-releasing hormone (LHRH) analogs and/or agonists, LHRH antagonists, anti-androgens or androgen-suppressing drugs. Non-limiting examples of LHRH analogs and/or agonists include leuprolide, goserelin and buserelin. Non-limiting examples of LHRH antagonists include abarelix, cetrorelix, ganirelix and degarelix. Anti-androgen drugs include, but are not limited to, flutamide, bicalutamide, enzalutamide and nilutamide. Non-limiting examples of androgen-suppressing drugs include estrogens, ketoconazole and aminoglutethimide. Frequent monitoring can include PSA blood tests, digital rectal exams, ultrasounds and/or transrectal ultrasound-guided prostate biopsies at regular intervals, e.g., at about 3 to about 6 month intervals, to monitor the status of the prostate cancer. Radical prostatectomy is a surgical procedure that involves the removal of the entire prostate gland and some surrounding tissue. Prostatectomies can be performed by open surgery or it may be performed by laparoscopic surgery.

In certain embodiments, these prophylactic and/or treatment regimens can be used to produce an anti-cancer effect in a subject. For example, and not by way of limitation, the present invention provides methods of treating a prostate cancer patient to produce an anti-cancer effect in the patient. An "anti-cancer effect" refers to one or more of a reduction in aggregate cancer cell mass, a reduction in cancer cell growth rate, a reduction in cancer progression, a reduction in cancer cell proliferation, a reduction in tumor mass, a reduction in tumor volume, a reduction in tumor cell proliferation, a reduction in tumor growth rate and/or a reduction in tumor metastasis. In certain embodiments, an anti-cancer effect can refer to a complete response, a partial response, a stable disease (without progression or relapse), a response with a later relapse or progression-free survival in a patient diagnosed with cancer.

5.4. Detection Methods

The present invention provides methods for detecting the number and size of CNVs across the genome of a subject. The present invention further provides methods for detecting the presence of one or more fusion genes, disclosed herein, within a sample of a subject.

5.4.1 Copy Number Variation Detection

The present invention provides methods for determining the size and number of CNVs within a sample of a subject. In certain embodiments, CNVs can be detected in one or more samples of a subject. For example, and not by way of limitation, the sample can be a sample of malignant tumor (or presumptively malignant tumor, where a diagnosis has not yet been made) tissue. In certain embodiments, microdissection can be performed to achieve a tumor purity of at least about 70% or at least about 80% or greater than 80%. In certain embodiments, the sample can be tissue adjacent to a malignant tumor tissue (e.g., prostate tissue that is not identified as a tumor located in a prostate gland that contains a tumor). In certain embodiments, a sample can be a tissue sample which is considered by a skilled artisan to appear abnormal (microscopically and/or macroscopically) and is to be tested to determine whether it is cancerous. In certain embodiments, a sample can be a blood sample that contains at least some nucleated cells to serve as a source of DNA, e.g., a whole blood or buffy coat blood sample. In certain embodiments, the sample can comprise one or more leukocytes from the subject. In certain embodiments, multiple samples can be prepared for a single subject. For example, but not by way of limitation, samples of tumor (i.e., malignant) tissue, tissue adjacent to a tumor tissue and blood can be prepared and each of the samples can be analyzed for CNVs and compared.

In certain embodiments, DNA can be extracted from the sample, e.g., using a Qiagen kit or other method known in the art. In certain embodiments, genotyping of the extracted DNA can be performed to identify CNVs across the genome or a portion of the genome. For example, and not by way of limitation, genotyping can be performed by fragmenting the DNA using restriction enzymes (e.g., Sty1 and/or Nsp1), ligating the DNA fragments to adaptors, amplifying the adaptor-DNA fragments using primers that correspond to the adaptor sequences and, optionally, performing an additional fragmentation step (e.g., by digestion with DNaseI). In certain embodiments, the genotyping technique can further include labeling the amplified (or optionally further fragmented) DNA product (e.g., with biotinylated nucleotides) and then hybridizing the resulting labeled DNA to a plurality of test nucleic acid, e.g., DNA, molecules representative of the genome or a genome portion of interest under appropriate conditions (for example, as described by the array manufacturer). Additional non-limiting examples of genotyping techniques are disclosed in International Application No. WO 2013/106737, the contents of which are hereby incorporated by reference in its entirety. In certain embodiments, the plurality of test nucleic acid molecules can be provided in an array such as, but not limited to, the Affymetrix Genomewide Human SNP Array 6.0 (Affymetrix, CA). The terms "array," "microarray" and "DNA chip" are used herein interchangeably to refer to an array of distinct polynucleotides affixed to a substrate, such as glass, plastic, paper, nylon or other type of membrane, filter, chip, bead, or any other suitable solid support. The polynucleotides can be synthesized directly on the substrate, or synthesized separate from the substrate and then affixed to the substrate. The arrays can be prepared using known methods. In certain non-limiting embodiments, the one or more test nucleic acid molecules set forth above may constitute at least 10 percent or at least 20 percent or at least 30 percent or at least 40 percent or at least 50 percent or at least 60 percent or at least 70 percent or at least 80 percent of the species of polynucleotides represented on the microarray.

In certain embodiments, the results from the array can then be interpreted to determine the number or approximate number and/or size or approximate size of the CNVs in the genome or portion thereof. For example, and not by way of limitation, software such as Partek GenomeSuite 6.6 can be used.

5.4.2 Fusion Gene Detection

The present invention provides methods for detecting one or more fusion genes in a sample of a subject. The fusion genes can be detected by detecting a fusion gene manifested in a DNA molecule, an RNA molecule or a protein. In certain embodiments, a fusion gene can be detected by determining the presence of a DNA molecule, an RNA molecule or protein that is encoded by the fusion gene. For example, and not by way of limitation, the presence of a fusion gene may be detected by determining the presence of the protein encoded by the fusion gene. In certain embodiments, the fusion gene can be detected in a sample of a subject.

In certain non-limiting embodiments, the fusion gene is detected by nucleic acid hybridization analysis.

In certain non-limiting embodiments, the fusion gene is detected by fluorescent in situ hybridization (FISH) analysis. FISH is a technique that can directly identify a specific sequence of DNA or RNA in a cell or biological sample and enables visual determination of the presence and/or expression of a fusion gene in a tissue sample. In certain non-limiting embodiments, where a fusion gene combines genes not typically present on the same chromosome, FISH analysis may demonstrate probes binding to the same chromosome. For example, and not by way of limitation, analysis may focus on the chromosome where one gene normally resides and then hybridization analysis may be performed to determine whether the other gene is present on that chromosome as well.

In certain non-limiting embodiments, the fusion gene is detected by DNA hybridization, such as, but not limited to, Southern blot analysis.

In certain non-limiting embodiments, the fusion gene is detected by RNA hybridization, such as, but not limited to, Northern blot analysis. In certain embodiments, Northern blot analysis can be used for the detection of a fusion gene, where an isolated RNA sample is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography to detect the presence of a fusion gene in the RNA sample.

In certain non-limiting embodiments, the fusion gene is detected by nucleic acid sequencing analysis.

In certain non-limiting embodiments, one or more fusion genes can be detected by probes present on a DNA array, chip or a microarray. For example, and not by way of limitation, oligonucleotides corresponding to one or more fusion genes can be immobilized on a chip which is then hybridized with labeled nucleic acids of a sample obtained from a subject. Positive hybridization signal is obtained with the sample containing the fusion gene transcripts. In certain non-limiting embodiments, the one or more probes set forth above can constitute at least 10 percent or at least 20 percent or at least 30 percent or at least 40 percent or at least 50 percent or at least 60 percent or at least 70 percent or at least 80 percent of the species of probes represented on the microarray.

In certain non-limiting embodiments, the fusion gene is detected by a method comprising Reverse Transcription Polymerase Chain Reaction ("RT-PCR").

In certain non-limiting embodiments, the fusion gene is detected by antibody binding analysis such as, but not limited to, Western Blot analysis and immunohistochemistry.

5.5. Kits

The present invention further provides kits that can be used to practice the invention. For example, and not by way of limitation, a kit of the present invention can comprise an array that allows the analysis of CNVs across the whole genome. A non-limiting embodiment of such an array is the Affymetrix SNP Array 6.0. In certain non-limiting embodiments, the nucleic acid molecules for detecting CNVs may constitute at least 10 percent or at least 20 percent or at least 30 percent or at least 40 percent or at least 50 percent or at least 60 percent or at least 70 percent or at least 80 percent of the species of polynucleotides represented on the microarray.

In certain embodiments, a kit of the present invention can optionally comprise software or internet access to software, in electronically readable form, that determines the number and size of CNVs in the genes represented in the array. In certain embodiments, the kit can optionally comprise software or internet access to software, in electronically readable form, that determines whether CNVs in a DNA sample exceed or fall below a size threshold and can further determine the large size ratio, set forth herein, which indicates whether or not a prostate cancer patient is at an increased risk of relapse or an increased risk of rapid relapse.

The present invention further provides kits for detecting one or more of the fusion genes disclosed herein within a sample of a subject. Types of kits include, but are not limited to, packaged fusion gene-specific probe and primer sets (e.g., TaqMan probe/primer sets), arrays/microarrays or antibodies for detecting one or more fusion genes. In certain embodiments, a kit of the present invention can include packaged fusion gene-specific probe and primer sets (e.g., TaqMan probe/primer sets), arrays/microarrays or antibodies for detecting one or more fusion genes selected from the group consisting of TRMT11-GRIK2, SLC45A2-AMACR, MTOR-TP53BP1, LRRC59-FLJ60017, TMEM135-CCDC67, KDM4B-AC011523.2, CCNH-C5orf30 and MAN2A1-FER. In certain non-limiting embodiments, the one or more probes and/or primers for detecting fusion genes indicated above can constitute at least 10 percent or at least 20 percent or at least 30 percent or at least 40 percent or at least 50 percent or at least 60 percent or at least 70 percent or at least 80 percent of the species of probes and/or primers represented on the microarray.

The following Example is offered to more fully illustrate the disclosure, but is not to be construed as limiting the scope thereof.

6. EXAMPLE 1: ANALYSIS OF SIZE AND NUMBER OF CNVS IN PROSTATE CANCER PATIENTS

6.1 Introduction

Accurate prediction of prostate cancer clinical courses remains elusive. In this study, we performed whole genome copy number analysis on leukocytes of 273 prostate cancer patients using Affymetrix SNP 6.0 chip. Copy number variations (CNV) were found across all chromosomes of the human genome. An average of 152 CNV fragments per genome was identified in the leukocytes from prostate cancer patients. The size distributions of CNV in the genome of leukocytes were highly correlative with prostate cancer aggressiveness. A prostate cancer outcome prediction model was developed based on large size ratio of CNV from the leukocyte genomes. This prediction model generated an average prediction rate of 75.2%, with sensitivity of 77.3% and specificity of 69.0% for prostate cancer recurrence. When combined with Nomogram and the status of fusion transcripts, the average prediction rate was improved to 82.5% with sensitivity of 84.8% and specificity of 78.2%. In addition, the leukocyte prediction model was 62.6% accurate in predicting short prostate specific antigen doubling time. When combined with Gleason's grade, Nomogram and the status of fusion transcripts, the prediction model generated a correct prediction rate of 77.5% with 73.7% sensitivity and 80.1% specificity. To our knowledge, this is the first study showing that CNVs in leukocyte genomes are predictive of clinical outcomes of a human malignancy.

Previous cytogenetic and other genome studies suggested a clear link between genome abnormalities and prostate cancer (5-21). Recent analyses of genome copy number of prostate cancer, benign tissues adjacent to cancer and blood samples from prostate cancer patients suggested that genome deletion and amplification of certain regions in prostate cancer samples were associated with poor clinical outcomes (14;22). Whole genome and transcriptome sequencing revealed fusion transcripts in prostate cancer predictive of prostate cancer recurrence (23). In this study, whole genome copy number analyses on leukocytes from prostate cancer patients were performed. Significant copy number variations (CNV) were identified in the genome of leukocytes of prostate cancer patients. It was found that sizes of CNVs in leukocytes of prostate cancer samples were highly correlative to prostate cancer recurrence. Prediction models were built to predict prostate cancer outcomes based on the size of CNVs of the leukocytes.

6.2 Materials and Methods

Tissue Processing, DNA Extraction, Amplicon Generation, Labeling, Hybridization, Washing and Scanning of SNP 6.0 Chips.

Prostate cancer samples were obtained from University of Pittsburgh Medical Center Tissue Bank. These samples were collected from 1998-2012. Two hundred seventy-three buffy coat samples from prostate cancer patients were analyzed. Among these samples, 143 samples were followed at least 90 months, 35 patients were non-recurrent for 90 months or more, 55 patients experiencing recurrence with short PSADT (PSA doubling time <4 months), and 53 patients experiencing recurrence with long PSADT (PSA doubling time >15 months) after radical prostatectomy (Table 3). The Gleason's scores of all prostate cancer samples were reassessed by UPMC pathologists before the study. Clinical follow-up was conducted by office examination record, blood PSA survey and radiographic follow-up. These follow-ups were carried out for up to a 15 year period after the patient had a radical prostatectomy. The protocol was approved by "University of Pittsburgh Institutional Review Board". Five hundred nanograms of genomic DNA were digested with Sty1 and Nsp1 for 2 hours at 37° C. The digested DNA was purified and ligated with primer/adaptors at 16° C. for 12-16 hours Amplicons were generated by performing PCR using primers provided by the manufacturer (Affymetrix, CA) on the ligation products using the following program: 94° C. for 3 min, then 35 cycles of 94° C. 30 second, 60° C. for 45 sec and 65° C. for 1 minute. This was followed by extension at 68° C. for 7 min. The PCR products were then purified and digested with DNAseI for 35 min at 37° C. to fragment the amplified DNA. The fragmented DNA was then labeled with biotinylated nucleotides through terminal deoxynucleotide transferase for 4 hours at 37° C. Two hundred fifty micrograms of fragmented DNA were hybridized with a pre-equilibrated Affymetrix chip SNP 6.0 at 50° C. for 18 hours. Procedures of washing and scanning of SNP 6.0 chips followed the manuals provided by Affymetrix, Inc. Raw data information of SNP6.0 from these samples was deposited in "Gene Expression Omnibus" (GEO, accession number GSE70650).

Statistical Analysis:

Copy number variation analysis: CEL files were analyzed with Genotyping Console for quality control (QC) analysis. Samples with QC call above 80% and QC contrast ratio above 0.4 were admitted into the analysis. To analyze CNV, CEL files were imported into Partek GenomeSuite 6.6 to generate copy number from raw intensity. To plot the histograms, deletion or amplification of genomes were analyzed by first limiting to the regions with p-value less than 0.001. The selected regions were subsequently filtered by limiting to the regions with at least 10 markers and 2 kb in size. The regions were then mapped to known genes. The frequencies of amplification and deletions were plotted to the genome corresponding to the gene locations (FIG. 1A). For each gene, Fisher's exact test was applied to test the association between CNV involvement and sample recurrence status. Then the minus log p-values were plotted on the Manhattan plot with their corresponding gene chromosome locations to generate FIG. 1B. Benjamini-Hochberg (BH) method was applied to correct the p-values. The CNV-gene enriched pathways were selected by Kolmogorov-Smirnov test on the gene adjusted p-values. Pathway p-values were also corrected by BH method.

Machine learning methods to predict recurrent and fast-recurrent status: prediction models for two types of clinical comparisons were constructed: (1) non-recurrent versus recurrent; (2) non-fast recurrent (i.e., non-recurrent or recurrent but having prostate specific antigen doubling time [PSADT]>15 months) versus fast-recurrent (recurrent PSADT<4 months). For each comparison, the models were constructed using Gleason score (G), Nomogram score (N), fusion transcript status (F) or blood CNV information (L) separately. For Gleason score discrimination, binary prediction was used (0 meaning Gleason score <7 and 1 meaning Gleason score >7). For Nomogram score, the 7 year survival probability obtained from www.mskcc.org/nomograms/prostate was used (24). For fusion status, eight fusion transcripts (TRMT11-GRIK2, SLC45A2-AMACR, MTOR-TP53BP1, LRRC59-FLJ60017, TMEM135-CCDC167, KDM4-AC011523.2, MAN2A1-FER and CCNH-C5orf30) previously identified and validated in a multi-center study (23) were applied. A binary fusion score was used (0 meaning none of the eight fusions detected; 1 meaning one or more fusion transcripts detected).

For prediction using gene CNV of leukocytes, little predictive power from gene-based association was found (FIG. 1B). As a result, a large size ratio (LSR) model was developed based on the assumption that untargeted CNV aberrations in blood played a significant role in predisposing prostate tumors to aggressiveness. As shown in FIG. 2A, LSR was defined as the proportion of large size CNV identified in the blood genome of a given patient, where large size was defined by threshold δ. In each two-fold cross-validation, samples were randomly and equally split into two data sets. In the first dataset treated as training data, the best δ parameter in LSR model and the best cutoffs of Nomogram and LSR scores were selected by maximizing the highest AUC (area under the curve) and Youden index (i.e., sensitivity+specificity−1). The models were then applied to the second dataset as testing data. The cross-validation was then repeated using the second dataset as training data and the first dataset as test data. ROC curves were plotted by varying the cutoffs in both the training and testing datasets. The corresponding overall accuracy, sensitivity, specificity, Youden index and AUC were calculated to evaluate the performance. The equal-splitting validation was repeated for 14 times and the top 2 and bottom 2 splitting with the highest and lowest sum of AUCs were removed to avoid accidentally extreme training/testing assignment. The remaining 10 cross-validation results were finally averaged (Table 1 and Table 2). ROC and Kaplan-Meier survival curves in FIG. 3-6 are the representative results of the 10 predictions closest to the averaged values.

To test whether combining multiple data information improves the prediction result, we applied linear discriminant analysis (LDA) to combine two or more predictive factors. All possible combinations were performed. Models using (1) L+N+F; (2) L+N+G; (3) N+F+G; (4) L+F+G; (5) L+N+F+G are shown in FIGS. 3 and 5.

Kaplan-Meier curve analysis: For the survival evaluation (FIGS. 4 and 6), the two-fold cross validation of "Training⇒Testing" result was combined to compare the performance of different methods, except for Gleason score that we used (<7 VS >7 as cut-off for the whole samples). Kaplan-Meier curves were truncated at 90 months follow-up. Log-rank test was performed to calculate the p-value between survival curves of two predicted outcomes. To evaluate whether the survival difference for one model was significantly better than the other, we define a test statistics U as the absolute difference of the log-rank test statistics from the two models. Theoretically under the null hypothesis (two models were non-discriminant), the test statistics U followed a distribution of absolute difference of two independent chi-squared (degree of freedom=1) distributions. As a result, 10,000,000 times from the absolute difference of two independent chi-squared distributions were sampled to form null distribution and evaluate the p-values.

6.3 Results

Genome copy abnormalities are some of the hallmarks for prostate cancer. However, little is known about the genome copy abnormalities in non-cancerous tissues from prostate cancer patients. To analyze the regions of amplification and deletion in the genome of leukocytes from prostate cancer patients, 273 buffy coats from prostate cancer patients were analyzed for CNV across the entire genome using Affymetrix SNP6.0. Using the cutoff criteria of size≥2 Kb, marker number ≥10 and p<0.001, a total of 41589 CNV fragments were identified, including 24213 segments of deletion and 17376 of amplification, involving 17865 genes based on the Partek gene annotation (FIG. 1A). This translates to an average of about 152 CNVs per sample. The average size of CNV in the genome of the leukocytes is about 147 Kb. On average, 256 genes were found to have either copy number gain or loss per genome. Among the 273 blood samples, 143 blood samples have more than 90 months of clinical follow-ups in terms of prostate cancer recurrence. Interestingly, when categorizing the blood samples based on the status of prostate cancer recurrence, CNV of leukocytes from patients who experienced recurrence after radical prostatectomy had an average of >3.2 fold larger size of CNV versus CNV from patients who had no recurrence for at least 90 months. Two-sided t test showed a strong correlation between the size of CNV in leukocytes and prostate cancer recurrence (p=2.2×10-16), suggesting that the size of germ line CNV may play a significant role in predisposing prostate cancer to aggressive clinical courses. However, no specific (FDR=0.05) gene involved in CNV of genome fragment reaches the threshold that differentiates recurrent prostate cancer versus those of non-recurrent (FIG. 1B). Together, the results indicate that the gene-based prediction model is unlikely to succeed in the leukocyte CNV analysis but size distribution of CNVs can be predictive.

To examine whether germ line CNV is predictive of recurrence of prostate cancer, an algorithm utilizing ratios of the number of large size fragments was developed. As illustrated in FIG. 2A, for each sample, large size ratio (LSR) is defined as the ratio of CNV fragments whose sizes are greater than a size cutoff (δ) over the total number of CNV fragments. For example, 3 of the 7 detected CNVs in FIG. 2A are found "large size fragments" (size≥δ) and the LSR of this patient is calculated as 3/7=0.43. In FIG. 2B, the distribution of LSR from patients who experienced prostate cancer recurrence showed significantly higher values than those who did not experience recurrence. Similarly, the distribution of LSR from patients with fast recurrence (PSADT<4 months) was significantly higher than those from non-fast recurrent patients (non-recurrent or recurrent but having PSADT>15 months, FIG. 2C). In the LSR model, the size threshold δ is determined by maximizing the AUC. When δ values were optimized (FIG. 7, δ=104.5=31622 bp for recurrent prediction model and 1B selected δ=105.7=501187 bp for fast recurrent prediction), it predicts prostate cancer recurrence with accuracy of 77.6%, with sensitivity of 80.4% and specificity of 68.6%, while fast recurrence with accuracy of 62.4%, with sensitivity of 72.9% and specificity of 54.1%.

To validate this model, 143 blood samples (Table 3) from prostate cancer patients were randomly split into a training set (72 samples) and a testing set (71 samples). The optimized large-size cutoff 6 and LSR-cutoff were obtained from the training analysis by maximizing the Youden index. The parameters were then applied to the testing data set to assess the prediction accuracy. The validation was then repeated 14 times and the best 2 and worst 2 were removed to avoid extreme randomization. The remaining 10 results from these training and testing analyses were averaged (Table 1). As shown in FIG. 3A (representative analyses in Table 4) and Table 1, the training accuracy of LSR model in predicting prostate cancer recurrence reaches 76.5%, with 77.8% sensitivity and 72.4% specificity. When the parameters were applied to the testing set, the prediction accuracy reaches 73.9%, with 76.8% sensitivity and 65.6% specificity. These prediction rates are better than those of Nomogram (66.0% accuracy for training and 61.3% for testing, Table 1), and are significantly higher than those of Gleason grade's with single cutoff (40.3% for training and 39.4% for testing; $p=8.6\times10^{-3}$ for training and $p=5.8\times10^{-3}$ for testing by ROC comparison, see Table 1 and Table 5).

To examine whether combination of different modalities will improve the prediction model, blood LSR, Nomogram, Gleason's grade and the status of 8 fusion transcripts (TRMT11-GRIK2, SLC45A2-AMACR, MTOR-TP53BP1, LRRC59-FLJ60017, TMEM135-CCDC67, KDM4-AC011523.2, MAN2A1-FER and CCNH-C5orf30) (23) in the prostate cancer samples were combined through linear discriminant analysis (LDA) to train the prediction model in the training set. Such model generated a prediction accuracy of 87.9%, with 88.8% sensitivity and 85.4% specificity for prostate cancer recurrence in the training set, and accuracy of 75.7%, with 81.7% sensitivity and 64.0% specificity in the testing set (FIG. 3B and Table 1). Interestingly, the combination of LSR, Nomogram and the status of fusion transcripts appears to produce the best prediction results: 86.4% accuracy in the training set and 78.6% accuracy in the testing set. These prediction rates appear significantly better than those generated from any single modality (Table 1). To evaluate the contribution of each of these modalities to the combination model, subtraction of one of each modality at a time was made on the model to evaluate their impacts respectively. As shown in FIG. 3B and Table 1, subtraction of LSR modality appeared to have the most significant impact on prediction of prostate cancer recurrence: The prediction accuracy rates drop from 87.9% to 75.1% (ROC p=0.044, see Table 5) in the training sets and from 75.7% to 64.0% (ROC p=0.037) in the testing sets. This was followed by fusion genes (p-value between the two ROC curves was 0.109 for training and 0.159 for testing). On the other hand, subtraction of Nomogram or Gleason grade had no appreciable impact on the prediction performance of the model (Table 1, FIG. 3 and Table 5).

To examine the prediction performance of LSR score on PSA-free survival of prostate cancer patients, Kaplan-Meier analyses were performed on 143 patients who had definitive clinical information (Table 3). Recurrence status for testing samples were predicted by the model trained from the training set, and the prediction model of training samples was trained from testing set. The merged two-fold cross-validation prediction results were used to divide the 143 patients into predicted recurrent group and non-recurrent group. As shown in FIG. 4, when patients were predicted by LSR as high risk for prostate cancer recurrence, only 12.1% of the patients survived for 90 months without recurrence, while over 52.3% patients with LSR model predicted to be likely non-recurrent survived 90 months without any sign of recurrent prostate cancer (average $p=9.9\times10^{-5}$ by log-rank test, FIG. 4 and Table 6). In contrast, Gleason score failed to produce statistically significant different results for recurrent and non-recurrent groups (p=0.113 by log-rank test). Nomogram, however, generated statistically significant better clinical outcomes (33.9% versus 18.4% survival rate and p=0.0038 for log-rank test) when patients were segregated based on predicted recurrent versus non-recurrent by Nomogram. When fusion transcripts, leukocyte genome LSR and Nomogram were combined, it improved the outcomes of prostate cancer prediction to 58.1% PSA-free survival if they were predicted to be non-recurrent by the model versus 16.9% if they were predicted as likely recurrent by the combined model ($p=2.9\times10^{-6}$ for the two survival curves). This combined-modality model significantly outperforms any single modality prediction model ($p=6.6\times10^{-3}$ versus LSR, $p=1.8\times10^{-5}$ versus Gleason, $p=3.5\times10^{-4}$ versus Nomogram, p=0.017 versus fusion transcripts, see Table 7). When Gleason grading was added to model, it did not improve the accuracy of prediction, but improved the survival curves.

Prostate cancer related death is closely associated with rising velocity of recurrent seral PSA. Short PSADT (<4 months) had been used as a surrogate for prostate cancer related death for the last 15 years (25; 26). To examine whether LSR in the genome of leukocytes is also predictive of short PSADT, blood samples (Table 3) were randomly split into training (65 samples) and testing (64 samples) sets. Similar processes were performed on these samples as described in recurrence prediction. As shown in Table 2, the LSR model in the training and testing data sets yielded an accuracy of prediction of PSADT=<4 months as 67.7% and 57.5%, respectively. The ROC curve of LSR model versus the diagonal line (random guess) has p-value=0.016 for the training set and 0.017 for the testing set (FIG. 5, Table 2 and Table 8). The prediction based on Gleason scores yielded 42.3% accuracy for training set, and 44.5% for the testing data set. On the other hand, Nomogram generated a prediction accuracy of 67.8% and ROC p-value of 0.0082 in the training set and 64.5% accuracy and 0.0014 ROC p-value in the testing set. The status of fusion transcripts in the prostate cancer samples produced an accuracy of 68.8% and 68.4% in training and testing data sets, respectively. These 4 methods did not appear to be significantly better than one another when pairwise proportion tests were performed. However, when all 4 methods were combined, it yielded an accuracy of 83.0% (ROC $p=5.3\times10^{-9}$) for the training set and 72.0% (ROC $p=1.3\times10^{-4}$) for the testing set. These results were better than any single prediction modality in terms of accuracy, AUC and Youden Index values (Table 2).

To investigate the impact of each of these modalities on the prediction model, each modality was individually subtracted from the combined prediction model. The prediction results showed a range of 72.8-82.5% accuracy in the training data set and 65.0-73.6% accuracy in the testing data set, when one modality was subtracted. Interestingly, when either blood LSR or cancer fusion transcript status was subtracted, the combined models yielded no significantly better predictions than any single modality prediction except Gleason's (Table 9), suggesting that blood LSR and fusion transcript status were the most significant contributors in the combined prediction model.

To analyze the impact of short PSADT prediction on prostate cancer PSA-free survivals, Kaplan-Meier analyses were performed on samples segregated based on the PSADT prediction by leukocyte genome LSR. As shown in FIG. 6 and Table 10, when samples predicted by blood LSR to have PSADT<4 months, the PSA-free survival rate was 17.1% at 90th-month after radical prostatectomy, while the survival rate improved to 41.5% for those predicted to have PSADT>15 months or non-recurrent (log-rank test p=0.0039, see FIG. 6 and Table 10). In contrast, survival curves predicted by Gleason score ended up with similar survival rate at 90-month, and the p-value between two curves was 0.0816 by log-rank test. Nomogram had the PSA-free survival rate of 21.4% when patients were predicted to have PSADT<4 months. This survival rate was 31.5% when patients were predicted to be non-recurrent (p=0.0021 by log-rank test). However, when the model combining Gleason, Nomogram, fusion transcripts and blood LSR was applied, the PSA-free survival rate was only 7.9% when patients were predicted to have PSADT<4 months, while the survival rate was 52.1% when the patients were predicted to have PSADT>4 months or non-recurrent (p=1.6×10-7). The model combining 4 modalities significantly outperformed the prediction models based on Gleason grade (p=1.5×10-6) or Nomogram (p=3.0×10-5) or LSR (p=1.9×10-5) or fusion transcripts (p=0.0018) alone (Table 11). These analyses clearly indicate that the sizes of copy number variation of human leukocytes are correlative with clinical behavior of prostate cancer. The combination of the genome CNV of leukocytes with clinical information of prostate cancer patients would yield much improved prediction models for prostate cancer behavior.

6.4. Discussion

Extensive presence of CNV is one of the important features of human malignancies. CNV in normal tissues of healthy individuals was also well documented (14; 27; 28). Since CNV analysis is largely insensitive to small contamination, it may require more than 25% contamination to detect an alteration of copy number in the genome. Small contamination of the blood stream by prostate cancer cells is generally undetected. The CNVs detected from the buffy coats in our study probably represent the genome CNVs from leukocytes. Our studies suggest that the sizes of CNV from leukocytes of prostate cancer patients are highly correlative with the clinical outcomes of prostate cancer. These CNVs spreads across all the chromosomes. Most of these CNVs overlap with the gene coding sequences of the genome. Interestingly, neither specific CNV fragment nor gene involved by these CNVs is significantly associated with the outcome of prostate cancer, suggesting that the impact of CNVs on prostate cancer is of collective nature. However, pathway analysis on genes that were involved in leukocyte genome CNV revealed enrichment of olfactory signaling pathways in recurrent-high risk patients from REACTOME (adjusted p=5.0×10-10 using Kolmogorov-Smirnov test) and KEGG (adjusted p=6.9×10-10) databases. The significance of leukocyte genome CNV enriched in this pathway is not clear. A recent study also suggests that higher copy number of mitochondria DNA is associated with the risk of prostate cancer. But it is unclear whether mitochondria DNA copy number is correlated with prostate cancer metastasis (29). There is no clear link of leukocyte CNV with the severity of infiltrating lymphocytes in the prostate cancer samples.

The widespread and sporadic nature of these CNVs indicates that the leukocyte CNVs are of germline origin. As a result, our study implies that high numbers of large size germline CNVs predispose prostate cancer to aggressive behavior. These large size CNVs frequently overlap with multiple genes. The larger the size of the CNV is, the higher the number of genes could be impacted, and thus more metabolic and signaling pathways would be hit. Interestingly, one of the most frequent genes detected in large size CNVs is UDP glucuronosyltransferase 2 family, polypeptide B17 (UGT2B17). This gene encodes an enzyme responsible for transferring of glucuronic acid from uridine diphosphoglucuronic acid to a diverse array of substrates including steroid hormones and lipid-soluble drugs. UGT2B17 is essential for steroid metabolism. Genome deletion of UGT2B17 is associated with higher testosterone level (30). As a result, germline CNV of UGT2B17 may have an impact on sex hormone metabolism, and thus affects the clinical course of prostate cancer. The expression levels of genes involved in CNV may be altered even in normal cells due to higher or lower copy number of the transcription units. Such subtle alterations could be exacerbated when cells become malignant because of the loss of the off-set mechanism. Indeed, higher numbers and larger sizes of CNVs and bigger CNV burden in prostate cancer samples are correlative with prostate cancer aggressiveness (14; 31). As a result, germline CNV is possibly a pre-condition and down-stream mechanism leading to aggressive behavior of prostate cancer.

Prostate cancer is highly heterogeneous with various clinical outcomes. Most prostate cancers do not develop into life-threatening disease. Only a small fraction of prostate cancers are lethal and require aggressive treatment. When prostate cancer samples were segregated as likely lethal (recurrence occurred <12 months after radical prostatectomy and PSDAT<4 months) versus those with no recurrence at all for 90 months, leukocyte LSR correctly predicted 78.3% accuracy with 73.9% sensitivity and 82.9% specificity for training and 66.9% accuracy with 59.4% sensitivity and 73.9% specificity for testing (Table 12-16; FIGS. 8 and 9). The model combining leukocyte LSR with Nomogram and fusion transcript status has an accuracy of 95.7% with 96.6% sensitivity and 94.7% specificity for training and an accuracy of 82.9% with 79.6% sensitivity and 85.5% specificity for testing. The multi-modality model outperformed all model based on single criteria in judging the lethality of prostate cancer.

Gleason's grading has been the mainstay in judging the potential behavior of prostate cancer for many years. The accuracy of Gleason's prediction is generally good when Gleason's grade is high (8 and above). However, the prediction rates for prostate cancers with mid-range scores such as 7, are much less accurate. Furthermore, final Gleason's grades cannot be determined until the entire prostate gland is examined. Thus, the determination of treatment modality of prostate cancer could be problematic. Even though genomic or epigenomic analyses of cancer cells from the blood (32) or from prostate (14; 33; 34) can offer significant insight into the prognosis of prostate cancer, leukocyte CNV represents the most non-invasive and least laborious approach to assess the metastatic potential of cancer. Conceivably, leukocyte CNV analysis offers an attractive alternative model in predicting prostate cancer clinical outcomes. There are several salient potentials for clinical application using the leukocyte CNV tests: For a patient being diagnosed of prostate cancer, CNV analysis done on the blood samples from the patient would eliminate the need for additional invasive procedure to decide a treatment mode. For a patient already having a radical prostatectomy, the CNV analysis on the blood sample, combined with information of fusion transcript status and Nomogram, may help to decide whether additional treatment is warranted to prevent prostate cancer recurrence. Since the leukocyte genome CNV test required no prostate cancer sample, it would be extremely useful if a patient has only a limited number of prostate cancer cells and Gleason's grading or other pathological features cannot be determined. The only limitation of leukocyte CNV test is its slightly higher cost. In addition, the leukocyte CNV test is highly complement to clinical prediction parameters such as Gleason's grade and Nomogram, and it enhances the prediction precision of these clinical parameters. As a result, the CNV analysis on the genome of leukocytes of prostate cancer patients may hold promise to become an important way to predict the behavior of prostate cancer.

7. REFERENCES

1. Isaacs J T (1997) Molecular markers for prostate cancer metastasis. Developing diagnostic methods for predicting the aggressiveness of prostate cancer. The American journal of pathology 150: 1511-1521.
2. Potosky A L, Miller B A, Albertsen P C, Kramer B S (1995) The role of increasing detection in the rising incidence of prostate cancer. Jama 273: 548-552.
3. Gittes R F (1991) Carcinoma of the prostate. The New England journal of medicine 324: 236-245.
4. Siegel R, Naishadham D, Jemal A (2012) Cancer statistics, 2012. CA: a cancer journal for clinicians 62: 10-29.
5. Pang S T, Weng W H, Flores-Morales A, Johansson B, Pourian M R et al. (2006) Cytogenetic and expression profiles associated with transformation to androgen-resistant prostate cancer. The Prostate 66: 157-172.
6. Matsui S, LaDuca J, Rossi M R, Nowak N J, Cowell J K (2005) Molecular characterization of a consistent 4.5-megabase deletion at 4q28 in prostate cancer cells. Cancer genetics and cytogenetics 159: 18-26.
7. Bettendorf O, Schmidt H, Eltze E, Gockel I, Semjonow A et al. (2005) Cytogenetic changes and loss of heterozygosity in atypical adenomatous hyperplasia, in carcinoma of the prostate and in non-neoplastic prostate tissue using comparative genomic hybridization and multiplex-PCR. International journal of oncology 26: 267-274.
8. Teixeira M R, Ribeiro F R, Eknaes M, Waehre H, Stenwig A E et al. (2004) Genomic analysis of prostate carcinoma specimens obtained via ultrasound-guided needle biopsy may be of use in preoperative decision-making. Cancer 101: 1786-1793.
9. Macoska J A, Paris P, Collins C, Andaya A, Beheshti B et al. (2004) Evolution of 8p loss in transformed human prostate epithelial cells. Cancer genetics and cytogenetics 154: 36-43.
10. Kraus J, Pantel K, Pinkel D, Albertson D G, Speicher M R (2003) High-resolution genomic profiling of occult micrometastatic tumor cells. Genes, chromosomes & cancer 36: 159-166.
11. Lin F, Yu Y P, Woods J, Cieply K, Gooding B et al. (2001) Myopodin, a synaptopodin homologue, is frequently deleted in invasive prostate cancers. American Journal of Pathology 159: 1603-1612.
12. Ren B, Yu G, Tseng G C, Cieply K, Gavel T et al. (2006) MCMI amplification and overexpression are associated with prostate cancer progression. Oncogene 25: 1090-1098.
13. Yu G, Tseng G C, Yu Y P, Gavel T, Nelson J et al. (2006) CSR1 suppresses tumor growth and metastasis of prostate cancer. American Journal of Pathology 168: 597-607.
14. Yu Y P, Song C, Tseng G, Ren B G, Laframboise W et al. (2012) Genome abnormalities precede prostate cancer and predict clinical relapse. The American journal of pathology 180: 2240-2248.
15. Luo J H, Yu Y P, Cieply K, Lin F, Deflavia P et al. (2002) Gene expression analysis of prostate cancers. Molecular carcinogenesis 33: 25-35.
16. Luo J H, Yu Y P (2003) Genetic factors underlying prostate cancer. Expert reviews in molecular medicine 5: 1-26.
17. Yu Y P, Tseng G C, Luo J H (2006) Inactivation of myopodin expression associated with prostate cancer relapse. Urology 68: 578-582.
18. Ren B, Yu Y P, Tseng G C, Wu C, Chen K et al. (2007) Analysis of integrin alpha7 mutations in prostate cancer, liver cancer, glioblastoma multiforme, and leiomyosarcoma. Journal of the National Cancer Institute 99: 868-880.
19. Yu Y P, Luo J H (2007) Pathological factors evaluating prostate cancer. Histology and histopathology 22: 1291-1300.
20. Yu Y P, Yu G, Tseng G, Cieply K, Nelson J et al. (2007) Glutathione peroxidase 3, deleted or methylated in prostate cancer, suppresses prostate cancer growth and metastasis. Cancer research 67: 8043-8050.
21. Liu W, Laitinen S, Khan S, Vihinen M, Kowalski J et al. (2009) Copy number analysis indicates monoclonal origin of lethal metastatic prostate cancer. Nature medicine 15: 559-565.
22. Taylor B S, Schultz N, Hieronymus H, Gopalan A, Xiao Y et al. (2010) Integrative genomic profiling of human prostate cancer. Cancer cell 18: 11-22.
23. Yu Y P, Ding Y, Chen Z, Liu S, Michalopoulos A et al. (2014) Novel fusion transcripts associate with progressive prostate cancer. The American journal of pathology 184: 2840-2849.

24. Partin A W, Yoo J, Carter H B, Pearson J D, Chan D W et al. (1993) The use of prostate specific antigen, clinical stage and Gleason score to predict pathological stage in men with localized prostate cancer. The Journal of urology 150: 110-114.
25. Freedland S J, Humphreys E B, Mangold L A, Eisenberger M, Dorey F J et al. (2007) Death in patients with recurrent prostate cancer after radical prostatectomy: prostate-specific antigen doubling time subgroups and their associated contributions to all-cause mortality. J Clin Oncol 25: 1765-1771.
26. Antonarakis E S, Zahurak M L, Lin J, Keizman D, Carducci M A et al. Changes in PSA kinetics predict metastasis-free survival in men with PSA-recurrent prostate cancer treated with nonhormonal agents: combined analysis of 4 phase II trials. Cancer 118: 1533-1542.
27. Sebat J, Lakshmi B, Troge J, Alexander J, Young J et al. (2004) Large-scale copy number polymorphism in the human genome. Science (New York, N.Y. 305: 525-528.
28. Zarrei M, MacDonald J R, Merico D, Scherer S W A copy number variation map of the human genome. Nat Rev Genet 16: 172-183.
29. Zhou W, Zhu M, Gui M, Huang L, Long Z et al. (2015) Peripheral blood mitochondrial DNA copy number is associated with prostate cancer risk and tumor burden. PloS one 9: e109470.
30. Yang T L, Chen X D, Guo Y, Lei S F, Wang J T et al. (2008) Genome-wide copy-number-variation study identified a susceptibility gene, UGT2B17, for osteoporosis. American journal of human genetics 83: 663-674.
31. Hieronymus H, Schultz N, Gopalan A, Carver B S, Chang M T et al. (2014) Copy number alteration burden predicts prostate cancer relapse. Proceedings of the National Academy of Sciences of the United States of America 111: 11139-11144.
32. Xia S, Kohli M, Du M, Dittmar R L, Lee A et al. (2015) Plasma genetic and genomic abnormalities predict treatment response and clinical outcome in advanced prostate cancer. Oncotarget.
33. Luo J H, Ding Y, Chen R, Michalopoulos G, Nelson J et al. (2013) Genome-wide methylation analysis of prostate tissues reveals global methylation patterns of prostate cancer. The American journal of pathology 182: 2028-2036.
34. Yu Y P, Paranjpe S, Nelson J, Finkelstein S, Ren B et al. (2005) High throughput screening of methylation status of genes in prostate cancer using an oligonucleotide methylation array. Carcinogenesis 26: 471-479.

Various references are cited in this document, which are hereby incorporated by reference in their entireties herein.

TABLE 1

Prediction of prostate cancer recurrence based on leukocyte LSR, Gleason, Nomogram and fusion transcript status

| Model | Accuracy | Sensitivity | Specificity | Youden index | AUC | ROC p-value |
|---|---|---|---|---|---|---|
| Equal split training data (n = 72) | | | | | | |
| LSR | 0.765 | 0.778 | 0.724 | 0.502 | 0.779 | $2.15 \times 10^{-5}$ |
| Nomogram | 0.660 | 0.675 | 0.612 | 0.286 | 0.630 | $3.67 \times 10^{-2}$ |
| Gleason | 0.403 | 0.296 | 0.747 | 0.043 | 0.538 | $3.28 \times 10^{-1}$ |
| Fusion | 0.642 | 0.537 | 0.897 | 0.434 | 0.717 | $5.84 \times 10^{-4}$ |
| L + N + F | 0.864 | 0.856 | 0.885 | 0.742 | 0.917 | $2.12 \times 10^{-13}$ |
| L + N + G | 0.768 | 0.767 | 0.771 | 0.538 | 0.803 | $1.69 \times 10^{-6}$ |
| N + F + G | 0.751 | 0.698 | 0.870 | 0.568 | 0.799 | $3.05 \times 10^{-5}$ |
| L + F + G | 0.863 | 0.867 | 0.850 | 0.717 | 0.910 | $3.33 \times 10^{-12}$ |
| L + N + F + G | 0.879 | 0.888 | 0.854 | 0.742 | 0.923 | $3.75 \times 10^{-14}$ |
| Equal split testing data (n = 71) | | | | | | |
| LSR | 0.739 | 0.768 | 0.656 | 0.423 | 0.760 | $1.38 \times 10^{-4}$ |
| Nomogram | 0.613 | 0.653 | 0.494 | 0.147 | 0.589 | $1.93 \times 10^{-1}$ |
| Gleason | 0.394 | 0.277 | 0.739 | 0.016 | 0.513 | $3.52 \times 10^{-1}$ |
| Fusion | 0.647 | 0.530 | 0.892 | 0.422 | 0.711 | $9.11 \times 10^{-4}$ |
| L + N + F | 0.786 | 0.839 | 0.678 | 0.517 | 0.879 | $4.19 \times 10^{-9}$ |
| L + N + G | 0.692 | 0.719 | 0.611 | 0.330 | 0.722 | $1.77 \times 10^{-3}$ |
| N + F + G | 0.640 | 0.641 | 0.650 | 0.292 | 0.709 | $8.82 \times 10^{-3}$ |
| L + F + G | 0.760 | 0.812 | 0.660 | 0.472 | 0.856 | $1.61 \times 10^{-7}$ |
| L + N + F + G | 0.757 | 0.817 | 0.640 | 0.457 | 0.853 | $3.94 \times 10^{-7}$ |

L—LSR;
N—Nomogram;
F—fusion transcript status;
G—Gleason grade.
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.
The results represent the average of the analyses on 10 random equal splits of training and testing results.

TABLE 2

Prediction of prostate cancer recurrent PSADT ≤4 months based on leukocyte LSR, Gleason, Nomogram and fusion transcript status

| Model | Accuracy | Sensitivity | Specificity | Youden index | AUC | ROC p-value |
|---|---|---|---|---|---|---|
| Equal split training data (n = 65) | | | | | | |
| LSR | 0.655 | 0.739 | 0.592 | 0.331 | 0.662 | $1.63 \times 10^{-2}$ |
| Nomogram | 0.678 | 0.593 | 0.743 | 0.336 | 0.676 | $8.19 \times 10^{-3}$ |
| Gleason | 0.423 | 0.300 | 0.743 | 0.043 | 0.550 | $4.63 \times 10^{-1}$ |
| Fusion | 0.688 | 0.626 | 0.725 | 0.351 | 0.676 | $1.89 \times 10^{-2}$ |
| L + N + F | 0.825 | 0.788 | 0.850 | 0.638 | 0.860 | $8.00 \times 10^{-9}$ |
| L + N + G | 0.728 | 0.779 | 0.689 | 0.468 | 0.743 | $1.97 \times 10^{-4}$ |
| N + F + G | 0.791 | 0.710 | 0.845 | 0.555 | 0.794 | $2.55 \times 10^{-4}$ |
| L + F + G | 0.809 | 0.822 | 0.798 | 0.620 | 0.839 | $5.34 \times 10^{-7}$ |
| L + N + F + G | 0.830 | 0.806 | 0.846 | 0.652 | 0.866 | $5.29 \times 10^{-9}$ |
| Equal split testing data (n = 64) | | | | | | |
| LSR | 0.595 | 0.636 | 0.564 | 0.200 | 0.660 | $1.67 \times 10^{-2}$ |
| Nomogram | 0.645 | 0.611 | 0.670 | 0.281 | 0.707 | $1.39 \times 10^{-3}$ |
| Gleason | 0.445 | 0.324 | 0.754 | 0.078 | 0.532 | $5.68 \times 10^{-1}$ |
| Fusion | 0.684 | 0.613 | 0.731 | 0.344 | 0.672 | $1.96 \times 10^{-2}$ |
| L + N + F | 0.736 | 0.669 | 0.782 | 0.451 | 0.799 | $4.84 \times 10^{-5}$ |
| L + N + G | 0.650 | 0.678 | 0.630 | 0.308 | 0.715 | $1.45 \times 10^{-3}$ |
| N + F + G | 0.699 | 0.598 | 0.764 | 0.362 | 0.764 | $5.97 \times 10^{-4}$ |
| L + F + G | 0.698 | 0.668 | 0.723 | 0.390 | 0.768 | $4.79 \times 10^{-4}$ |
| L + N + F + G | 0.720 | 0.667 | 0.756 | 0.423 | 0.788 | $1.26 \times 10^{-4}$ |

L—LSR;
N—Nomogram;
F—fusion transcript status;
G—Gleason grade.
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.
The results represent the average of the analyses on 10 random equal splits of training and testing results.

TABLE 3

Clinical information for 143 blood samples.

| Case name | Age | Race | Pre-operative PSA | Gleason grad | Pathological stage | 5-year Nomogram | Prostate cancer recurrence | Fast recurrence | Time to relapse (Month) | PSADT | Surgical year |
|---|---|---|---|---|---|---|---|---|---|---|---|
| 11563B | 70s | W | 8.4 | 3 + 4 = 7 | T1cN0MX | 0.97 | no | nf | >90 | N/A | 1998 |
| 1199B | 50s | W | 40 | 3 + 5 = 8 | T3bN0MX | 0.88 | yes | nf | 15 | 33.7 | 1999 |
| 13745B | 60s | W | 6.8 | 3 + 4 = 7 | T1cN0MX | 0.97 | no | nf | >90 | N/A | 1998 |
| 16464B | 60s | W | 8.5 | 3 + 4 = 7 | T3bN0MX | 0.92 | yes | nf | 88.5 | 24.6 | 1999 |
| 18176B | 50s | W | 8.8 | 3 + 3 = 6 | T2bN0MX | 0.98 | yes | nf | 87 | 26.9 | 1999 |
| 1942B | 60s | W | 7.5 | 4 + 5 = 9 | T3bN0MX | 0.73 | yes | nf | 80.1 | 14.8 | 1998 |
| 25313B | 50s | W | 9.5 | 5 + 3 = 8 | T3bN0MX | 0.83 | no | nf | >90 | N/A | 1998 |
| 27086B | 50s | W | 9.5 | 3 + 3 = 6 | T2BN0MX | 0.98 | no | nf | >90 | N/A | 1998 |
| 28685B | 50s | W | 56.6 | 4 + 3 = 7 | T3AN0MX | 0.75 | yes | nf | 77.5 | 17.7 | 1998 |
| 28685B2 | 50s | W | 50.2 | 4 + 3 = 7 | T3AN0MX | 0.76 | yes | nf | 79.6 | 17.7 | 1998 |
| 4308B | 60s | W | 12.4 | 3 + 3 = 6 | T1CN0MX | 0.98 | no | nf | >90 | N/A | 1998 |
| 4336B | 60s | W | 2.5 | 3 + 3 = 6 | T1cN0MX | 0.99 | yes | nf | 21.7 | 22.0 | 1997 |
| 4851B | 60s | W | 7 | 4 + 3 = 7 | T1CN0MX | 0.94 | no | nf | >90 | N/A | 1998 |
| 5396B | 60s | W | 9.1 | 5 + 4 = 9 | T2bN1MX | 0.88 | no | nf | >90 | N/A | 2003 |
| 562B | 60s | W | 5.5 | 3 + 3 = 6 | T2AN0MX | 0.98 | no | nf | >90 | N/A | 1998 |
| 6634B | 50s | U | 18.2 | 3 + 3 = 6 | T2bN0MX | 0.98 | no | nf | >90 | N/A | 1998 |
| 6634B2 | 50s | U | 18.2 | 3 + 3 = 6 | T2bN0MX | 0.98 | no | nf | >90 | N/A | 1998 |
| 678B | 70s | W | 10.8 | 4 + 5 = 9 | T3bN0MX | 0.71 | no | nf | >90 | N/A | 2000 |
| 7270B | 70s | W | 4.1 | 3 + 4 = 7 | T3BN1MX | 0.94 | no | nf | >90 | N/A | 2000 |
| 7504B | 70s | U | 10.5 | 4 + 5 = 9 | T3bN0MX | 0.71 | no | nf | >90 | N/A | 1999 |
| 9122B | 50s | W | 13 | 3 + 4 = 7 | T1CN0MX | 0.97 | no | nf | >90 | N/A | 1997 |
| 9122B2 | 50s | W | 14.4 | 3 + 4 = 7 | T1CN0MX | 0.96 | no | nf | >90 | N/A | 1997 |
| DB237B | 70s | W | 6.3 | 3 + 3 = 6 | T2bN0MX | 0.98 | yes | nf | 46 | 25.97 | 2001 |
| DB237B2 | 70s | W | 6.1 | 3 + 3 = 6 | T2bN0MX | 0.98 | yes | nf | 42.3 | 26.24 | 2000 |
| FB104 | 60s | W | 16.6 | 4 + 4 = 8 | T3bN0MX | 0.78 | yes | f | 22.5 | 3.2 | 2003 |
| FB120B | 60s | W | 61.1 | 3 + 4 = 7 | T3aN0MX | 0.88 | yes | nf | 1.3 | 20.84 | 2003 |
| FB174B | 60s | W | 6.9 | 3 + 4 = 7 | T3aN0MX | 0.93 | yes | f | 30.5 | 3.21 | 2003 |
| FB183B | 60s | W | 9.7 | 3 + 4 = 7 | T2cN0MX | 0.97 | yes | nf | 78.8 | 25.6 | 2003 |
| FB222B | 50s | W | 25.9 | 4 + 3 = 7 | T3aN0MX | 0.73 | yes | f | 1.2 | 2.4 | 2003 |
| FB238B | 60s | W | 15.9 | 3 + 4 = 7 | T3bN0MX | 0.91 | yes | nf | 30 | 29.97 | 2003 |
| FB41B | 60s | AA | 7.9 | 3 + 4 = 7 | T2cN0MX | 0.97 | yes | f | 82.1 | 4.1 | 2003 |
| FB421B | 60s | W | 4.5 | 3 + 4 = 7 | T3aN0MX | 0.94 | yes | f | 1.3 | 4.37 | 2003 |
| FB493B | 50s | AA | 7.1 | 3 + 3 = 6 | T3aN0MX | 0.96 | yes | nf | 62.5 | 17.84 | 2003 |
| FB586B | 50s | W | 7.2 | 3 + 4 = 7 | T3aN0Mx | 0.93 | yes | nf | 46.6 | 15.6 | 2004 |
| FB94B | 60s | W | 12.9 | 3 + 4 = 7 | T2cN0MX | 0.97 | yes | nf | 3.4 | 15.16 | 2003 |
| FB95 | 60s | W | 2.9 | 4 + 5 = 9 | T3aN0MX | 0.81 | yes | N/A | 17 | N/A | 2003 |
| GB195B | 60s | W | 10.1 | 3 + 4 = 7 | T2cN0MX | 0.97 | yes | nf | 53.2 | 23.8 | 2006 |
| GB222 | 60s | W | 6.8 | 3 + 3 = 6 | T2cN0MX | 0.98 | yes | f | 34.9 | 3.9 | 2004 |
| GB368 | 60s | W | 5.5 | 4 + 3 = 7 | T3aN0MX | 0.86 | yes | nf | 70.1 | 18 | 2004 |
| GB400B | 60s | W | 3.5 | 3 + 4 = 7 | T3bN0MX | 0.94 | yes | f | 29.6 | 4.22 | 2005 |
| HB021B | 50s | W | 5.9 | 3 + 3 = 6 | T2bN0MX | 0.98 | yes | f | 24.2 | 3.99 | 2004 |
| HB033B | 50s | W | 8.4 | 3 + 4 = 7 | T2cN0MX | 0.97 | no | nf | >90 | N/A | 2004 |
| HB207B | 60s | W | 6.3 | 4 + 5 = 9 | T3bN0MX | 0.75 | yes | f | 5.5 | 0.58 | 2005 |
| HB235B | 60s | W | 4.6 | 4 + 5 = 9 | T3bN1MX | 0.67 | yes | nf | 1.3 | 20.76 | 2010 |
| HB261B | 50s | W | 5.4 | 3 + 4 = 7 | T3aN0MX | 0.94 | no | nf | >90 | N/A | 2005 |
| HB303 | 60s | W | 31.3 | 3 + 4 = 7 | T2cN0MX | 0.96 | no | nf | >90 | N/A | 2005 |
| HB305B | 60s | W | 10.1 | 3 + 3 = 6 | T3bN0MX | 0.95 | yes | f | 1.4 | 3.9 | 2005 |
| HB312B | 70s | W | 1.1 | 4 + 4 = 8 | T3bN0MX | 0.86 | yes | nf | 7.4 | 15.23 | 2005 |
| HB327 | 60s | W | 9.5 | 4 + 4 = 8 | T2cN0MX | 0.88 | no | nf | >90 | N/A | 2005 |
| HB340 | 60s | W | 9.57 | 3 + 4 = 7 | T2cN0MX | 0.97 | yes | N/A | 4.54 | N/A | 2005 |
| HB346 | 60s | W | 17.2 | 3 + 4 = 7 | T3aN0MX | 0.91 | no | nf | >90 | N/A | 2005 |
| HB46B | 60s | W | 4.7 | 4 + 4 = 8 | T2cN0MX | 0.77 | yes | nf | 20.1 | 15.28 | 2005 |
| HB492 | 60s | W | 7.4 | 3 + 4 = 7 | T2cN0MX | 0.97 | yes | nf | 82.3 | 24 | 2005 |
| HB504B | 50s | U | 70 | 4 + 4 = 8 | T3bN0MX | 0.57 | yes | f | 4.3 | 0.69 | 2006 |
| HB526B | 60s | W | 8.7 | 3 + 3 = 6 | T3bN0MX | 0.95 | yes | f | 1.4 | 2.66 | 2009 |
| HB568B | 60s | W | 4.4 | 3 + 4 = 7 | T3bN0MX | 0.94 | yes | f | 22.4 | 4.19 | 2005 |
| HB591B | 60s | W | 13.6 | 3 + 4 = 7 | T3bN1MX | 0.87 | yes | f | 1.3 | 4.48 | 2007 |
| HB603B | 60s | W | 8.4 | 3 + 4 = 7 | T3aN1MX | 0.89 | yes | f | 22.1 | 11.91 | 2005 |
| HB658 | 60s | W | 20.6 | 4 + 3 = 7 | T3bN0MX | 0.79 | no | nf | >90 | N/A | 2005 |
| HB705 | 60s | W | 9.8 | 4 + 3 = 7 | T2cN0MX | 0.93 | no | nf | >90 | N/A | 2005 |
| IB071B | 60s | W | 2.6 | 3 + 4 = 7 | T3aN0MX | 0.95 | yes | f | 4.3 | 1.58 | 2007 |
| IB111 | 60s | W | 9.5 | 3 + 4 = 7 | T2cN0MX | 0.97 | no | nf | >90 | N/A | 2006 |
| IB112B | 60s | U | 4.7 | 3 + 4 = 7 | T3aN0MX | 0.94 | yes | nf | 55.8 | 30.59 | 2006 |

TABLE 3-continued

Clinical information for 143 blood samples.

| Case name | Age | Race | Pre-operative PSA | Gleason grad | Pathological stage | 5-year Nomogram | Prostate cancer recurrence | Fast recurrence | Time to relapse (Month) | PSADT | Surgical year |
|---|---|---|---|---|---|---|---|---|---|---|---|
| IB113B | 70s | W | 5.6 | 3 + 4 = 7 | T3bN0MX | 0.93 | yes | nf | 47.3 | 20.62 | 2005 |
| IB133 | 60s | W | 4.6 | 3 + 4 = 7 | T2cN0MX | 0.97 | yes | N/A | 34.9 | N/A | 2005 |
| IB134B | 70s | W | 15.7 | 4 + 5 = 9 | T3bN0MX | 0.68 | no | nf | >90 | N/A | 2005 |
| IB135 | 60s | W | 31.9 | 4 + 3 = 7 | T3bN1MX | 0.67 | yes | f | 35.2 | 2.2 | 2006 |
| IB136B | 50s | W | 19.6 | 4 + 4 = 8 | T3bN1MX | 0.54 | yes | f | 1.8 | 2.23 | 2005 |
| IB180 | 60s | W | 3 | 3 + 4 = 7 | T2cN0MX | 0.98 | no | nf | >90 | N/A | 2006 |
| IB289 | 60s | W | 9.96 | 3 + 4 = 7 | T2aN0MX | 0.97 | no | nf | >90 | N/A | 2006 |
| IB298B | 60s | W | 5.3 | 3 + 4 = 7 | T3bN0MX | 0.93 | yes | nf | 34.3 | 20.4 | 2006 |
| IB378 | 60s | W | 2.8 | 4 + 3 = 7 | T3bN0MX | 0.88 | no | nf | >90 | N/A | 2006 |
| IB483B | 50s | W | 5.2 | 3 + 4 = 7 | T2bN0MX | 0.97 | yes | f | 1.4 | 1.7 | 2007 |
| JB608 | 60s | W | 6.76 | 3 + 4 = 7 | T3aN0MX | 0.93 | yes | f | 1.3 | 0.6 | 2007 |
| IB627 | 60s | W | 7.86 | 3 + 4 = 7 | T2cN0MX | 0.97 | yes | N/A | 10.5 | N/A | 2006 |
| IB673 | 60s | W | 5.7 | 4 + 4 = 8 | T3aN0MX | 0.77 | yes | N/A | 22.8 | N/A | 2006 |
| IB684B | 60s | W | 4.1 | 3 + 4 = 7 | T3bN0MX | 0.94 | yes | nf | 60.9 | 77.4 | 2006 |
| JB378B | 60s | W | 5 | 3 + 3 = 6 | T2bN0MX | 0.99 | yes | nf | 18.4 | 45.8 | 2008 |
| JB426B | 60s | W | 5.7 | 3 + 4 = 7 | T2cN0MX | 0.97 | yes | f | 17.4 | 2.26 | 2007 |
| JB770B | 60s | W | 2.4 | 4 + 4 = 8 | T2cN0MX | 0.92 | yes | f | 33.8 | 2.99 | 2008 |
| KB170B | 70s | W | 14.1 | 3 + 4 = 7 | T3bN1MX | 0.87 | yes | f | 1.8 | 4.22 | 2008 |
| PR018B | 60s | W | 9 | 3 + 4 = 7 | T3aN0MX | 0.93 | yes | nf | 78 | 55.02 | 1999 |
| PR048 | 60s | W | 5.9 | 4 + 3 = 7 | T3aN0MX | 0.86 | no | nf | >90 | N/A | 2002 |
| PR065 | 60s | W | 10.2 | 4 + 5 = 9 | T4N0MX | 0.88 | yes | f | 16.7 | 2.1 | 2001 |
| PR073 | 60s | W | 7.8 | 3 + 5 = 8 | T3aN0MX | 0.93 | yes | f | 36.6 | 0.2 | 2000 |
| PR079B | 60s | W | 5.1 | 3 + 4 = 7 | T3aN0MX | 0.94 | yes | nf | 85.3 | 17.32 | 2000 |
| PR150 | 60s | W | 14.98 | 3 + 4 = 7 | T2bN0MX | 0.96 | yes | N/A | 36.1 | N/A | 2001 |
| PR151B | 60s | W | 8.1 | 4 + 3 = 7 | T2bN0MX | 0.93 | yes | nf | 35.5 | 35.19 | 2001 |
| PR151B2 | 60s | W | 8.9 | 4 + 3 = 7 | T2bN0MX | 0.93 | yes | nf | 36.9 | 26.65 | 2001 |
| PR227 | 60s | W | 4.46 | 3 + 4 = 7 | T2cN0MX | 0.97 | no | nf | >90 | N/A | 2002 |
| PR236B | 60s | W | 9.9 | 5 + 5 = 10 | T3bN0MX | 0.71 | yes | f | 1.3 | 3.91 | 2006 |
| PR300B | 50s | W | 20.3 | 3 + 4 = 7 | T3bN1MX | 0.85 | yes | f | 59 | 3.87 | 2003 |
| PR303B | 70s | W | 10.5 | 3 + 3 = 6 | T3bN0MX | 0.95 | yes | nf | 54.6 | 43.29 | 2004 |
| PR304B | 60s | W | 5.9 | 4 + 4 = 8 | T3bN0MX | 0.75 | yes | nf | 47.4 | 32.75 | 2002 |
| PR306B | 60s | W | 11.5 | 3 + 4 = 7 | T3bN0MX | 0.92 | yes | nf | 16.4 | 52.93 | 2002 |
| PR310B | 60s | W | 5.1 | 3 + 4 = 7 | T3bN0MX | 0.93 | yes | f | 22.8 | 1.58 | 2007 |
| PR311B | 60s | W | 10.2 | 4 + 4 = 8 | T3bN0MX | 0.71 | yes | nf | 61.6 | 160 | 2002 |
| PR363B | 60s | W | 12.5 | 3 + 4 = 7 | T2bN0Mx | 0.97 | yes | nf | 54 | 26 | 2002 |
| PR372 | 60s | W | 11.2 | 4 + 4 = 8 | T3aN0MX | 0.72 | yes | f | 4.5 | 1.4 | 2001 |
| PR375B | 50s | W | 11.3 | 3 + 4 = 7 | T3bN1MX | 0.87 | yes | f | 1.2 | 1.13 | 2002 |
| PR434B | 60s | W | 6.4 | 3 + 4 = 7 | T3aN0MX | 0.93 | yes | nf | 72.8 | 30.81 | 2000 |
| PR485 | 60s | W | 7.7 | 3 + 4 = 7 | T2bN0MX | 0.97 | yes | f | 35.2 | 2.1 | 2001 |
| PR490B | 60s | W | 5.7 | 3 + 4 = 7 | T2AN0MX | 0.97 | yes | nf | 45.5 | 35.6 | 1999 |
| PR521B | 50s | W | 6.4 | 3 + 4 = 7 | T2bN0MX | 0.97 | yes | nf | 79.2 | 15.51 | 2001 |
| PR524 | 60s | W | 8.5 | 3 + 2 = 5 | T2bN0MX | 0.98 | yes | N/A | 1.6 | N/A | 2000 |
| PR525 | 60s | W | 6.3 | 3 + 3 = 6 | T2aN0MX | 0.98 | yes | N/A | 18.4 | N/A | 2000 |
| PR527 | 60s | AA | 9.1 | 3 + 4 = 7 | T2bN0MX | 0.97 | yes | f | 3.78 | 3.78 | 2001 |
| PR528 | 60s | W | 1.3 | 3 + 3 = 6 | T3aN0MX | 0.98 | yes | N/A | 36.8 | N/A | 2000 |
| PR529 | 60s | W | 6.7 | 3 + 4 = 7 | T2bN0MX | 0.97 | yes | N/A | 16.6 | N/A | 2002 |
| PR530 | 60s | W | 4.4 | 3 + 4 = 7 | T2cN0MX | 0.98 | yes | N/A | 30 | N/A | 2002 |
| PR535 | 60s | W | 7 | 3 + 4 = 7 | T2bN0MX | 0.97 | no | nf | >90 | N/A | 2000 |
| PR536 | 60s | W | 5.4 | 3 + 4 = 7 | T2bN0MX | 0.97 | no | nf | >90 | N/A | 2002 |
| PR537 | 60s | W | 5.4 | 3 + 3 = 6 | T2bN0MX | 0.98 | no | nf | >90 | N/A | 2001 |
| PR541 | 60s | W | 29.4 | 4 + 4 = 8 | T3bN0MX | 0.64 | no | nf | >90 | N/A | 2002 |
| PR542 | 60s | W | 11.6 | 4 + 4 = 8 | T3bN0MX | 0.7 | no | nf | >90 | N/A | 2000 |
| PR543 | 60s | W | 20.8 | 4 + 4 = 8 | T3aN0MX | 0.68 | no | nf | >90 | N/A | 2000 |
| TP08-S00262 | 60s | W | 22.8 | 4 + 5 = 9 | T3bN0MX | 0.66 | yes | f | 1.6 | 0.2 | 2008 |
| TP08-S00268B | 60s | W | 2 | 3 + 4 = 7 | T2bN0MX | 0.98 | yes | f | 21.4 | 3.8 | 2009 |
| TP08-S00530B | 60s | W | 11.1 | 3 + 4 = 7 | T3bN0MX | 0.92 | yes | f | 1.3 | 3.31 | 2008 |
| TP08-S00542B | 50s | W | 4.3 | 3 + 4 = 7 | T2cN0MX | 0.98 | yes | f | 1.9 | 3.61 | 2009 |
| TP09-S0006B | 50s | W | 4.9 | 4 + 4 = 8 | T3bN1MX | 0.66 | yes | f | 4.6 | 1.23 | 2009 |
| TP09-S0408B | 70s | U | 2.9 | 4 + 4 = 8 | T3aN0MX | 0.81 | yes | f | 1.5 | 3.18 | 2010 |
| TP09-S0420B | 50s | W | 14.6 | 3 + 4 = 7 | T3bN1MX | 0.86 | yes | f | 1.4 | 3.7 | 2009 |
| TP09-S0420B2 | 50s | W | 12.8 | 3 + 4 = 7 | T3bN1MX | 0.87 | yes | f | 3.2 | 2.6 | 2009 |
| TP09-S0638B | 50s | W | 9.2 | 3 + 4 = 7 | T3bN1MX | 0.88 | yes | f | 1.4 | 1.83 | 1999 |
| TP09-S0721B | 50s | W | 29.3 | 3 + 4 = 7 | T3bN1MX | 0.84 | yes | f | 1.4 | 0.93 | 2010 |
| TP09-S0928 | 60s | W | 5.9 | 4 + 4 = 8 | T3bN1MX | 0.64 | yes | f | 1.3 | 0.1 | 2012 |

TABLE 3-continued

Clinical information for 143 blood samples.

| Case name | Age | Race | Pre-operative PSA | Gleason grad | Pathological stage | 5-year Nomogram | Prostate cancer recurrence | Fast recurrence | Time to relapse (Month) | PSADT | Surgical year |
|---|---|---|---|---|---|---|---|---|---|---|---|
| TP10-S093B | 60s | W | 4.1 | 3 + 4 = 7 | T3aN0MX | 0.94 | yes | nf | 43.8 | 39.96 | 2000 |
| TP12-S0740 | 50s | W | 25 | 4 + 5 = 9 | T3bN0MX | 0.65 | yes | f | 1.6 | 0.4 | 2012 |
| TP12-S0786 | 60s | W | 4.5 | 4 + 3 = 7 | T3bN1MX | 0.8 | yes | f | 1.2 | 0.6 | 2012 |
| TP12-S0790 | 60s | W | 24.2 | 4 + 3 = 7 | T3aN0MX | 0.8 | yes | f | 11.6 | 3.7 | 2012 |
| TP12-S0799 | 50s | W | 6.4 | 4 + 3 = 7 | T3aN0MX | 0.86 | yes | N/A | 13.1 | N/A | 2012 |
| TP12-S0805 | 50s | W | 7.6 | 4 + 3 = 7 | T3aN1MX | 0.78 | yes | N/A | 6.18 | N/A | 2013 |
| TP12-S0918 | 60s | W | 6.8 | 5 + 4 = 9 | T3bN1MX | 0.63 | yes | f | 0.9 | 2.3 | 2012 |
| TP12-S0945 | 50s | W | 10.3 | 4 + 5 = 9 | T3aN1MX | 0.61 | yes | f | 9.1 | 3.1 | 2012 |
| TP12-S0996 | 60s | W | 6.3 | 4 + 3 = 7 | T3aN1MX | 0.79 | yes | f | 1.4 | 0.4 | 2012 |
| TP12-S1059 | 60s | W | 10.6 | 4 + 4 = 8 | T3aN0MX | 0.73 | yes | f | 1.3 | 0.43 | 2012 |
| TP12-S1303 | 60s | W | 9.87 | 4 + 5 = 9 | T3bN0MX | 0.6 | yes | f | 1.78 | 0.5 | 2012 |
| TP13-S0048 | 60s | W | 22 | 4 + 4 = 8 | T3aN0MX | 0.68 | yes | f | 1.54 | 4 | 2012 |
| TP13-S0109 | 60s | W | 21.46 | 4 + 4 = 8 | T3bN1MX | 0.53 | yes | f | 1.7 | 1.4 | 2013 |
| TP13-S0147 | 60s | W | 14.1 | 4 + 3 = 7 | T2cN0MX | 0.92 | yes | N/A | 5.4 | N/A | 2013 |
| TP13-S0248 | 60s | W | 6.8 | 4 + 4 = 8 | T3bN1MX | 0.63 | yes | f | 2.1 | 0.52 | 2013 |
| TP13-S0456 | 50s | W | 29.9 | 4 + 5 = 9 | T3aN0MX | 0.66 | yes | f | 1.8 | 1.87 | 2013 |

TABLE 4

Prediction of prostate cancer recurrence based on leukocyte LSR, Gleason, Nomogram and fusion transcript status (the representative result for FIG. 3)

| Model | Accuracy | Sensitivity | Specificity | Youden index | AUC | ROC p-value |
|---|---|---|---|---|---|---|
| Equal split training data (n = 72) | | | | | | |
| LSR | 0.778 | 0.800 | 0.706 | 0.506 | 0.775 | $1.52 \times 10^{-4}$ |
| Nomogram | 0.681 | 0.691 | 0.647 | 0.338 | 0.619 | $1.43 \times 10^{-1}$ |
| Gleason | 0.347 | 0.218 | 0.765 | −0.017 | 0.496 | $9.54 \times 10^{-1}$ |
| Fusion | 0.651 | 0.586 | 0.786 | 0.372 | 0.686 | $1.53 \times 10^{-2}$ |
| L + N + F | 0.837 | 0.793 | 0.929 | 0.722 | 0.897 | $2.60 \times 10^{-9}$ |
| L + N + G | 0.639 | 0.545 | 0.941 | 0.487 | 0.778 | $7.34 \times 10^{-5}$ |
| N + F + G | 0.721 | 0.586 | 1.000 | 0.586 | 0.787 | $1.39 \times 10^{-4}$ |
| L + F + G | 0.814 | 0.759 | 0.929 | 0.687 | 0.897 | $5.44 \times 10^{-9}$ |
| L + N + F + G | 0.860 | 0.897 | 0.786 | 0.682 | 0.906 | $1.99 \times 10^{-9}$ |
| Equal split testing data (n = 71) | | | | | | |
| LSR | 0.761 | 0.792 | 0.667 | 0.459 | 0.768 | $8.10 \times 10^{-5}$ |
| Nomogram | 0.648 | 0.736 | 0.389 | 0.125 | 0.596 | $2.06 \times 10^{-1}$ |
| Gleason | 0.451 | 0.358 | 0.722 | 0.081 | 0.558 | $4.33 \times 10^{-1}$ |
| Fusion | 0.638 | 0.485 | 1.000 | 0.485 | 0.742 | $1.68 \times 10^{-6}$ |
| L + N + F | 0.872 | 0.909 | 0.786 | 0.695 | 0.898 | $1.13 \times 10^{-9}$ |
| L + N + G | 0.634 | 0.604 | 0.722 | 0.326 | 0.761 | $3.68 \times 10^{-4}$ |
| N + F + G | 0.596 | 0.424 | 1.000 | 0.424 | 0.714 | $5.89 \times 10^{-3}$ |
| L + F + G | 0.745 | 0.727 | 0.786 | 0.513 | 0.890 | $2.68 \times 10^{-9}$ |
| L + N + F + G | 0.851 | 0.909 | 0.714 | 0.623 | 0.892 | $1.34 \times 10^{-9}$ |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 5

Pairwise ROC p-value for prostate cancer recurrent status prediction (the geometric mean of the 10 cross-validations)

| | LSR | Nomogram | Gleason | Fusion | L + F + N + G | F + N + G | L + F + G | L + F + N | L + N + G |
|---|---|---|---|---|---|---|---|---|---|
| Training => Training | | | | | | | | | |
| LSR | 1 | 8.09E-2 | 8.63E-3 | 4.56E-1 | 5.38E-2 | 5.96E-1 | 8.84E-2 | 6.73E-2 | 4.07E-1 |
| Nomogram | | 1 | 2.79E-2 | 2.73E-1 | 7.47E-4 | 8.87E-2 | 1.62E-3 | 1.07E-3 | 3.37E-2 |
| Gleason | | | 1 | 5.52E-2 | 1.18E-5 | 7.73E-3 | 3.40E-5 | 1.83E-5 | 2.65E-3 |
| Fusion | | | | 1 | 1.50E-3 | 9.60E-2 | 2.68E-3 | 1.94E-3 | 2.77E-1 |
| L + F + N + G | | | | | 1 | 4.41E-2 | 5.15E-1 | 5.42E-1 | 1.09E-1 |
| F + N + G | | | | | | 1 | 8.49E-2 | 6.62E-2 | 6.84E-1 |
| L + F + G | | | | | | | 1 | 6.53E-1 | 1.61E-1 |
| L + F + N | | | | | | | | 1 | 1.33E-1 |
| L + N + G | | | | | | | | | 1 |
| Training => Testing | | | | | | | | | |
| LSR | 1 | 7.28E-2 | 5.78E-3 | 5.15E-1 | 2.86E-1 | 4.61E-1 | 2.57E-1 | 1.58E-1 | 2.52E-1 |
| Nomogram | | 1 | 1.51E-1 | 1.87E-1 | 6.84E-3 | 2.37E-1 | 5.94E-3 | 2.10E-3 | 1.65E-1 |
| Gleason | | | 1 | 2.90E-2 | 3.21E-4 | 5.01E-2 | 2.64E-4 | 5.73E-5 | 3.33E-3 |
| Fusion | | | | 1 | 2.51E-2 | 4.47E-1 | 1.55E-2 | 8.23E-3 | 6.08E-1 |
| L + F + N + G | | | | | 1 | 3.71E-2 | 3.56E-1 | 2.56E-1 | 1.59E-1 |
| F + N + G | | | | | | 1 | 4.51E-2 | 2.06E-2 | 6.07E-1 |

TABLE 5-continued

Pairwise ROC p-value for prostate cancer recurrent status prediction (the geometric mean of the 10 cross-validations)

|  | LSR | Nomogram | Gleason | Fusion | L + F + N + G | F + N + G | L + F + G | L + F + N | L + N + G |
|---|---|---|---|---|---|---|---|---|---|
| L + F + G |  |  |  |  |  |  | 1 | 1.77E−1 | 1.37E−1 |
| L + F + N |  |  |  |  |  |  |  | 1 | 7.87E−2 |
| L + N + G |  |  |  |  |  |  |  |  | 1 |

L—LSR;

N—Nomogram;

F—fusion transcript status;

G—Gleason grade;

L + N + F: LDA model to combine LSR, Nomogram and fusion transcript status;

L + N + G: LDA model to combine LSR, Nomogram and Gleason grade;

N + F + G: LDA model to combine Nomogram, fusion transcript status and Gleason grade;

L + N + F + G: LDA model to combine LSR, Nomogram, fusion transcript status and Gleason grade.

TABLE 6

Survival p-values for the predicted prostate cancer recurrent and non-recurrent groups (the geometric mean of the 10 cross-validations).

| Model | Survival p-value between two groups |
|---|---|
| LSR | $9.85 \times 10^{-5}$ |
| Nomogram | $3.83 \times 10^{-3}$ |
| Gleason | $1.13 \times 10^{-1}$ |
| Fusion | $6.75 \times 10^{-5}$ |
| LSR + Nomogram + Fusion | $2.88 \times 10^{-6}$ |
| LSR + Nomogram + Gleason | $2.67 \times 10^{-4}$ |
| Nomogram + Fusion + Gleason | $3.42 \times 10^{-4}$ |
| LSR + Fusion + Gleason | $4.75 \times 10^{-5}$ |
| LSR + Nomogram + Fusion + Gleason | $9.40 \times 10^{-5}$ |

TABLE 7

Pairwise survival p-value for prostate cancer recurrent status prediction (the geometric mean of the 10 cross-validations)

|  | LSR | Nomogram | Gleason | Fusion | L + F + N + G | F + N + G | L + F + G | L + F + N | L + N + G |
|---|---|---|---|---|---|---|---|---|---|
| LSR | 1 | 9.61E−3 | 5.29E−4 | 8.02E−2 | 3.63E−2 | 1.26E−2 | 9.07E−2 | 6.58E−3 | 8.47E−2 |
| Nomogram |  | 1 | 2.14E−2 | 8.48E−3 | 1.25E−2 | 1.42E−2 | 6.00E−3 | 3.45E−4 | 3.67E−2 |
| Gleason |  |  | 1 | 3.54E−4 | 4.98E−4 | 1.64E−3 | 2.52E−4 | 1.82E−5 | 1.44E−3 |
| Fusion |  |  |  | 1 | 7.46E−2 | 2.19E−2 | 8.70E−2 | 1.69E−2 | 7.18E−2 |
| L + F + N + G |  |  |  |  | 1 | 5.70E−2 | 1.37E−1 | 1.21E−2 | 3.47E−2 |
| F + N + G |  |  |  |  |  | 1 | 2.78E−2 | 2.40E−3 | 2.20E−2 |
| L + F + G |  |  |  |  |  |  | 1 | 2.13E−2 | 3.95E−2 |
| L + F + N |  |  |  |  |  |  |  | 1 | 3.18E−3 |
| L + N + G |  |  |  |  |  |  |  |  | 1 |

L—LSR;

N—Nomogram;

F—fusion transcript status;

G—Gleason grade;

L + N + F: LDA model to combine LSR, Nomogram and fusion transcript status;

L + N + G: LDA model to combine LSR, Nomogram and Gleason grade;

N + F + G: LDA model to combine Nomogram, fusion transcript status and Gleason grade;

L + N + F + G: LDA model to combine LSR, Nomogram, fusion transcript status and Gleason grade.

TABLE 8

Prediction of prostate cancer recurrent PSADT ≤4 months based on leukocyte LSR, Gleason, Nomogram and fusion transcript status (the representative result for FIG. 5).

| Model | Accuracy | Sensitivity | Specificity | Youden index | AUC | ROC p-value |
|---|---|---|---|---|---|---|
| Equal split training data (n = 65) | | | | | | |
| LSR | 0.662 | 0.500 | 0.784 | 0.284 | 0.674 | $1.33 \times 10^{-2}$ |
| Nomogram | 0.677 | 0.536 | 0.784 | 0.319 | 0.668 | $1.65 \times 10^{-2}$ |
| Gleason | 0.415 | 0.292 | 0.765 | 0.056 | 0.555 | $4.69 \times 10^{-1}$ |
| Fusion | 0.667 | 0.579 | 0.731 | 0.310 | 0.655 | $4.00 \times 10^{-2}$ |
| L + N + F | 0.822 | 0.842 | 0.808 | 0.650 | 0.858 | $1.26 \times 10^{-7}$ |
| L + N + G | 0.754 | 0.750 | 0.757 | 0.507 | 0.766 | $4.86 \times 10^{-5}$ |
| N + F + G | 0.800 | 0.632 | 0.923 | 0.555 | 0.764 | $1.99 \times 10^{-3}$ |
| L + F + G | 0.867 | 0.842 | 0.885 | 0.727 | 0.857 | $6.91 \times 10^{-7}$ |
| L + N + F + G | 0.800 | 0.842 | 0.769 | 0.611 | 0.864 | $2.39 \times 10^{-8}$ |
| Equal split testing data (n = 64) | | | | | | |
| LSR | 0.547 | 0.259 | 0.757 | 0.016 | 0.650 | $3.49 \times 10^{-2}$ |
| Nomogram | 0.672 | 0.593 | 0.730 | 0.322 | 0.716 | $7.66 \times 10^{-4}$ |
| Gleason | 0.453 | 0.333 | 0.737 | 0.070 | 0.530 | $6.74 \times 10^{-1}$ |
| Fusion | 0.707 | 0.667 | 0.731 | 0.397 | 0.699 | $1.37 \times 10^{-2}$ |
| L + N + F | 0.707 | 0.733 | 0.692 | 0.426 | 0.782 | $3.16 \times 10^{-4}$ |
| L + N + G | 0.656 | 0.593 | 0.703 | 0.295 | 0.727 | $6.57 \times 10^{-4}$ |
| N + F + G | 0.707 | 0.533 | 0.808 | 0.341 | 0.801 | $8.37 \times 10^{-5}$ |
| L + F + G | 0.610 | 0.400 | 0.731 | 0.131 | 0.717 | $9.56 \times 10^{-3}$ |
| L + N + F + G | 0.707 | 0.733 | 0.692 | 0.426 | 0.785 | $2.52 \times 10^{-4}$ |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 9

Pairwise ROC p-value for prostate cancer fast-recurrent status prediction (the geometric mean of the 10 cross-validations)

| | LSR | Nomogram | Gleason | Fusion | L + F + N + G | F + N + G | L + F + G | L + F + N | L + N + G |
|---|---|---|---|---|---|---|---|---|---|
| Training => Training | | | | | | | | | |
| LSR | 1 | 8.04E-1 | 1.80E-1 | 5.71E-1 | 2.81E-2 | 2.35E-1 | 6.94E-2 | 3.22E-2 | 2.73E-1 |
| Nomogram | | 1 | 1.89E-1 | 5.44E-1 | 1.99E-2 | 1.98E-1 | 5.59E-2 | 2.25E-2 | 1.58E-1 |
| Gleason | | | 1 | 2.08E-1 | 6.26E-4 | 1.92E-2 | 2.46E-3 | 7.82E-4 | 4.44E-2 |
| Fusion | | | | 1 | 5.93E-3 | 7.92E-2 | 1.00E-2 | 6.61E-3 | 3.90E-1 |
| L + F + N + G | | | | | 1 | 2.07E-1 | 4.63E-1 | 7.23E-1 | 1.13E-1 |
| F + N + G | | | | | | 1 | 4.55E-1 | 2.50E-1 | 4.90E-1 |
| L + F + G | | | | | | | 1 | 4.69E-1 | 2.26E-1 |
| L + F + N | | | | | | | | 1 | 1.24E-1 |
| L + N + G | | | | | | | | | 1 |
| Training => Testing | | | | | | | | | |
| LSR | 1 | 3.76E-1 | 2.99E-1 | 5.36E-1 | 1.10E-1 | 1.68E-1 | 1.61E-1 | 8.17E-2 | 1.36E-1 |
| Nomogram | | 1 | 6.40E-2 | 5.25E-1 | 3.68E-1 | 4.38E-1 | 4.69E-1 | 2.93E-1 | 6.03E-1 |
| Gleason | | | 1 | 1.61E-1 | 1.07E-2 | 2.15E-2 | 2.10E-2 | 7.48E-3 | 5.90E-2 |
| Fusion | | | | 1 | 1.01E-1 | 1.29E-1 | 9.96E-2 | 6.30E-2 | 5.55E-1 |
| L + F + N + G | | | | | 1 | 2.48E-1 | 3.95E-1 | 3.52E-1 | 4.32E-1 |
| F + N + G | | | | | | 1 | 5.11E-1 | 2.31E-1 | 5.50E-1 |
| L + F + G | | | | | | | 1 | 3.85E-1 | 5.49E-1 |
| L + F + N | | | | | | | | 1 | 3.61E-1 |
| L + N + G | | | | | | | | | 1 |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 10

Survival p-values for the predicted prostate cancer fast-recurrent and non-fast-recurrent groups (the geometric mean of the 10 cross-validations).

| Model | Survival p-value between two groups |
|---|---|
| LSR | $3.94 \times 10^{-3}$ |
| Nomogram | $2.14 \times 10^{-3}$ |
| Gleason | $8.16 \times 10^{-2}$ |
| Fusion | $3.50 \times 10^{-5}$ |
| LSR + Nomogram + Fusion | $1.48 \times 10^{-6}$ |
| LSR + Nomogram + Gleason | $5.24 \times 10^{-5}$ |
| Nomogram + Fusion + Gleason | $2.83 \times 10^{-6}$ |
| LSR + Fusion + Gleason | $3.43 \times 10^{-6}$ |
| LSR + Nomogram + Fusion + Gleason | $1.55 \times 10^{-7}$ |

TABLE 11

Pairwise survival p-value for prostate cancer fast-recurrent status prediction (the geometric mean of the 10 cross-validations)

| | LSR | Nomogram | Gleason | Fusion | L + F + N + G | F + N + G | L + F + G | L + F + N | L + N + G |
|---|---|---|---|---|---|---|---|---|---|
| LSR | 1 | 5.73E−2 | 3.05E−2 | 4.23E−3 | 1.93E−5 | 3.52E−4 | 3.11E−4 | 1.77E−4 | 3.74E−3 |
| Nomogram | | 1 | 1.59E−2 | 7.73E−3 | 3.03E−5 | 5.88E−4 | 7.40E−4 | 2.99E−4 | 9.52E−3 |
| Gleason | | | 1 | 2.41E−4 | 1.50E−6 | 2.09E−5 | 2.75E−5 | 1.16E−5 | 3.68E−4 |
| Fusion | | | | 1 | 1.83E−3 | 1.75E−2 | 9.05E−3 | 2.16E−2 | 7.07E−2 |
| L + F + N + G | | | | | 1 | 8.64E−3 | 9.32E−3 | 4.50E−2 | 7.81E−4 |
| F + N + G | | | | | | 1 | 7.12E−3 | 2.55E−2 | 7.03E−3 |
| L + F + G | | | | | | | 1 | 7.05E−3 | 4.54E−3 |
| L + F + N | | | | | | | | 1 | 8.65E−3 |
| L + N + G | | | | | | | | | 1 |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 12

Prediction of lethal prostate cancer recurrent (PSADT ≤4 months and relapse time ≤12 months) VS non-recurrence based on leukocyte LSR, Gleason, Nomogram and fusion transcript status (the average result).

| Model | Accuracy | Sensitivity | Specificity | Youden index | AUC | ROC p-value |
|---|---|---|---|---|---|---|
| Equal split training data (n = 35) | | | | | | |
| LSR | 0.783 | 0.739 | 0.829 | 0.568 | 0.818 | $7.88 \times 10^{-5}$ |
| Nomogram | 0.749 | 0.694 | 0.806 | 0.500 | 0.778 | $3.45 \times 10^{-4}$ |
| Gleason | 0.617 | 0.500 | 0.741 | 0.241 | 0.640 | $8.75 \times 10^{-2}$ |
| Fusion | 0.727 | 0.553 | 0.889 | 0.442 | 0.721 | $1.07 \times 10^{-2}$ |
| L + N + F | 0.957 | 0.966 | 0.947 | 0.913 | 0.979 | $1.25 \times 10^{-21}$ |
| L + N + G | 0.891 | 0.917 | 0.865 | 0.781 | 0.914 | $4.42 \times 10^{-10}$ |
| N + F + G | 0.840 | 0.836 | 0.848 | 0.684 | 0.862 | $1.21 \times 10^{-5}$ |
| L + F + G | 0.938 | 0.992 | 0.887 | 0.880 | 0.968 | $8.88 \times 10^{-18}$ |
| L + N + F + G | 0.977 | 0.983 | 0.971 | 0.954 | 0.991 | $7.24 \times 10^{-26}$ |
| Equal split testing data (n = 35) | | | | | | |
| LSR | 0.669 | 0.594 | 0.739 | 0.333 | 0.705 | $2.49 \times 10^{-2}$ |
| Nomogram | 0.686 | 0.676 | 0.694 | 0.371 | 0.788 | $1.12 \times 10^{-4}$ |
| Gleason | 0.640 | 0.529 | 0.744 | 0.274 | 0.659 | $5.11 \times 10^{-2}$ |
| Fusion | 0.768 | 0.594 | 0.900 | 0.493 | 0.747 | $4.19 \times 10^{-3}$ |
| L + N + F | 0.829 | 0.796 | 0.855 | 0.651 | 0.921 | $2.80 \times 10^{-11}$ |
| L + N + G | 0.743 | 0.741 | 0.744 | 0.486 | 0.800 | $2.98 \times 10^{-4}$ |
| N + F + G | 0.755 | 0.778 | 0.733 | 0.510 | 0.847 | $2.06 \times 10^{-5}$ |
| L + F + G | 0.773 | 0.758 | 0.787 | 0.545 | 0.903 | $7.01 \times 10^{-9}$ |
| L + N + F + G | 0.829 | 0.755 | 0.884 | 0.639 | 0.908 | $4.91 \times 10^{-8}$ |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 13

Prediction of lethal prostate cancer recurrent (PSADT ≤4 months and relapse time ≤12 months) VS non-recurrence based on leukocyte LSR, Gleason, Nomogram and fusion transcript status (the representative result for FIG. 8).

| Model | Accuracy | Sensitivity | Specificity | Youden index | AUC | ROC p-value |
|---|---|---|---|---|---|---|
| Equal split training data (n = 35) | | | | | | |
| LSR | 0.743 | 0.500 | 1.000 | 0.500 | 0.827 | $3.71 \times 10^{-5}$ |
| Nomogram | 0.743 | 0.667 | 0.824 | 0.490 | 0.791 | $1.07 \times 10^{-4}$ |
| Gleason | 0.571 | 0.444 | 0.706 | 0.150 | 0.592 | $3.34 \times 10^{-1}$ |
| Fusion | 0.714 | 0.538 | 0.867 | 0.405 | 0.703 | $2.46 \times 10^{-2}$ |
| L + N + F | 0.929 | 1.000 | 0.867 | 0.867 | 0.959 | $2.71 \times 10^{-13}$ |
| L + N + G | 0.914 | 1.000 | 0.824 | 0.824 | 0.951 | $3.46 \times 10^{-14}$ |
| N + F + G | 0.821 | 0.769 | 0.867 | 0.636 | 0.833 | $6.62 \times 10^{-4}$ |
| L + F + G | 0.893 | 1.000 | 0.800 | 0.800 | 0.938 | $4.14 \times 10^{-10}$ |
| L + N + F + G | 0.964 | 1.000 | 0.933 | 0.933 | 0.995 | $<10^{-30}$ |
| Equal split testing data (n = 35) | | | | | | |
| LSR | 0.686 | 0.471 | 0.889 | 0.359 | 0.717 | $2.60 \times 10^{-2}$ |
| Nomogram | 0.743 | 0.824 | 0.667 | 0.490 | 0.778 | $2.29 \times 10^{-4}$ |
| Gleason | 0.686 | 0.588 | 0.778 | 0.366 | 0.722 | $7.25 \times 10^{-3}$ |
| Fusion | 0.783 | 0.600 | 0.923 | 0.523 | 0.762 | $8.35 \times 10^{-3}$ |
| L + N + F | 0.913 | 1.000 | 0.846 | 0.846 | 1.000 | $<10^{-30}$ |
| L + N + G | 0.800 | 0.765 | 0.833 | 0.598 | 0.810 | $3.14 \times 10^{-4}$ |

TABLE 13-continued

Prediction of lethal prostate cancer recurrent (PSADT ≤4 months and relapse time ≤12 months) VS non-recurrence based on leukocyte LSR, Gleason, Nomogram and fusion transcript status (the representative result for FIG. 8).

| Model | Accuracy | Sensitivity | Specificity | Youden index | AUC | ROC p-value |
|---|---|---|---|---|---|---|
| N + F + G | 0.783 | 0.800 | 0.769 | 0.569 | 0.873 | $1.30 \times 10^{-4}$ |
| L + F + G | 0.826 | 0.900 | 0.769 | 0.669 | 0.950 | $1.06 \times 10^{-10}$ |
| L + N + F + G | 0.870 | 0.800 | 0.923 | 0.723 | 0.892 | $8.63 \times 10^{-6}$ |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 15

Survival p-values for the predicted prostate cancer lethal-recurrent and non-recurrent groups (the geometric mean of the 10 cross-validations).

| Model | Survival p-value between two groups |
|---|---|
| LSR | $5.79 \times 10^{-4}$ |
| Nomogram | $2.79 \times 10^{-3}$ |
| Gleason | $5.40 \times 10^{-2}$ |
| Fusion | $9.26 \times 10^{-4}$ |
| LSR + Nomogram + Fusion | $1.24 \times 10^{-5}$ |
| LSR + Nomogram + Gleason | $5.12 \times 10^{-5}$ |
| Nomogram + Fusion + Gleason | $3.49 \times 10^{-4}$ |
| LSR + Fusion + Gleason | $2.37 \times 10^{-4}$ |
| LSR + Nomogram + Fusion + Gleason | $4.24 \times 10^{-6}$ |

TABLE 14

Pairwise ROC p-value for prostate cancer lethal-recurrent and non-recurrent status prediction (the geometric mean of the 10 cross-validations)

| | LSR | Nomogram | Gleason | Fusion | L + F + N + G | F + N + G | L + F + G | L + F + N | L + N + G |
|---|---|---|---|---|---|---|---|---|---|
| *Training => Training* | | | | | | | | | |
| LSR | 1 | 6.05E−1 | 9.74E−2 | 2.21E−1 | 2.60E−2 | 3.37E−1 | 6.06E−2 | 3.94E−2 | 1.66E−1 |
| Nomogram | | 1 | 1.19E−2 | 3.46E−1 | 8.71E−3 | 3.29E−1 | 2.47E−2 | 1.47E−2 | 4.29E−2 |
| Gleason | | | 1 | 2.24E−1 | 3.11E−4 | 3.25E−2 | 9.01E−4 | 5.15E−4 | 1.34E−3 |
| Fusion | | | | 1 | 4.98E−4 | 6.97E−2 | 7.19E−4 | 5.85E−4 | 3.79E−2 |
| L + F + N + G | | | | | 1 | 9.06E−2 | 4.09E−1 | 5.55E−1 | 1.64E−1 |
| F + N + G | | | | | | 1 | 1.93E−1 | 1.22E−1 | 3.72E−1 |
| L + F + G | | | | | | | 1 | 4.80E−1 | 3.11E−1 |
| L + F + N | | | | | | | | 1 | 2.40E−1 |
| L + N + G | | | | | | | | | 1 |
| *Training => Testing* | | | | | | | | | |
| LSR | 1 | 3.75E−1 | 5.97E−1 | 2.47E−1 | 6.64E−2 | 1.26E−1 | 5.83E−2 | 4.39E−2 | 1.37E−1 |
| Nomogram | | 1 | 1.30E−2 | 3.36E−1 | 1.69E−1 | 3.13E−1 | 1.29E−1 | 1.03E−1 | 4.31E−1 |
| Gleason | | | 1 | 1.74E−1 | 1.52E−2 | 4.21E−2 | 1.28E−2 | 8.93E−3 | 5.76E−2 |
| Fusion | | | | 1 | 4.07E−2 | 2.19E−1 | 2.35E−2 | 1.20E−2 | 2.81E−1 |
| L + F + N + G | | | | | 1 | 2.31E−1 | 4.59E−1 | 4.72E−1 | 2.64E−1 |
| F + N + G | | | | | | 1 | 3.14E−1 | 1.78E−1 | 3.49E−1 |
| L + F + G | | | | | | | 1 | 2.66E−1 | 2.33E−1 |
| L + F + N | | | | | | | | 1 | 1.77E−1 |
| L + N + G | | | | | | | | | 1 |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

TABLE 16

Pairwise survival p-value for prostate cancer lethal-recurrent and non-recurrent status prediction (the geometric mean of the 10 cross-validations)

|  | LSR | Nomogram | Gleason | Fusion | L + F + N + G | F + N + G | L + F + G | L + F + N | L + N + G |
|---|---|---|---|---|---|---|---|---|---|
| LSR | 1 | 4.41E−2 | 6.20E−3 | 6.16E−2 | 1.48E−3 | 4.87E−2 | 3.56E−2 | 3.67E−3 | 2.89E−2 |
| Nomogram |  | 1 | 3.22E−2 | 1.17E−1 | 7.15E−4 | 4.34E−2 | 1.90E−2 | 2.12E−3 | 8.86E−3 |
| Gleason |  |  | 1 | 9.72E−3 | 4.50E−5 | 3.82E−3 | 2.50E−3 | 1.25E−4 | 5.26E−4 |
| Fusion |  |  |  | 1 | 1.56E−3 | 4.12E−2 | 3.79E−2 | 4.76E−3 | 2.75E−2 |
| L + F + N + G |  |  |  |  | 1 | 3.15E−3 | 8.83E−3 | 6.16E−2 | 1.07E−2 |
| F + N + G |  |  |  |  |  | 1 | 2.46E−2 | 6.80E−3 | 5.16E−2 |
| L + F + G |  |  |  |  |  |  | 1 | 2.54E−2 | 6.61E−2 |
| L + F + N |  |  |  |  |  |  |  | 1 | 2.80E−2 |
| L + N + G |  |  |  |  |  |  |  |  | 1 |

L—LSR;
N—Nomogram;
F—fusion transcript status;
G—Gleason grade;
L + N + F: LDA model to combine LSR, Nomogram and fusion transcript status;
L + N + G: LDA model to combine LSR, Nomogram and Gleason grade;
N + F + G: LDA model to combine Nomogram, fusion transcript status and Gleason grade;
L + N + F + G: LDA model to combine LSR, Nomogram, fusion transcript status and Gleason grade.

What is claimed is:

1. A method for treating a prostate cancer patient in need thereof comprising:
   a) obtaining a blood sample from the patient;
   b) determining the number and size of copy number variations (CNVs) in the sample from the patient;
   c) determining a large size ratio, wherein the large size ratio is calculated by dividing the number of CNVs that are larger in size than about 30 kb by the total number of CNVs;
   d) determining that the patient is at an increased risk for relapse when the large size ratio is equal to or greater than about 0.28; and
   e) performing a prophylactic and/or treatment regimen for the prostate cancer based on the determined increased risk for relapse, wherein the prophylactic and/or treatment regimen is selected from the group consisting of cryotherapy, radiation therapy, chemotherapy, hormone therapy, biologic therapy, bisphosphonate therapy, radical prostatectomy and combinations thereof.

2. A method for treating a prostate cancer patient in need thereof comprising
   a) obtaining a blood sample from the patient;
   b) determining the number and size of copy number variations (CNVs) in the sample from the patient;
   c) determining a large size ratio, wherein the large size ratio is calculated by dividing the number of CNVs that are larger in size than about 30 kb by the total number of CNVs;
   d) determining that the patient is at decreased risk for relapse when the large size ratio is less than about 0.28; and
   e) performing a biopsy related to the prostate cancer based on the determined decreased risk for relapse.

3. The method of claim 1, further comprising determining one or more of a Gleason grade of the cancer, nomogram and/or fusion gene MAN2A1-FER status.

4. The method of claim 2, further comprising determining one or more of a Gleason grade of the cancer, nomogram and/or fusion gene MAN2A1-FER status.

5. A method for treating a prostate cancer patient in need thereof comprising:
   a) obtaining a blood sample from the patient;
   b) determining the number and size of copy number variations (CNVs) in the sample from the patient;
   c) determining a large size ratio, wherein the large size ratio is calculated by dividing the number of CNVs that are larger in size than about 500 kb by the total number of CNVs;
   d) determining that the patient is at an increased risk for rapid relapse when the large size ratio is equal to or greater than about 0.02; and
   e) performing a prophylactic and/or treatment regimen for the prostate cancer based on the determined increased risk for rapid relapse, wherein the prophylactic and/or treatment regimen is selected from the group consisting of cryotherapy, radiation therapy, chemotherapy, hormone therapy, biologic therapy, bisphosphonate therapy, radical prostatectomy and combinations thereof.

6. The method of claim 5, further comprising determining one or more of a Gleason grade of the cancer, nomogram and/or fusion gene MAN2A1-FER status.

7. A method for treating a prostate cancer patient in need thereof comprising
   a) obtaining a blood sample from the patient;
   b) determining the number and size of copy number variations (CNVs) in the sample from the patient;
   c) determining a large size ratio, wherein the large size ratio is calculated by dividing the number of CNVs that are larger in size than about 500 kb by the total number of CNVs;
   d) determining that the patient is at decreased risk for rapid relapse when the large size ratio is less than about 0.02; and
   e) performing a biopsy related to the prostate cancer based on the determined decreased risk for rapid relapse.

8. The method of claim 7, further comprising determining one or more of a Gleason grade of the cancer, nomogram and/or fusion gene MAN2A1-FER status.

* * * * *